(12) United States Patent
Stappenbeck et al.

(10) Patent No.: US 9,637,514 B1
(45) Date of Patent: May 2, 2017

(54) OXYSTEROLS AND HEDGEHOG SIGNALING

(71) Applicant: MAX BioPharma, Inc., Los Angeles, CA (US)

(72) Inventors: Frank Stappenbeck, Los Angeles, CA (US); Yi Chiao Fan, Rosemead, CA (US)

(73) Assignee: MAX BIOPHARMA, INC., Los Angeles, CA (US)

( * ) Notice: Subject to any disclaimer, the term of this patent is extended or adjusted under 35 U.S.C. 154(b) by 0 days.

(21) Appl. No.: 15/055,402

(22) Filed: Feb. 26, 2016

Related U.S. Application Data

(60) Provisional application No. 62/246,528, filed on Oct. 26, 2015, provisional application No. 62/279,549, filed on Jan. 15, 2016.

(51) Int. Cl.
C07J 9/00 (2006.01)

(52) U.S. Cl.
CPC ...................... C07J 9/00 (2013.01)

(58) Field of Classification Search
USPC .................................. 514/182, 278
See application file for complete search history.

(56) References Cited

U.S. PATENT DOCUMENTS

| | | | |
|---|---|---|---|
| 3,131,179 A * | 4/1964 | Hoffmann | C07J 43/003 540/109 |
| 4,229,447 A | 10/1980 | Porter | |
| 4,476,116 A | 10/1984 | Anik | |
| 4,596,795 A | 6/1986 | Pitha | |
| 4,755,386 A | 7/1988 | Hsiao et al. | |
| 5,011,692 A | 4/1991 | Fujioka et al. | |
| 5,017,381 A | 5/1991 | Maruyama et al. | |
| 5,116,817 A | 5/1992 | Anik | |
| 5,229,135 A | 7/1993 | Philippon et al. | |
| 5,739,136 A | 4/1998 | Ellinwood, Jr. et al. | |
| 5,837,284 A | 11/1998 | Mehta et al. | |
| 5,840,329 A | 11/1998 | Bai | |
| 5,858,401 A | 1/1999 | Bhalani et al. | |
| 6,391,452 B1 | 5/2002 | Antonsen et al. | |
| 6,667,048 B1 | 12/2003 | Lambert et al. | |
| 6,960,563 B2 | 11/2005 | Egbaria et al. | |
| 7,897,588 B2 | 3/2011 | Parhami | |
| 8,022,052 B2 | 9/2011 | Parhami et al. | |
| 8,545,311 B2 * | 10/2013 | Shore | G07F 17/3288 463/25 |
| 2005/0049230 A1 | 3/2005 | Henrich et al. | |
| 2006/0025393 A1 | 2/2006 | Liao et al. | |
| 2008/0020381 A1 | 1/2008 | Henrich et al. | |
| 2011/0008297 A1 * | 1/2011 | Parhami | A61K 31/575 424/93.7 |
| 2012/0309730 A1 * | 12/2012 | Parhami | A61K 31/56 514/176 |
| 2015/0118277 A1 * | 4/2015 | Parhami | A61K 45/06 424/423 |
| 2015/0140059 A1 * | 5/2015 | Parhami | A61K 31/575 424/423 |
| 2016/0159850 A1 * | 6/2016 | Parhami | A61K 31/575 424/93.7 |

FOREIGN PATENT DOCUMENTS

| | | |
|---|---|---|
| EP | 0477107 A1 | 3/1992 |
| EP | 0562849 A2 | 9/1993 |
| JP | 08268917 | 10/1996 |
| JP | 2009000103 | 1/2009 |
| JP | 2014076066 | 5/2014 |
| WO | WO-9303732 | 3/1993 |
| WO | WO-9521617 | 8/1995 |
| WO | WO-9809935 | 3/1998 |
| WO | WO-9958549 A1 | 11/1999 |
| WO | WO-03030857 A1 | 4/2003 |
| WO | WO-2004103320 A2 | 12/2004 |
| WO | WO-2005020928 A2 | 3/2005 |
| WO | WO-2006110490 A2 | 10/2006 |
| WO | WO-2007028101 A2 | 3/2007 |
| WO | WO-2007098281 A2 | 8/2007 |
| WO | WO-2007103162 A2 | 9/2007 |
| WO | WO-2008011071 A2 | 1/2008 |
| WO | WO-2008115469 A2 | 9/2008 |
| WO | WO-2009073186 A1 | 6/2009 |
| WO | WO-2009108804 A2 | 9/2009 |
| WO | WO-2010079594 A1 | 7/2010 |
| WO | WO-2010088409 A2 | 8/2010 |
| WO | WO-2011006087 A1 | 1/2011 |
| WO | WO-2011025064 A1 | 3/2011 |
| WO | WO-2011053048 A2 | 5/2011 |

(Continued)

OTHER PUBLICATIONS

Parhami et al. (AN 2011:1072261, zcaplus, abstract of WO 2011103175, pub. Date Feb. 16, 2011).*
Parhami, Farhad (AN 2008:1158747, zcaplus, DN 149:370581 Title: Role of hedgehog signaling in atherosclerosis and cardiovascular disease, abstract of WO 2008115469).*
Karl Hoffman (AN 1961:131459, ZCAPLUS, dn 55:131459, Abstract of GB 869007, US EQ 3131179).*
Arai et al., Synthesis of ponasterone A derivatives with various steroid skeleton moieties and evaluation of their binding to the ecdysone receptor of Kc cells. Steroids, 73:1452-1464 (2008).
Bannai et al, Studies on steroids. Part 37. Synthesis of the four stereoisomers of 20,22-Epoxycholesterol. Journal of the Chemical Society, Perkin Transactions 1: Organic and Bio-Organic Chemistry (1972-1999), (19):2116-20 (1976).
Benelli et al, Cholesterol hydroxylations in adrenal cortex and testis of the thyroidectomized RAT. Thyroid Research VIII. Proc.Eighth Int. Thyroid Congr., Sydney, Australia, p. 327-30 (1980).
Burstein et al, Substrate-induced difference spectra and cholesterol to pregnenolone conversation with adrenal heme protein P-450. Biochemistry, 11(4):573-7 (1972).

(Continued)

Primary Examiner — Sabiha N Qazi
(74) Attorney, Agent, or Firm — Wilson Sonsini Goodrich & Rosati

(57) ABSTRACT

Described herein are compounds and pharmaceutical compositions containing such compounds which inhibit Hedgehog signaling. Also described herein are methods for using such Hedgehog signaling inhibitors, alone or in combination with other compounds, for treating diseases or conditions that would benefit from inhibition of Hedgehog signaling.

20 Claims, 5 Drawing Sheets

(56) References Cited

FOREIGN PATENT DOCUMENTS

| WO | WO-2011073419 A1 | 6/2011 |
| --- | --- | --- |
| WO | WO-2011103175 A2 | 8/2011 |
| WO | WO-2012024584 A2 | 2/2012 |
| WO | WO-2013036835 A1 | 3/2013 |
| WO | WO-2013169397 A1 | 11/2013 |
| WO | WO-2013169399 A1 | 11/2013 |
| WO | WO-2014020577 A1 | 2/2014 |
| WO | WO-2014179756 A1 | 11/2014 |
| WO | WO-2015168636 A1 | 11/2015 |

OTHER PUBLICATIONS

Burstein et al., Reactions of 20-Hhrdoxylated steroids with bovine adernal tissue preparations. Steroids, 13(3):399-412 (1968).
Burstein et al, Inhibition of the conversion of cholesterol to pregnenolone in bovine Adrenocortical preparations. Steroids, 27(3):361-82 (1976).
Chaudhuri et al, Stereochemistry of the addition reactions of Grignard reagents to 20-keto steroids. Synthesis of $17_\alpha,20_\alpha$-Dihydroxycholesterol. Journal of Organic Chemistry, 34(12):3759-3766 (1969).
Ciobanu et al., Synthesis and steroid sulphatase inhibitory activity of C19- and C21-steroidal derivatives bearing a benzyl-inhibiting group. Eur.J.Med.Chem., 36:659-671 (2001).
DiBussolo et al, Structural elucidation of sterols by reversed-phase liquid chromatography: I. Assignment of retention coefficients to various groups. Journal of Chromatographic Science, 20(5):193-202 (1982).
Duncan, J. L., Effects of streptolysin O on mammalian cells. Pathog. Streptococci, Proc. Vllth Int. Symp. Streptococci and Streptococcal Diseases, p. 56-57, Sep. 1978.
Heer and Hoffmann, Uber Pyridyl-Steroide. I., Helvetica Chimica Acta, Chapter 214, p. 1804-1813 (1956).
Hochberg et al, Transient, reactive intermediates in the biosynthesis of pregnenolone from cholesterol. International Congress Series (1973), (Endocrinol., Proc. Int. Congr., 4th, 1972), 273:808-13.
Horie et al, Heme-linked spectral changes of the protein moiety of hemoproteins in the near ultraviolet region. Journal of Biochemistry, 97(1):281-293 (1985).
Janowski et al, An oxysterol signaling pathway mediated by the nuclear receptor LXRα. Nature, 383(6602):728-731 (1996).
Klinefelter et al, Effect of Luteinizing hormone deprivation in Situ on steroidogenesis of rat leydig cells purified by a multistep procedure. Biology of Reproduction, 36(3):769-83 (1987).
Korahani et al, Autoxidation of cholesterol fatty ac ids esters in solid state and aqueous dispersion. Lipids, 17(10):703-8 (1982).
Kusano et al., Antifungal properties of solanum alkaloids. Che. Pharm. Bull., 35(12):4862-4867 (1987).
Morisaki et al, Stereochemical specificity at Carbon-20 and -22 of hydroxylated cholesterols for side-chain cleavage by adrenocortical cytochrome P-450$_{scc}$. FEBS Letters, 72(2):337-40 (1976).
Myers et al., Hedgehog pathway modulation by multiple lipid binding sites on the Smoothened effector of signal response. Developmental Cell, 26:346-357 (2013).
Nachtergaele et al., Oxysterols are allosteric activators of the oncoprotein Smoothened. Nature Chemical Biology, 8:211 (2012). Published online at DOI:10.1038/NCHEMBIO.765.
Nedelcu et al., Oxysterol binding to the extracellular domain of Smoothened in Hedgehog signaling. Nature Chemical Biology. Published online Jul. 7, 2013 at: DOI:10:1038/INCHEMB10.1290.
Nes and Varkey, (Z)-17(20)-Dehydrocholesterol. A new sterol with C-21 and C-22 spatially fixed. Journal of Organic Chemistry, 41(21):3429-2933 (1976).
Neyses et al, Cholesterol and its oxidized derivatives modulate the calcium channel in human red blood cells. Journal of Hypertension, 2(Suppl. 3):489-92 (1984).
Peng et al, Effects of oxygenated derivatives of cholesterol on cholesterol uptake by cultured aortic smooth muscle cells. Artery, 13(3):144-64 (1985).
Pratt et al, Membrane sterols and the development of the preimplantation mouse embryo Journal of Embryology and Experimental Morphology, 60:303-19 (1980).
Saito et al, Lysis of platelets and erythrocytes by the incorporation of a unique oxygenated sterol: 22R-hydroxycholesterol. Journal of Membrane Biology, 83(1-2):187-191 (1985).
Shimada et al, Rapid modulation of platelet aggregation in plasma by oxygenated sterols. Journal of Applied Biochemistry, 6(3):151-55 (1984).
"Liquid Dosage Forms." In: Encyclopedia of Pharmaceutical Technology, 2nd Ed., vol. 1, edited by James Swarbrick and James C. Boylan, New York: Marcel Dekker, Inc., pp. 754-757 (2002).
Stappenbeck et al, Novel oxysterols activate the Hedgehog pathway and induce osteogenesis. Bioorganic & Medicinal Chemistry Letters, 22(18):5893-5897 (2012).
Tuckey et al, Kinetics of the incorporation of adrenal cytochrome P-450$_{scc}$ into phosphatidylcholine vesicles. Journal of Biological Chemistry, 257(16):9309-14 (1982).
Veldhuis et al, An inhibitory role for the protein kinase C pathway in ovarian steroidogenesis. Biochemical Journal, 239(3) :505-11 (1986).
Velgova et al, On Steroids. CXXVL. Further compounds with antisclerotization effect on Pyrrhocoris apterus L. Larvae; Structure and Activity correlations. Collection of Czechoslovak Chemical Communications, 34(11):3354-3376 (1969).
Viola et al, Side chain degradation and microbial reduction of different steroids by Aspergillus aureogulgens. Journal of Steroid Biochemistry, 19(4):1451-8 (1983).
Voigt et al, Massenspektrometrie von 20-Pyridylsteroiden. Pharmazie, 30(4):213-216 (1975) (In German, no English language translation provided).
Watanabe et al., Stereoselective synthesis of (22R)- and (22S)-castasterone/ponasterone A hybrid compounds and evaluation of their molting hormone activity. Steroids, 69:483-491 (2004).
PCT/US2016/058708 International Search Report and Written Opinion dated Jan. 17, 2017.

* cited by examiner

OXYSTEROLS AND HEDGEHOG SIGNALING

CROSS-REFERENCE

This application claims benefit of U.S. Provisional Application No. 62/246,528, filed on Oct. 26, 2015, and U.S. Provisional Application No. 62/279,549, filed on Jan. 15, 2016, both of which are herein incorporated by reference in their entirety.

BACKGROUND OF THE INVENTION

Hedgehog molecules and related signaling pathway have been shown to play key roles in a variety of physiological processes including, but not limited to, tissue patterning, mitogenesis, morphogenesis, cellular differentiation, differentiation of stem cells into mature cells, embryonic development, cardiovascular disease, bone formation, and cancer.

Despite developments of various approaches and compounds able to interfere with the Hedgehog signaling pathway, regulation and in particular inhibition of Hedgehog signaling remains challenging.

SUMMARY OF THE INVENTION

Described herein are inhibitors of Hedgehog signaling. Also disclosed herein are methods for synthesizing such Hedgehog signaling inhibitors and methods for using such Hedgehog signaling inhibitors in the treatment of diseases wherein inhibition of Hedgehog signaling provides therapeutic benefit to the patient. Further described are pharmaceutical formulations that include a Hedgehog signaling inhibitor.

In one aspect are compounds having the structure of Formula (I):

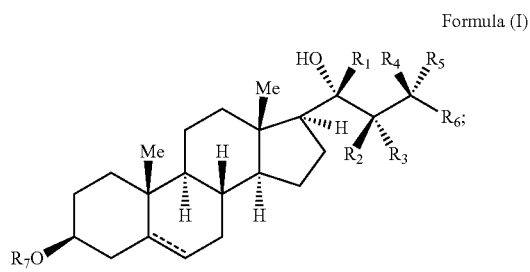

Formula (I)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- $R_6$ is substituted or unsubstituted aryl or substituted or unsubstituted heteroaryl; ===== is a single or double bond;
- $R_2$, $R_3$, $R_4$, and $R_5$ are independently hydrogen, deuterium, or —OH;
- $R_7$ is hydrogen, substituted or unsubstituted $C_1$-$C_8$alkyl, or —C(O)$NR_8R_9$; and
- $R_8$ and $R_9$ are independently hydrogen, substituted or unsubstituted $C_1$-$C_8$alkyl, or substituted or unsubstituted aryl.

In some embodiments are compounds of Formula (I) having the structure of Formula (Ia):

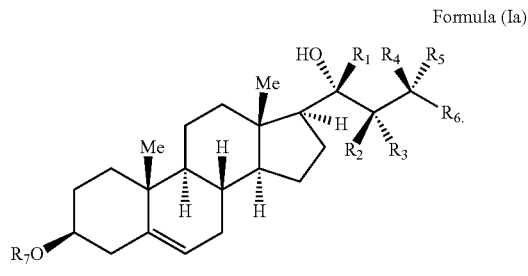

Formula (Ia)

In some embodiments are compounds of Formula (I) having the structure of Formula (Ib):

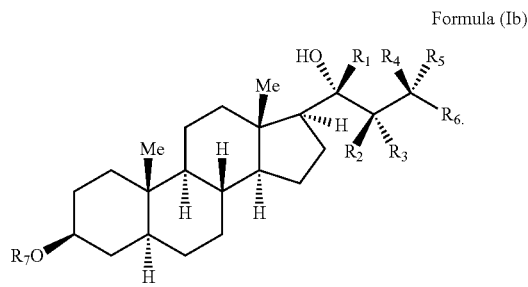

Formula (Ib)

In some embodiments is a compound of Formula (I), (Ia), or (Ib), wherein $R_2$, $R_3$, $R_4$, and $R_5$ are each deuterium. In some embodiments is a compound of Formula (I), (Ia), or (Ib), wherein $R_2$, $R_3$, $R_4$, and $R_5$ are each hydrogen. In some embodiments is a compound of Formula (I), (Ia), or (Ib), wherein $R_2$ is —OH, and $R_3$, $R_4$, and $R_5$ are each hydrogen. In some embodiments is a compound of Formula (I), (Ia), or (Ib), wherein $R_1$ is substituted or unsubstituted $C_1$-$C_8$alkyl. In some embodiments is a compound of Formula (I), (Ia), or (Ib), wherein $R_1$ is —$CH_3$. In some embodiments is a compound of Formula (I), (Ia), or (Ib), wherein $R_1$ is substituted or unsubstituted aryl. In some embodiments is a compound of Formula (I), (Ia), or (Ib), wherein $R_1$ is unsubstituted phenyl. In some embodiments is a compound of Formula (I), (Ia), or (Ib), wherein $R_6$ is substituted or unsubstituted aryl. In some embodiments is a compound of Formula (I), (Ia), or (Ib), wherein $R_6$ is substituted phenyl. In some embodiments is a compound of Formula (I), (Ia), or (Ib), wherein $R_6$ is phenyl substituted with one F. In some embodiments is a compound of Formula (I), (Ia), or (Ib), wherein $R_7$ is hydrogen. In some embodiments is a compound of Formula (I), (Ia), or (Ib), wherein $R_7$ is substituted or unsubstituted $C_1$-$C_8$alkyl. In some embodiments is a compound of Formula (I), (Ia), or (Ib), wherein $R_7$ is —$CH_3$. In some embodiments is a compound of Formula (I), (Ia), or (Ib), wherein $R_7$ is —C(O)$NR_8R_9$. In some embodiments is a compound of Formula (I), (Ia), or (Ib), wherein $R_7$ is substituted or unsubstituted $C_1$-$C_8$alkyl. In some embodiments is a compound of Formula (I), (Ia), or (Ib), wherein $R_7$ is —C(O)$NR_8R_9$, and $R_8$ and $R_9$ are independently substituted or unsubstituted $C_1$-$C_8$alkyl.

In another aspect, provided herein, is a pharmaceutical composition comprising a compound of Formula (I), (Ia), or (Ib), and a pharmaceutically acceptable excipient.

Also provided herein, in some embodiments, is a method for inhibiting a Hedgehog signaling pathway in a cell, the method comprising contacting the cell with one or more compounds of Formula (I), (Ia), or (Ib) in a sufficient amount to inhibit the Hedgehog signaling.

Also provided herein, in some embodiments, is a method of inhibiting tumorigenesis through interfering with tumorigenic signaling pathways in a mammal comprising locally or systemically administering to the mammal a therapeutically effective amount of a compound of Formula (I), (Ia), or (Ib).

Also provided herein, in some embodiments, is a method of treating a disease, disorder or condition associated with an aberrant regulation of a Hedgehog pathway in a mammal comprising locally or systemically administering to the mammal a therapeutically effective amount of a compound of Formula (I), (Ia), or (Ib). In some embodiments is a method of treating a disease, disorder or condition associated with an aberrant regulation of a Hedgehog pathway in a mammal comprising locally or systemically administering to the mammal a therapeutically effective amount of a compound of Formula (I), (Ia), or (Ib); wherein the disease is cancer. In some embodiments is a method of treating a disease, disorder or condition associated with an aberrant regulation of a Hedgehog pathway in a mammal comprising locally or systemically administering to the mammal a therapeutically effective amount of a compound of Formula (I), (Ia), or (Ib); wherein the disease is cancer and the cancer is selected from basal cell carcinoma, melanoma, leukemia, multiple myeloma, stomach cancer, pancreatic cancer, bladder cancer, prostate cancer, ovarian cancer, bone cancer, brain cancer, lung cancer, breast cancer, and skin cancer.

In some embodiments, the compound of Formula (I), (Ia), or (Ib) is administered orally, intravenously, intraperitoneally, or subcutaneously.

In some embodiments, the compound of Formula (I), (Ia), or (Ib) is administered orally, intravenously, intraperitoneally, subcutaneously, or as an aerosol.

In some embodiments, the method further comprises administrating a second agent therapuetic agent. In some embodiments, the method further comprises administrating a second agent therapuetic agent, wherein the second therapeutic agent is an anti-tumor agent. In some embodiments, the method further comprises administrating a second agent therapuetic agent, wherein the second therapeutic agent is an anti-tumor agent and the anti-tumor agent is an oxysterol, a Hedgehog pathway antagonist, a chemotherapeutic agent, or a combination thereof.

In some embodiments, the method further comprises the administration of radiation therapy.

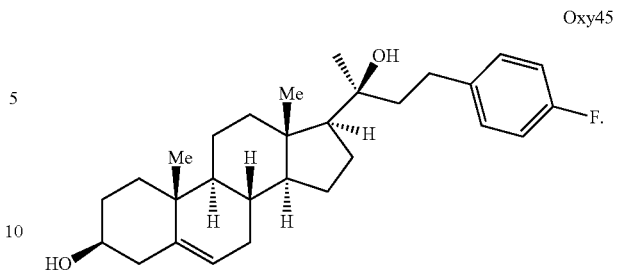

Figure 3:
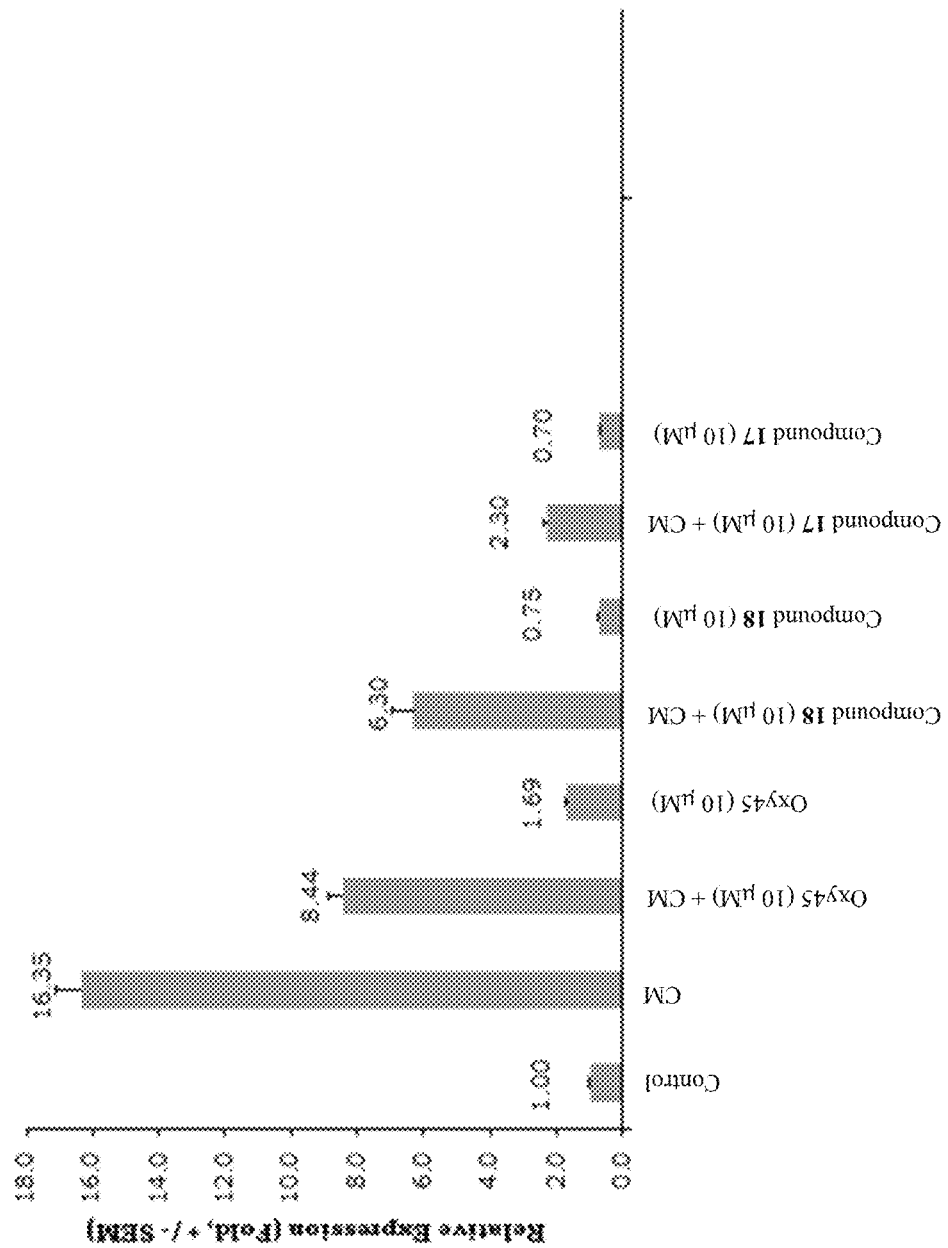

FIG. 3 shows the relative expression of Hedgehog target gene PTCH in NIH3T3 cells. The relative expression (fold) of PTCH is plotted for Oxy45, compound 17 and compound 18, each at a concentration of 10 µM in conditioned medium (CM) or 5% FBS in DMEM in comparison with a control (DMSO alone).

Figure 4:
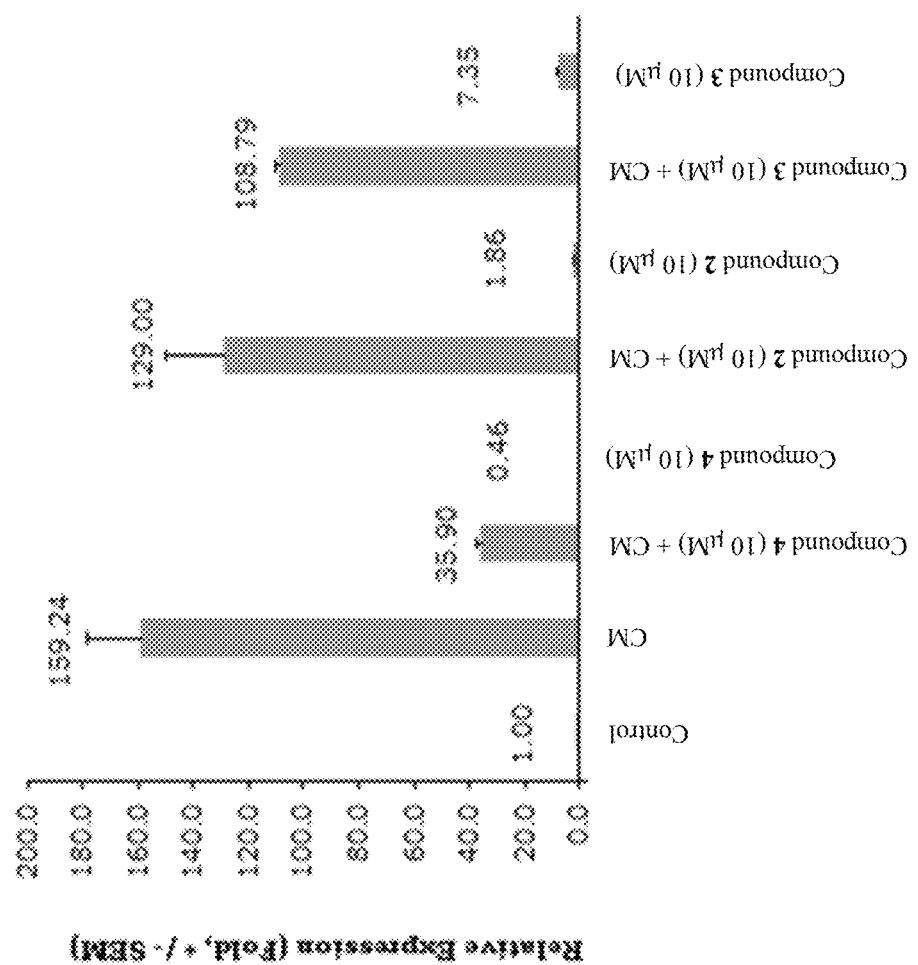

FIG. 4 shows the relative expression of Hedgehog target gene Gli1 in NIH3T3 cells. The relative expression (fold) of Gli1 is plotted for compound 2, compound 3, and compound 4, each at a concentration of 10 µM in conditioned medium (CM) or 5% FBS in DMEM in comparison with a control (DMSO alone) and CM.

Figure 5:
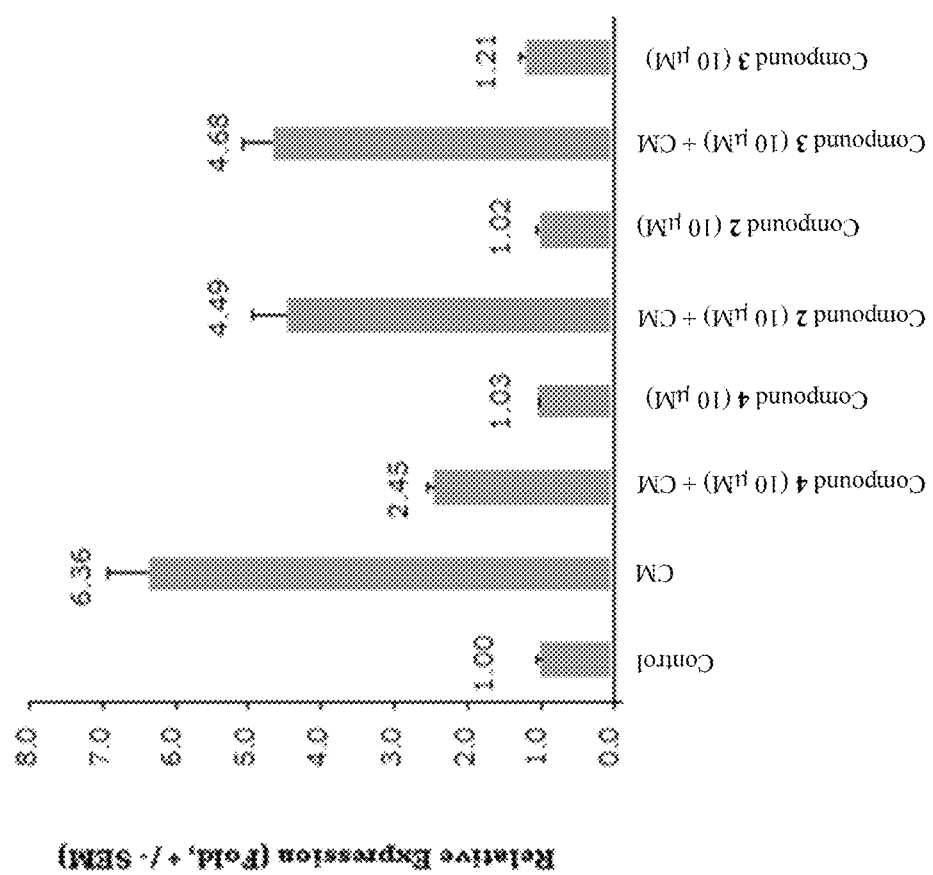

FIG. 5 shows the relative expression of Hedgehog target gene PTCH in NIH3T3 cells. The relative expression (fold) of PTCH is plotted for compound 2, compound 3, and compound 4, each at a concentration of 10 µM in conditioned medium (CM) or 5% FBS in DMEM in comparison with a control (DMSO alone) and CM.

DETAILED DESCRIPTION OF THE INVENTION

Hedgehog Signaling

The Hedgehog signaling pathway is a cell signalling pathway that is activated by a Hedgehog ligand (Sonic hedgehog (SHh), Desert hedgehog (DHh), and Indian hedgehog (IHh)). The pathway is one of the key regulators of embryonic development, but Hedgehog signaling remains important in the adult. Sonic hedgehog has been shown to promote the proliferation of adult stem cells from various tissues. However, activation of the Hedgehog pathway has also been implicated in the development of cancers in various organs, including brain, lung, mammary gland, prostate and skin. Hedgehog signaling also appears to be a crucial regulator of angiogenesis and thus metastasis. The initiating step in Hedgehog signaling is controlled by an interaction between two transmembrane proteins, Patched 1 (PTCH) and Smoothened (Smo). Upon binding of a Hedgehog agonist, PTCH is inactivated and Smo is released allowing Gli1 transcription factors to initiate target gene transcription. Smo can function as an oncogene. Activating Smo mutations can lead to unregulated activation of the Hedgehog pathway and cancer.

Definitions

As used herein, the terms "treat," "treating" or "treatment," include alleviating, abating or ameliorating at least one symptom of a disease or condition, preventing additional symptoms, preventing progression of the condition, inhibiting the disease or condition, e.g., arresting the development of the disease or condition, relieving the disease or condition, causing regression of the disease or condition, relieving a condition caused by the disease or condition, or stopping the symptoms of the disease or condition. In one embodiment, treatment is prophylactic treatment. In another embodiment, treatment refers to therapeutic treatment.

As used herein, "administer" means to provide a treatment, for example to prescribe a treatment, apply a treatment, or distribute a treatment. In some instances, to administer means a medical professional prescribes a treatment which a patient applies (e.g., the patient applies a CPAP device, consumes a medication, or injects a medication). Administration of a medical treatment does not require the immediate or constant supervision of a medical professional.

"Co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "subject" or "patient" encompasses mammals and non-mammals. "Mammals" include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one embodiment, the mammal is a human.

A "tissue" comprises two or more cells. The two or more cells may have a similar function and/or function. The tissue may be a connective tissue, epithelial tissue, muscular tissue, or nervous tissue. Alternatively, the tissue is a bone, tendon (both referred to as musculoskeletal grafts), cornea, skin, heart valve, or vein.

An "organ" comprises two or more tissues. The two or more tissues may perform a specific function or group of functions. In some instances, the organ is a lung, mouth, nose, parathyroid gland, pineal gland, pituitary gland, carotid body, salivary gland, skin, gall bladder, pancreas, small intestine, stomach, spleen, spinal cord, thymus, thyroid gland, trachea, uterus, or vermiform appendix. Alternatively, the organ is an adrenal gland, appendix, brain, bladder, kidney, intestine, large intestine, small intestine, liver, heart, or muscle.

The term "optionally substituted" or "substituted" means that the referenced group substituted with one or more additional group(s). In certain embodiments, the one or more additional group(s) are individually and independently selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, amido. In one embodiment, the referenced group is substituted with one or more halogen. In another embodiment, the referenced group is substituted with one or more alkyl.

An "alkyl" group refers to an aliphatic hydrocarbon group. Reference to an alkyl group includes "saturated alkyl" and/or "unsaturated alkyl". The alkyl group, whether saturated or unsaturated, includes branched, straight chain, or cyclic groups. By way of example only, alkyl includes methyl, ethyl, propyl, iso-propyl, n-butyl, iso-butyl, sec-butyl, t-butyl, pentyl, iso-pentyl, neo-pentyl, and hexyl. In some embodiments, alkyl groups include, but are in no way limited to, methyl, ethyl, propyl, isopropyl, butyl, isobutyl, tertiary butyl, pentyl, hexyl, ethenyl, propenyl, butenyl, cyclopropyl, cyclobutyl, cyclopentyl, cyclohexyl, and the like. A "lower alkyl" is a $C_1$-$C_6$ alkyl. A "heteroalkyl" group substitutes any one of the carbons of the alkyl group with a heteroatom having the appropriate number of hydrogen atoms attached (e.g., a $CH_2$ group to an NH group or an O group).

An "alkoxy" group refers to a (alkyl)O— group, where alkyl is as defined herein.

The term "alkylamine" refers to the —N(alkyl)$_x$H$_y$ group, wherein alkyl is as defined herein and x and y are selected from the group x=1, y=1 and x=2, y=0. When x=2, the alkyl groups, taken together with the nitrogen to which they are attached, optionally form a cyclic ring system.

An "amide" is a chemical moiety with formula —C(O)NR$_2$ or —NRC(O)R, where each R is independently selected from hydrogen, alkyl, cycloalkyl, aryl, heteroaryl and heterocycloalkyl.

The term "ester" refers to a chemical moiety with formula —C(=O)OR, where R is selected from the group consisting of alkyl, cycloalkyl, aryl, heteroaryl and heterocycloalkyl.

As used herein, the term "aryl" refers to an aromatic ring wherein each of the atoms forming the ring is a carbon atom. Aryl rings described herein include rings having five, six, seven, eight, nine, or more than nine carbon atoms. Aryl groups are optionally substituted. Examples of aryl groups include, but are not limited to phenyl, and naphthalenyl.

The term "cycloalkyl" refers to a monocyclic or polycyclic non-aromatic radical, wherein each of the atoms forming the ring (i.e. skeletal atoms) is a carbon atom. In various embodiments, cycloalkyls are saturated, or partially unsaturated. In some embodiments, cycloalkyls are fused with an aromatic ring. Cycloalkyl groups include groups having from 3 to 10 ring atoms. Monocyclic cycloalkyls include, but are not limited to, cyclopropyl, cyclobutyl, cyclopentyl, cyclohexyl, cycloheptyl, and cyclooctyl. Dicylclic cycloalkyls include, but are not limited to tetrahydronaphthyl, indanyl, tetrahydropentalene or the like. Polycyclic cycloalkyls include adamantane, norbornane or the like. The term cycloalkyl includes "unsaturated nonaromatic carbocyclyl" or "nonaromatic unsaturated carbocyclyl" groups both of which refer to a nonaromatic carbocycle, as defined herein, that contains at least one carbon carbon double bond or one carbon carbon triple bond.

The term "heterocyclo" refers to heteroaromatic and heterocycloalkyl groups containing one to four ring heteroatoms each selected from O, S and N. In certain instances, each heterocyclic group has from 4 to 10 atoms in its ring system, and with the proviso that the ring of said group does not contain two adjacent O or S atoms. Non-aromatic heterocyclic groups include groups having 3 atoms in their ring system, but aromatic heterocyclic groups must have at least 5 atoms in their ring system. The heterocyclic groups include benzo-fused ring systems. An example of a 3-membered heterocyclic group is aziridinyl (derived from aziridine). An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The terms "heteroaryl" or, alternatively, "heteroaromatic" refers to an aryl group that includes one or more ring heteroatoms selected from nitrogen, oxygen and sulfur. An N-containing "heteroaromatic" or "heteroaryl" moiety refers to an aromatic group in which at least one of the skeletal atoms of the ring is a nitrogen atom. In certain embodiments, heteroaryl groups are monocyclic or polycyclic. Examples of monocyclic heteroaryl groups include and are not limited to pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. In some embodiments, a heteroaryl contains 0-3 N atoms in the ring. In some embodiments, a heteroaryl contains 1-3 N atoms in the ring. In some embodiments, a heteroaryl contains 0-3 N atoms, 0-1 O atoms, and 0-1 S atoms in the ring. In some embodiments, a heteroaryl is a monocyclic or bicyclic heteroaryl. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heteroalicyclic" group or "heterocycloalkyl" group or "heterocyclyl" group refers to a cycloalkyl group, wherein at least one skeletal ring atom is a heteroatom selected from nitrogen, oxygen and sulfur. In various embodiments, heterocycloalkyls are saturated, or partially unsaturated. In some embodiments, the radicals are fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heterocycloalkyl also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "halo" or, alternatively, "halogen" means fluoro, chloro, bromo and iodo.

The terms "haloalkyl," and "haloalkoxy" include alkyl and alkoxy structures that are substituted with one or more halogens. In embodiments, where more than one halogen is included in the group, the halogens are the same or they are different. The terms "fluoroalkyl" and "fluoroalkoxy" include haloalkyl and haloalkoxy groups, respectively, in which the halo is fluorine.

The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, —$CH_2$—O—$CH_3$, —$CH_2$—$CH_2$—O—$CH_3$, —$CH_2$—NH—$CH_3$, —$CH_2$—$CH_2$—NH—$CH_3$, —$CH_2$—N($CH_3$)—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. In some embodiments, up to two heteroatoms are consecutive, such as, by way of example, —$CH_2$—NH—$OCH_3$ and —$CH_2$—O—Si($CH_3$)$_3$.

A "cyano" group refers to a CN group.

An "isocyanato" group refers to a NCO group.

A "thiocyanato" group refers to a CNS group.

An "isothiocyanato" group refers to a NCS group.

"Alkoyloxy" refers to a RC(=O)O— group.

"Alkoyl" refers to a RC(=O)— group.

Compounds

For the Hedgehog signaling inhibitors described herein suitable for use in the methods also described herein, definitions of referred-to standard chemistry terms may be found in reference works (if not otherwise defined herein), including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, protein chemistry, biochemistry, recombinant DNA techniques and pharmacology, within the ordinary skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients.

Described herein are compounds of any of Formula (I), (Ia), (Ib), (II), (IIa), (III), (IIIa), (IV), or (IVa). Also described herein are pharmaceutically acceptable salts, and pharmaceutically acceptable solvates of such compounds. Pharmaceutical compositions that include at least one such compound or a pharmaceutically acceptable salt or solvate of such compound, are provided. In certain embodiments, isomers and chemically protected forms of compounds having a structure represented by any of Formula (I), (Ia), (Ib), (II), (IIa), (III), (IIIa), (IV), or (IVa) are also provided.

In some embodiments is a compound having the structure of Formula (I):

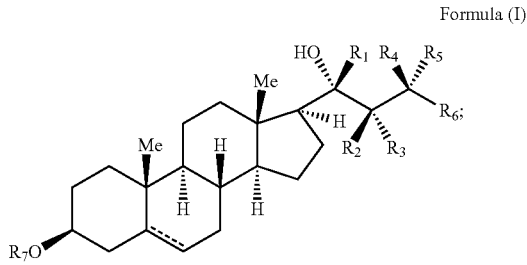

Formula (I)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- $R_6$ is substituted or unsubstituted aryl or substituted or unsubstituted heteroaryl;
- ===== is a single or double bond;
- $R_2$, $R_3$, $R_4$, and $R_5$ are independently hydrogen, deuterium, or —OH;
- $R_7$ is hydrogen, substituted or unsubstituted $C_1$-$C_8$alkyl, or —C(O)$NR_8R_9$; and
- $R_8$ and $R_9$ are independently hydrogen, substituted or unsubstituted $C_1$-$C_8$alkyl, or substituted or unsubstituted aryl.

In some embodiments is a compound of Formula (I) wherein ===== is a single bond. In some embodiments is a compound of Formula (I) wherein ===== is a double bond.

In some embodiments is a compound of Formula (I), wherein $R_6$ is substituted or unsubstituted aryl. In some embodiments is a compound of Formula (I), wherein $R_6$ is substituted or unsubstituted phenyl. In some embodiments is a compound of Formula (I), wherein $R_6$ is unsubstituted phenyl. In some embodiments is a compound of Formula (I), wherein $R_6$ is substituted phenyl. In some embodiments is a compound of Formula (I), wherein $R_6$ is phenyl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a compound of Formula (I), wherein $R_6$ is phenyl substituted with at least one substituent selected from alkyl, hydroxy, alkoxy, halogen, and haloalkyl. In some embodiments is a compound of Formula (I), wherein $R_6$ is phenyl substituted with at least one halogen substituent. In some embodiments is a compound of Formula (I), wherein $R_6$ is phenyl substituted with at least one fluoro substituent. In some embodiments is a compound of Formula (I), wherein $R_6$ is 4-fluorophenyl.

In some embodiments is a compound of Formula (I), wherein $R_6$ is substituted or unsubstituted heteroaryl. In some embodiments is a compound of Formula (I), wherein $R_6$ is unsubstituted heteroaryl. In some embodiments is a compound of Formula (I), wherein $R_6$ is substituted heteroaryl. In some embodiments is a compound of Formula (I), wherein $R_6$ is heteroaryl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkylamino, dialkyl-amino, and amido. In some embodiments is a compound of Formula (I), wherein $R_6$ is heteroaryl substituted with at least one substituent selected from alkyl, hydroxy, alkoxy, halogen, and haloalkyl. In some embodiments is a compound of Formula (I), wherein $R_6$ is heteroaryl substituted with at least one halogen substituent. In some embodiments is a compound of Formula (I), wherein $R_6$ is a heteroaryl selected from thienyl, furyl, thiadiazolyl, benzothiadiazolyl, pyrrolyl, imidazolyl, oxazolyl, pyrazolyl, isothiazolyl, isoxazolyl, pyridyl, pyrazinyl, pyrimidinyl, pyridazinyl, pyrazolo-pyrimidinyl, triazolo-pyrimidinyl, and imidazo-pyrimidinyl.

In some embodiments is a compound of Formula (I), wherein $R_2$, $R_3$, $R_4$, and $R_5$ are independently hydrogen or deuterium. In some embodiments is a compound of Formula (I), wherein $R_2$, $R_3$, $R_4$, and $R_5$ are each deuterium. In some embodiments is a compound of Formula (I), wherein $R_2$, $R_3$, $R_4$, and $R_5$ are each hydrogen. In some embodiments is a compound of Formula (I), wherein $R_2$ is —OH, and $R_3$, $R_4$, and $R_5$ are each hydrogen. In some embodiments is a compound of Formula (I), wherein $R_3$ is —OH, and $R_2$, $R_4$, and $R_5$ are each hydrogen. In some embodiments is a compound of Formula (I), wherein $R_2$ and $R_4$ are each —OH, and $R_3$ and $R_5$ are each hydrogen. In some embodiments is a compound of Formula (I), wherein $R_2$ and $R_5$ are each —OH, and $R_3$ and $R_4$ are each hydrogen. In some embodiments is a compound of Formula (I), wherein $R_3$ and $R_4$ are each —OH, and $R_2$ and $R_5$ are each hydrogen. In some embodiments is a compound of Formula (I), wherein $R_3$ and $R_5$ are each —OH, and $R_2$ and $R_4$ are each hydrogen.

In some embodiments is a compound of Formula (I), wherein $R_1$ is substituted or unsubstituted $C_1$-$C_8$alkyl. In some embodiments is a compound of Formula (I), wherein $R_1$ is substituted $C_1$-$C_8$alkyl. In some embodiments is a compound of Formula (I), wherein $R_1$ is —$CF_3$. In some embodiments is a compound of Formula (I), wherein $R_1$ is unsubstituted $C_1$-$C_8$alkyl. In some embodiments is a compound of Formula (I), wherein $R_1$ is unsubstituted $C_1$-$C_4$alkyl. In some embodiments is a compound of Formula (I), wherein $R_1$ is —$CH_3$. In some embodiments is a compound of Formula (I), wherein $R_1$ is —$CH_2CH_3$. In some embodiments is a compound of Formula (I), wherein $R_1$ is substituted or unsubstituted aryl. In some embodiments is a compound of Formula (I), wherein $R_1$ is unsubstituted phenyl. In some embodiments is a compound of Formula (I), wherein $R_1$ is substituted or unsubstituted $C_1$-$C_8$alkyl or substituted or unsubstituted phenyl.

In some embodiments is a compound of Formula (I), wherein $R_7$ is hydrogen or substituted or unsubstituted $C_1$-$C_8$alkyl. In some embodiments is a compound of Formula (I), wherein $R_7$ is hydrogen. In some embodiments is a compound of Formula (I), wherein $R_7$ is substituted or unsubstituted $C_1$-$C_8$alkyl. In some embodiments is a compound of Formula (I), wherein $R_7$ is unsubstituted $C_1$-$C_8$alkyl. In some embodiments is a compound of Formula (I), wherein $R_7$ is —$CH_3$. In some embodiments is a compound of Formula (I), wherein $R_7$ is —C(O)$NR_8R_9$. In some embodiments is a compound of Formula (I), wherein $R_7$ is substituted or unsubstituted $C_1$-$C_8$alkyl. In some embodiments is a compound of Formula (I), wherein $R_7$ is —C(O)$NR_8R_9$, and $R_8$ and $R_9$ are independently substituted or unsubstituted $C_1$-$C_8$alkyl. In some embodiments is a compound of Formula (I), wherein $R_7$ is —C(O)$NR_8R_9$, and $R_8$ and $R_9$ are each —$CH_3$. In some embodiments is a compound of Formula (I), wherein $R_7$ is —C(O)$NR_8R_9$, $R_8$ is hydrogen, and $R_9$ is substituted or unsubstituted $C_1$-$C_8$alkyl. In some embodiments is a compound of Formula (I), wherein $R_7$ is —C(O)$NR_8R_9$, $R_8$ is hydrogen, and $R_9$ is —$CH_3$. In some embodiments is a compound of Formula (I), wherein $R_7$ is —C(O)$NR_8R_9$, $R_8$ is substituted or unsubstituted aryl, and $R_9$ is substituted or unsubstituted $C_1$-$C_8$alkyl. In some embodiments is a compound of Formula (I), wherein $R_7$ is —C(O)$NR_8R_9$, $R_8$ is substituted or unsubstituted aryl, and $R_9$ is hydrogen.

In some embodiments is a compound having the structure of Formula (Ia):

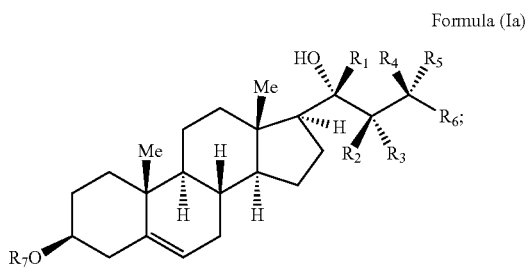

Formula (Ia)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- $R_6$ is substituted or unsubstituted aryl or substituted or unsubstituted heteroaryl;
- $R_2$, $R_3$, $R_4$, and $R_5$ are independently hydrogen, deuterium, or —OH;
- $R_7$ is hydrogen, substituted or unsubstituted $C_1$-$C_8$alkyl, or —C(O)$NR_8R_9$; and
- $R_8$ and $R_9$ are independently hydrogen, substituted or unsubstituted $C_1$-$C_8$alkyl, or substituted or unsubstituted aryl.

In some embodiments is a compound of Formula (Ia), wherein $R_6$ is substituted or unsubstituted aryl. In some embodiments is a compound of Formula (Ia), wherein $R_6$ is substituted or unsubstituted phenyl. In some embodiments is a compound of Formula (Ia), wherein $R_6$ is unsubstituted phenyl. In some embodiments is a compound of Formula (Ia), wherein $R_6$ is substituted phenyl. In some embodiments is a compound of Formula (Ia), wherein $R_6$ is phenyl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a compound of Formula (Ia), wherein $R_6$ is phenyl substituted with at least one substituent selected from alkyl, hydroxy, alkoxy, halogen, and haloalkyl. In some embodiments is a compound of Formula (Ia), wherein $R_6$ is phenyl substituted with at least one halogen substituent. In some embodiments is a compound of Formula (Ia), wherein $R_6$ is phenyl substituted with at least one fluoro substituent.

In some embodiments is a compound of Formula (Ia), wherein $R_6$ is substituted or unsubstituted heteroaryl. In some embodiments is a compound of Formula (Ia), wherein $R_6$ is unsubstituted heteroaryl. In some embodiments is a compound of Formula (Ia), wherein $R_6$ is substituted heteroaryl. In some embodiments is a compound of Formula (Ia), wherein $R_6$ is heteroaryl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkylamino, dialkyl-amino, and amido. In some embodiments is a compound of Formula (Ia), wherein $R_6$ is heteroaryl substituted with at least one substituent selected from alkyl, hydroxy, alkoxy, halogen, and haloalkyl. In some embodiments is a compound of Formula (Ia), wherein $R_6$ is heteroaryl substituted with at least one halogen substituent. In some embodiments is a compound of Formula (Ia), wherein $R_6$ is a heteroaryl selected from thienyl, furyl, thiadiazolyl, benzothiadiazolyl, pyrrolyl, imidazolyl, oxazolyl, pyrazolyl, isothiazolyl, isoxazolyl, pyridyl, pyrazinyl, pyrimidinyl, pyridazinyl, pyrazolo-pyrimidinyl, triazolo-pyrimidinyl, and imidazo-pyrimidinyl.

In some embodiments is a compound of Formula (Ia), wherein $R_2$, $R_3$, $R_4$, and $R_5$ are each deuterium. In some embodiments is a compound of Formula (Ia), wherein $R_2$, $R_3$, $R_4$, and $R_5$ are each hydrogen. In some embodiments is a compound of Formula (Ia), wherein $R_2$ is —OH, and $R_3$, $R_4$, and $R_5$ are each hydrogen. In some embodiments is a compound of Formula (Ia), wherein $R_3$ is —OH, and $R_2$, $R_4$, and $R_5$ are each hydrogen. In some embodiments is a compound of Formula (Ia), wherein $R_2$ and $R_4$ are each —OH, and $R_3$ and $R_5$ are each hydrogen. In some embodiments is a compound of Formula (Ia), wherein $R_2$ and $R_5$ are each —OH, and $R_3$ and $R_4$ are each hydrogen. In some embodiments is a compound of Formula (Ia), wherein $R_3$ and $R_4$ are each —OH, and $R_2$ and $R_5$ are each hydrogen. In some embodiments is a compound of Formula (Ia), wherein $R_3$ and $R_5$ are each —OH, and $R_2$ and $R_4$ are each hydrogen.

In some embodiments is a compound of Formula (Ia), wherein $R_1$ is substituted or unsubstituted $C_1$-$C_8$alkyl. In some embodiments is a compound of Formula (Ia), wherein $R_1$ is substituted $C_1$-$C_8$alkyl. In some embodiments is a compound of Formula (Ia), wherein $R_1$ is —$CF_3$. In some embodiments is a compound of Formula (Ia), wherein $R_1$ is unsubstituted $C_1$-$C_8$alkyl. In some embodiments is a compound of Formula (Ia), wherein $R_1$ is —$CH_3$. In some embodiments is a compound of Formula (Ia), wherein $R_1$ is —$CH_2CH_3$. In some embodiments is a compound of Formula (Ia), wherein $R_1$ is substituted or unsubstituted aryl. In some embodiments is a compound of Formula (Ia), wherein $R_1$ is unsubstituted phenyl.

In some embodiments is a compound of Formula (Ia), wherein $R_7$ is hydrogen. In some embodiments is a compound of Formula (Ia), wherein $R_7$ is substituted or unsubstituted $C_1$-$C_8$alkyl. In some embodiments is a compound of Formula (Ia), wherein $R_7$ is —$CH_3$. In some embodiments is a compound of Formula (Ia), wherein $R_7$ is —C(O)$NR_8R_9$. In some embodiments is a compound of Formula (Ia), wherein $R_7$ is substituted or unsubstituted $C_1$-$C_8$alkyl. In some embodiments is a compound of Formula (Ia), wherein $R_7$ is —C(O)$NR_8R_9$, and $R_8$ and $R_9$ are independently substituted or unsubstituted $C_1$-$C_8$alkyl. In some embodiments is a compound of Formula (Ia), wherein $R_7$ is —C(O)$NR_8R_9$, and $R_8$ and $R_9$ are each —$CH_3$. In some embodiments is a compound of Formula (Ia), wherein $R_7$ is —C(O)NR$_8$R$_9$, $R_8$ is hydrogen, and $R_9$ is substituted or unsubstituted $C_1$-$C_8$alkyl. In some embodiments is a compound of Formula (Ia), wherein $R_7$ is —C(O)NR$_8$R$_9$, $R_8$ is hydrogen, and $R_9$ is —CH$_3$. In some embodiments is a compound of Formula (Ia), wherein $R_7$ is —C(O)NR$_8$R$_9$, $R_8$ is substituted or unsubstituted aryl, and $R_9$ is substituted or unsubstituted $C_1$-$C_8$alkyl. In some embodiments is a compound of Formula (Ia), wherein $R_7$ is —C(O)NR$_8$R$_9$, $R_8$ is substituted or unsubstituted aryl, and $R_9$ is hydrogen.

In some embodiments is a compound having the structure of Formula (Ib):

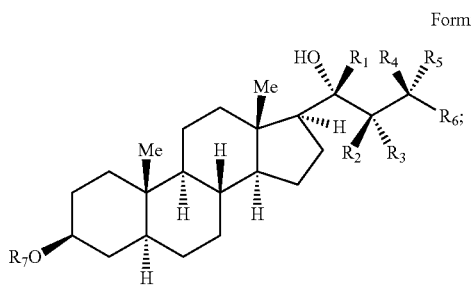

Formula (Ib)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- $R_6$ is substituted or unsubstituted aryl or substituted or unsubstituted heteroaryl;
- $R_2$, $R_3$, $R_4$, and $R_5$ are independently hydrogen, deuterium, or —OH;
- $R_7$ is hydrogen, substituted or unsubstituted $C_1$-$C_8$alkyl, or —C(O)NR$_8$R$_9$; and
- $R_8$ and $R_9$ are independently hydrogen, substituted or unsubstituted $C_1$-$C_8$alkyl, or substituted or unsubstituted aryl.

In some embodiments is a compound of Formula (Ib), wherein $R_6$ is substituted or unsubstituted aryl. In some embodiments is a compound of Formula (Ib), wherein $R_6$ is substituted or unsubstituted phenyl. In some embodiments is a compound of Formula (Ib), wherein $R_6$ is unsubstituted phenyl. In some embodiments is a compound of Formula (Ib), wherein $R_6$ is substituted phenyl. In some embodiments is a compound of Formula (Ib), wherein $R_6$ is phenyl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a compound of Formula (Ib), wherein $R_6$ is phenyl substituted with at least one substituent selected from alkyl, hydroxy, alkoxy, halogen, and haloalkyl. In some embodiments is a compound of Formula (Ib), wherein $R_6$ is phenyl substituted with at least one halogen substituent. In some embodiments is a compound of Formula (Ib), wherein $R_6$ is phenyl substituted with at least one fluoro substituent.

In some embodiments is a compound of Formula (Ib), wherein $R_6$ is substituted or unsubstituted heteroaryl. In some embodiments is a compound of Formula (Ib), wherein $R_6$ is unsubstituted heteroaryl. In some embodiments is a compound of Formula (Ib), wherein $R_6$ is substituted heteroaryl. In some embodiments is a compound of Formula (Ib), wherein $R_6$ is heteroaryl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a compound of Formula (Ib), wherein $R_6$ is heteroaryl substituted with at least one substituent selected from alkyl, hydroxy, alkoxy, halogen, and haloalkyl. In some embodiments is a compound of Formula (Ib), wherein $R_6$ is heteroaryl substituted with at least one halogen substituent. In some embodiments is a compound of Formula (Ib), wherein $R_6$ is a heteroaryl selected from thienyl, furyl, thiadiazolyl, benzothiadiazolyl, pyrrolyl, imidazolyl, oxazolyl, pyrazolyl, isothiazolyl, isoxazolyl, pyridyl, pyrazinyl, pyrimidinyl, pyridazinyl, pyrazolo-pyrimidinyl, triazolo-pyrimidinyl, and imidazo-pyrimidinyl.

In some embodiments is a compound of Formula (Ib), wherein $R_2$, $R_3$, $R_4$, and $R_5$ are each deuterium. In some embodiments is a compound of Formula (Ib), wherein $R_2$, $R_3$, $R_4$, and $R_5$ are each hydrogen. In some embodiments is a compound of Formula (Ib), wherein $R_2$ is —OH, and $R_3$, $R_4$, and $R_5$ are each hydrogen. In some embodiments is a compound of Formula (Ib), wherein $R_3$ is —OH, and $R_2$, $R_4$, and $R_5$ are each hydrogen. In some embodiments is a compound of Formula (Ib), wherein $R_2$ and $R_4$ are each —OH, and $R_3$ and $R_5$ are each hydrogen. In some embodiments is a compound of Formula (Ib), wherein $R_2$ and $R_5$ are each —OH, and $R_3$ and $R_4$ are each hydrogen. In some embodiments is a compound of Formula (Ib), wherein $R_3$ and $R_4$ are each —OH, and $R_2$ and $R_5$ are each hydrogen. In some embodiments is a compound of Formula (Ib), wherein $R_3$ and $R_5$ are each —OH, and $R_2$ and $R_4$ are each hydrogen.

In some embodiments is a compound of Formula (Ib), wherein $R_1$ is substituted or unsubstituted $C_1$-$C_8$alkyl. In some embodiments is a compound of Formula (Ib), wherein $R_1$ is substituted $C_1$-$C_8$alkyl. In some embodiments is a compound of Formula (Ib), wherein $R_1$ is —CF$_3$. In some embodiments is a compound of Formula (Ib), wherein $R_1$ is unsubstituted $C_1$-$C_8$alkyl. In some embodiments is a compound of Formula (Ib), wherein $R_1$ is —CH$_3$. In some embodiments is a compound of Formula (Ib), wherein $R_1$ is —CH$_2$CH$_3$. In some embodiments is a compound of Formula (Ib), wherein $R_1$ is substituted or unsubstituted aryl. In some embodiments is a compound of Formula (Ib), wherein $R_1$ is unsubstituted phenyl.

In some embodiments is a compound of Formula (Ib), wherein $R_7$ is hydrogen. In some embodiments is a compound of Formula (Ib), wherein $R_7$ is substituted or unsubstituted $C_1$-$C_8$alkyl. In some embodiments is a compound of Formula (Ib), wherein $R_7$ is —CH$_3$. In some embodiments is a compound of Formula (Ib), wherein $R_7$ is —C(O)NR$_8$R$_9$. In some embodiments is a compound of Formula (Ib), wherein $R_7$ is substituted or unsubstituted $C_1$-$C_8$alkyl. In some embodiments is a compound of Formula (Ib), wherein $R_7$ is —C(O)NR$_8$R$_9$, and $R_8$ and $R_9$ are independently substituted or unsubstituted $C_1$-$C_8$alkyl. In some embodiments is a compound of Formula (Ib), wherein $R_7$ is —C(O)NR$_8$R$_9$, and $R_8$ and $R_9$ are each —CH$_3$. In some embodiments is a compound of Formula (Ib), wherein $R_7$ is —C(O)NR$_8$R$_9$, $R_8$ is hydrogen, and $R_9$ is substituted or unsubstituted $C_1$-$C_8$alkyl. In some embodiments is a compound of Formula (Ib), wherein $R_7$ is —C(O)NR$_8$R$_9$, $R_8$ is hydrogen, and $R_9$ is —$CH_3$. In some embodiments is a compound of Formula (Ib), wherein $R_7$ is —$C(O)NR_8R_9$, $R_8$ is substituted or unsubstituted aryl, and $R_9$ is substituted or unsubstituted $C_1$-$C_8$alkyl. In some embodiments is a compound of Formula (Ib), wherein $R_7$ is —$C(O)NR_8R_9$, $R_8$ is substituted or unsubstituted aryl, and $R_9$ is hydrogen.

In some embodiments is a compound having the structure of Formula (II):

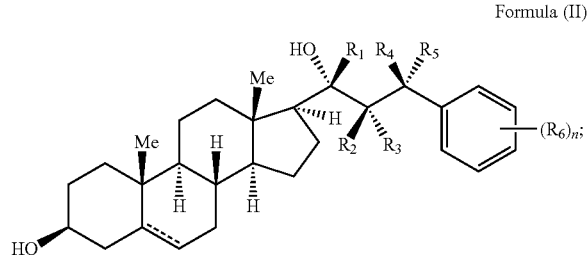

Formula (II)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
- ====== is a single or double bond;
- $R_2$, $R_3$, $R_4$, and $R_5$ are independently hydrogen, deuterium, or —OH; and
- n is 0, 1, 2, or 3.

In some embodiments is a compound of Formula (II) wherein ====== is a single bond. In some embodiments is a compound of Formula (II) wherein ====== is a double bond.

In some embodiments is a compound of Formula (II), wherein n is 0. In some embodiments is a compound of Formula (II), wherein n is 1 and $R_6$ is halogen. In some embodiments is a compound of Formula (II), wherein n is 1 and $R_6$ is F. In some embodiments is a compound of Formula (II), wherein n is 1 and $R_6$ is Cl. In some embodiments is a compound of Formula (II), wherein n is 1 and $R_6$ is Br. In some embodiments is a compound of Formula (II), wherein n is 1 and $R_6$ is hydroxy. In some embodiments is a compound of Formula (II), wherein n is 1 and $R_6$ is substituted or unsubstituted $C_1$-$C_8$alkyl. In some embodiments is a compound of Formula (II), wherein n is 1 and $R_6$ is unsubstituted $C_1$-$C_8$alkyl. In some embodiments is a compound of Formula (II), wherein n is 1 and $R_6$ is substituted or unsubstituted $C_1$-$C_8$alkoxy. In some embodiments is a compound of Formula (II), wherein n is 2 and each $R_6$ is halogen. In some embodiments is a compound of Formula (II), wherein n is 2 and each $R_6$ is F. In some embodiments is a compound of Formula (II), wherein n is 2 and each $R_6$ is Cl. In some embodiments is a compound of Formula (II), wherein n is 2 and each $R_6$ is Br. In some embodiments is a compound of Formula (II), wherein n is 2 and one $R_6$ is halogen and one $R_6$ is hydroxy. In some embodiments is a compound of Formula (II), wherein n is 2 and each $R_6$ is hydroxy. In some embodiments is a compound of Formula (II), wherein n is 2 and one $R_6$ is halogen and one $R_6$ is substituted or unsubstituted $C_1$-$C_8$alkyl. In some embodiments is a compound of Formula (II), wherein n is 2 and each $R_6$ is substituted or unsubstituted $C_1$-$C_8$alkyl. In some embodiments is a compound of Formula (II), wherein n is 2 and each $R_6$ is unsubstituted $C_1$-$C_8$alkyl. In some embodiments is a compound of Formula (II), wherein n is 2 and one $R_6$ is halogen and one $R_6$ is substituted or unsubstituted $C_1$-$C_8$alkoxy. In some embodiments is a compound of Formula (II), wherein n is 2 and each $R_6$ is substituted or unsubstituted $C_1$-$C_8$alkoxy.

In some embodiments is a compound of Formula (II), wherein $R_2$, $R_3$, $R_4$, and $R_5$ are each deuterium. In some embodiments is a compound of Formula (II), wherein $R_2$, $R_3$, $R_4$, and $R_5$ are each hydrogen. In some embodiments is a compound of Formula (II), wherein $R_2$ is —OH, and $R_3$, $R_4$, and $R_5$ are each hydrogen. In some embodiments is a compound of Formula (II), wherein $R_3$ is —OH, and $R_2$, $R_4$, and $R_5$ are each hydrogen. In some embodiments is a compound of Formula (II), wherein $R_2$ and $R_4$ are each —OH, and $R_3$ and $R_5$ are each hydrogen. In some embodiments is a compound of Formula (II), wherein $R_2$ and $R_5$ are each —OH, and $R_3$ and $R_4$ are each hydrogen. In some embodiments is a compound of Formula (II), wherein $R_3$ and $R_4$ are each —OH, and $R_2$ and $R_5$ are each hydrogen. In some embodiments is a compound of Formula (II), wherein $R_3$ and $R_5$ are each —OH, and $R_2$ and $R_4$ are each hydrogen.

In some embodiments is a compound of Formula (II), wherein $R_1$ is substituted or unsubstituted $C_1$-$C_8$alkyl. In some embodiments is a compound of Formula (II), wherein $R_1$ is substituted $C_1$-$C_8$alkyl. In some embodiments is a compound of Formula (II), wherein $R_1$ is —$CF_3$. In some embodiments is a compound of Formula (II), wherein $R_1$ is unsubstituted $C_1$-$C_8$alkyl. In some embodiments is a compound of Formula (II), wherein $R_1$ is —$CH_3$. In some embodiments is a compound of Formula (II), wherein $R_1$ is —$CH_2CH_3$. In some embodiments is a compound of Formula (II), wherein $R_1$ is substituted or unsubstituted aryl. In some embodiments is a compound of Formula (II), wherein $R_1$ is unsubstituted phenyl.

In some embodiments is a compound having the structure of Formula (IIa):

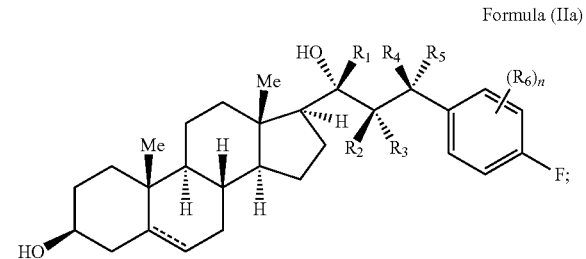

Formula (IIa)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted C$_3$-C$_8$cycloalkyl, substituted or unsubstituted aryl, or substituted or unsubstituted heteroaryl;

===== is a single or double bond;

R$_2$, R$_3$, R$_4$, and R$_5$ are independently hydrogen, deuterium, or —OH; and n is 0, 1, or 2.

In some embodiments is a compound of Formula (IIa) wherein ===== is a single bond. In some embodiments is a compound of Formula (IIa) wherein ===== is a double bond.

In some embodiments is a compound of Formula (IIa), wherein n is 0. In some embodiments is a compound of Formula (IIa), wherein n is 1 and R$_6$ is halogen. In some embodiments is a compound of Formula (IIa), wherein n is 1 and R$_6$ is F. In some embodiments is a compound of Formula (IIa), wherein n is 1 and R$_6$ is Cl. In some embodiments is a compound of Formula (IIa), wherein n is 1 and R$_6$ is Br. In some embodiments is a compound of Formula (IIa), wherein n is 1 and R$_6$ is hydroxy. In some embodiments is a compound of Formula (IIa), wherein n is 1 and R$_6$ is substituted or unsubstituted C$_1$-C$_8$alkyl. In some embodiments is a compound of Formula (IIa), wherein n is 1 and R$_6$ is unsubstituted C$_1$-C$_8$alkyl. In some embodiments is a compound of Formula (IIa), wherein n is 1 and R$_6$ is substituted or unsubstituted C$_1$-C$_8$alkoxy. In some embodiments is a compound of Formula (IIa), wherein n is 2 and each R$_6$ is halogen. In some embodiments is a compound of Formula (IIa), wherein n is 2 and each R$_6$ is F. In some embodiments is a compound of Formula (IIa), wherein n is 2 and each R$_6$ is Cl. In some embodiments is a compound of Formula (IIa), wherein n is 2 and each R$_6$ is Br. In some embodiments is a compound of Formula (IIa), wherein n is 2 and one R$_6$ is halogen and one R$_6$ is hydroxy. In some embodiments is a compound of Formula (IIa), wherein n is 2 and each R$_6$ is hydroxy. In some embodiments is a compound of Formula (IIa), wherein n is 2 and one R$_6$ is halogen and one R$_6$ is substituted or unsubstituted C$_1$-C$_8$alkyl. In some embodiments is a compound of Formula (IIa), wherein n is 2 and each R$_6$ is substituted or unsubstituted C$_1$-C$_8$alkyl. In some embodiments is a compound of Formula (IIa), wherein n is 2 and each R$_6$ is unsubstituted C$_1$-C$_8$alkyl. In some embodiments is a compound of Formula (IIa), wherein n is 2 and one R$_6$ is halogen and one R$_6$ is substituted or unsubstituted C$_1$-C$_8$alkoxy. In some embodiments is a compound of Formula (IIa), wherein n is 2 and each R$_6$ is substituted or unsubstituted C$_1$-C$_8$alkoxy.

In some embodiments is a compound of Formula (IIa), wherein R$_2$, R$_3$, R$_4$, and R$_5$ are each deuterium. In some embodiments is a compound of Formula (IIa), wherein R$_2$, R$_3$, R$_4$, and R$_5$ are each hydrogen. In some embodiments is a compound of Formula (IIa), wherein R$_2$ is —OH, and R$_3$, R$_4$, and R$_5$ are each hydrogen. In some embodiments is a compound of Formula (IIa), wherein R$_3$ is —OH, and R$_2$, R$_4$, and R$_5$ are each hydrogen. In some embodiments is a compound of Formula (IIa), wherein R$_2$ and R$_4$ are each —OH, and R$_3$ and R$_5$ are each hydrogen. In some embodiments is a compound of Formula (IIa), wherein R$_2$ and R$_5$ are each —OH, and R$_3$ and R$_4$ are each hydrogen. In some embodiments is a compound of Formula (IIa), wherein R$_3$ and R$_4$ are each —OH, and R$_2$ and R$_5$ are each hydrogen. In some embodiments is a compound of Formula (IIa), wherein R$_3$ and R$_5$ are each —OH, and R$_2$ and R$_4$ are each hydrogen.

In some embodiments is a compound of Formula (IIa), wherein R$_1$ is substituted or unsubstituted C$_1$-C$_8$alkyl. In some embodiments is a compound of Formula (IIa), wherein R$_1$ is substituted C$_1$-C$_8$alkyl. In some embodiments is a compound of Formula (IIa), wherein R$_1$ is —CF$_3$. In some embodiments is a compound of Formula (IIa), wherein R$_1$ is unsubstituted C$_1$-C$_8$alkyl. In some embodiments is a compound of Formula (IIa), wherein R$_1$ is —CH$_3$. In some embodiments is a compound of Formula (IIa), wherein R$_1$ is —CH$_2$CH$_3$. In some embodiments is a compound of Formula (IIa), wherein R$_1$ is substituted or unsubstituted aryl. In some embodiments is a compound of Formula (IIa), wherein R$_1$ is unsubstituted phenyl.

In some embodiments is a compound having the structure of Formula (III):

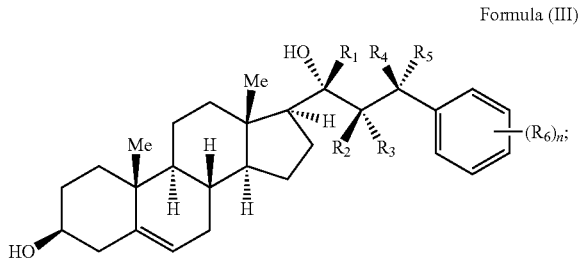

Formula (III)

wherein:

R$_1$ is substituted or unsubstituted C$_1$-C$_8$alkyl, substituted or unsubstituted C$_1$-C$_8$alkenyl, substituted or unsubstituted C$_1$-C$_8$alkynyl, substituted or unsubstituted aryl, substituted or unsubstituted heteroaryl, or substituted or unsubstituted —C$_1$-C$_4$alkylaryl;

each R$_6$ is independently halogen, hydroxy, substituted or unsubstituted C$_1$-C$_8$alkyl, substituted or unsubstituted C$_1$-C$_8$alkoxy, substituted or unsubstituted C$_1$-C$_8$heteroalkyl, substituted or unsubstituted C$_3$-C$_8$cycloalkyl, substituted or unsubstituted aryl, or substituted or unsubstituted heteroaryl;

R$_2$, R$_3$, R$_4$, and R$_5$ are independently hydrogen, deuterium, or —OH; and n is 0, 1, 2, or 3.

In some embodiments is a compound of Formula (III), wherein n is 0. In some embodiments is a compound of Formula (III), wherein n is 1 and R$_6$ is halogen. In some embodiments is a compound of Formula (III), wherein n is 1 and R$_6$ is F. In some embodiments is a compound of Formula (III), wherein n is 1 and R$_6$ is Cl. In some embodiments is a compound of Formula (III), wherein n is 1 and R$_6$ is Br. In some embodiments is a compound of Formula (III), wherein n is 1 and R$_6$ is hydroxy. In some embodiments is a compound of Formula (III), wherein n is 1 and R$_6$ is substituted or unsubstituted C$_1$-C$_8$alkyl. In some embodiments is a compound of Formula (III), wherein n is 1 and R$_6$ is unsubstituted C$_1$-C$_8$alkyl. In some embodiments is a compound of Formula (III), wherein n is 1 and R$_6$ is substituted or unsubstituted C$_1$-C$_8$alkoxy. In some embodiments is a compound of Formula (III), wherein n is 2 and each R$_6$ is halogen. In some embodiments is a compound of Formula (III), wherein n is 2 and each R$_6$ is F. In some embodiments is a compound of Formula (III), wherein n is 2 and each R$_6$ is Cl. In some embodiments is a compound of Formula (III), wherein n is 2 and each R$_6$ is Br. In some embodiments is a compound of Formula (III), wherein n is 2 and one R$_6$ is halogen and one R$_6$ is hydroxy. In some embodiments is a compound of Formula (III), wherein n is 2 and each R$_6$ is hydroxy. In some embodiments is a compound of Formula (III), wherein n is 2 and one R$_6$ is halogen and one R$_6$ is substituted or unsubstituted $C_1$-$C_8$alkyl. In some embodiments is a compound of Formula (III), wherein n is 2 and each $R_6$ is substituted or unsubstituted $C_1$-$C_8$alkyl. In some embodiments is a compound of Formula (III), wherein n is 2 and each $R_6$ is unsubstituted $C_1$-$C_8$alkyl. In some embodiments is a compound of Formula (III), wherein n is 2 and one $R_6$ is halogen and one $R_6$ is substituted or unsubstituted $C_1$-$C_8$alkoxy. In some embodiments is a compound of Formula (III), wherein n is 2 and each $R_6$ is substituted or unsubstituted $C_1$-$C_8$alkoxy.

In some embodiments is a compound of Formula (III), wherein $R_2$, $R_3$, $R_4$, and $R_5$ are each deuterium. In some embodiments is a compound of Formula (III), wherein $R_2$, $R_3$, $R_4$, and $R_5$ are each hydrogen. In some embodiments is a compound of Formula (III), wherein $R_2$ is —OH, and $R_3$, $R_4$, and $R_5$ are each hydrogen. In some embodiments is a compound of Formula (III), wherein $R_3$ is —OH, and $R_2$, $R_4$, and $R_5$ are each hydrogen. In some embodiments is a compound of Formula (III), wherein $R_2$ and $R_4$ are each —OH, and $R_3$ and $R_5$ are each hydrogen. In some embodiments is a compound of Formula (III), wherein $R_2$ and $R_5$ are each —OH, and $R_3$ and $R_4$ are each hydrogen. In some embodiments is a compound of Formula (III), wherein $R_3$ and $R_4$ are each —OH, and $R_2$ and $R_5$ are each hydrogen. In some embodiments is a compound of Formula (III), wherein $R_3$ and $R_5$ are each —OH, and $R_2$ and $R_4$ are each hydrogen.

In some embodiments is a compound of Formula (III), wherein $R_1$ is substituted or unsubstituted $C_1$-$C_8$alkyl. In some embodiments is a compound of Formula (III), wherein $R_1$ is substituted $C_1$-$C_8$alkyl. In some embodiments is a compound of Formula (III), wherein $R_1$ is —$CF_3$. In some embodiments is a compound of Formula (III), wherein $R_1$ is unsubstituted $C_1$-$C_8$alkyl. In some embodiments is a compound of Formula (III), wherein $R_1$ is —$CH_3$. In some embodiments is a compound of Formula (III), wherein $R_1$ is —$CH_2CH_3$. In some embodiments is a compound of Formula (III), wherein $R_1$ is substituted or unsubstituted aryl. In some embodiments is a compound of Formula (III), wherein $R_1$ is unsubstituted phenyl.

In some embodiments is a compound having the structure of Formula (IIIa):

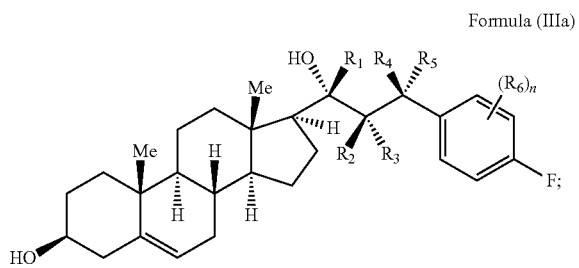

Formula (IIIa)

wherein:
  $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
  each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
  $R_2$, $R_3$, $R_4$, and $R_5$ are independently hydrogen, deuterium, or —OH; and
  n is 0, 1, or 2.

In some embodiments is a compound of Formula (IIIa), wherein n is 0. In some embodiments is a compound of Formula (IIIa), wherein n is 1 and $R_6$ is halogen. In some embodiments is a compound of Formula (IIIa), wherein n is 1 and $R_6$ is F. In some embodiments is a compound of Formula (IIIa), wherein n is 1 and $R_6$ is Cl. In some embodiments is a compound of Formula (IIIa), wherein n is 1 and $R_6$ is Br. In some embodiments is a compound of Formula (IIIa), wherein n is 1 and $R_6$ is hydroxy. In some embodiments is a compound of Formula (IIIa), wherein n is 1 and $R_6$ is substituted or unsubstituted $C_1$-$C_8$alkyl. In some embodiments is a compound of Formula (IIIa), wherein n is 1 and $R_6$ is unsubstituted $C_1$-$C_8$alkyl. In some embodiments is a compound of Formula (IIIa), wherein n is 1 and $R_6$ is substituted or unsubstituted $C_1$-$C_8$alkoxy. In some embodiments is a compound of Formula (IIIa), wherein n is 2 and each $R_6$ is halogen. In some embodiments is a compound of Formula (IIIa), wherein n is 2 and each $R_6$ is F. In some embodiments is a compound of Formula (IIIa), wherein n is 2 and each $R_6$ is Cl. In some embodiments is a compound of Formula (IIIa), wherein n is 2 and each $R_6$ is Br. In some embodiments is a compound of Formula (IIIa), wherein n is 2 and one $R_6$ is halogen and one $R_6$ is hydroxy. In some embodiments is a compound of Formula (IIIa), wherein n is 2 and each $R_6$ is hydroxy. In some embodiments is a compound of Formula (IIIa), wherein n is 2 and one $R_6$ is halogen and one $R_6$ is substituted or unsubstituted $C_1$-$C_8$alkyl. In some embodiments is a compound of Formula (IIIa), wherein n is 2 and each $R_6$ is substituted or unsubstituted $C_1$-$C_8$alkyl. In some embodiments is a compound of Formula (IIIa), wherein n is 2 and each $R_6$ is unsubstituted $C_1$-$C_8$alkyl. In some embodiments is a compound of Formula (IIIa), wherein n is 2 and one $R_6$ is halogen and one $R_6$ is substituted or unsubstituted $C_1$-$C_8$alkoxy. In some embodiments is a compound of Formula (IIIa), wherein n is 2 and each $R_6$ is substituted or unsubstituted $C_1$-$C_8$alkoxy.

In some embodiments is a compound of Formula (IIIa), wherein $R_2$, $R_3$, $R_4$, and $R_5$ are each deuterium. In some embodiments is a compound of Formula (IIIa), wherein $R_2$, $R_3$, $R_4$, and $R_5$ are each hydrogen. In some embodiments is a compound of Formula (IIIa), wherein $R_2$ is —OH, and $R_3$, $R_4$, and $R_5$ are each hydrogen. In some embodiments is a compound of Formula (IIIa), wherein $R_3$ is —OH, and $R_2$, $R_4$, and $R_5$ are each hydrogen. In some embodiments is a compound of Formula (IIIa), wherein $R_2$ and $R_4$ are each —OH, and $R_3$ and $R_5$ are each hydrogen. In some embodiments is a compound of Formula (IIIa), wherein $R_2$ and $R_5$ are each —OH, and $R_3$ and $R_4$ are each hydrogen. In some embodiments is a compound of Formula (IIIa), wherein $R_3$ and $R_4$ are each —OH, and $R_2$ and $R_5$ are each hydrogen. In some embodiments is a compound of Formula (IIIa), wherein $R_3$ and $R_5$ are each —OH, and $R_2$ and $R_4$ are each hydrogen.

In some embodiments is a compound of Formula (IIIa), wherein $R_1$ is substituted or unsubstituted $C_1$-$C_8$alkyl. In some embodiments is a compound of Formula (IIIa), wherein $R_1$ is substituted $C_1$-$C_8$alkyl. In some embodiments is a compound of Formula (IIIa), wherein $R_1$ is —$CF_3$. In some embodiments is a compound of Formula (IIIa), wherein $R_1$ is unsubstituted $C_1$-$C_8$alkyl. In some embodiments is a compound of Formula (IIIa), wherein $R_1$ is —$CH_3$. In some embodiments is a compound of Formula (IIIa), wherein $R_1$ is —$CH_2CH_3$. In some embodiments is a compound of Formula (IIIa), wherein $R_1$ is substituted or unsubstituted aryl. In some embodiments is a compound of Formula (IIIa), wherein $R_1$ is unsubstituted phenyl.

In some embodiments is a compound having the structure of Formula (IV):

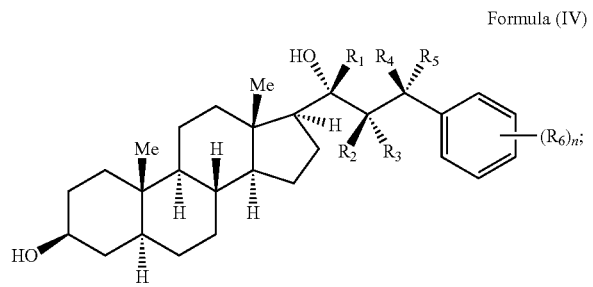

Formula (IV)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
- $R_2$, $R_3$, $R_4$, and $R_5$ are independently hydrogen, deuterium, or —OH; and
- n is 0, 1, 2, or 3.

In some embodiments is a compound of Formula (IV), wherein n is 0. In some embodiments is a compound of Formula (IV), wherein n is 1 and $R_6$ is halogen. In some embodiments is a compound of Formula (IV), wherein n is 1 and $R_6$ is F. In some embodiments is a compound of Formula (IV), wherein n is 1 and $R_6$ is Cl. In some embodiments is a compound of Formula (IV), wherein n is 1 and $R_6$ is Br. In some embodiments is a compound of Formula (IV), wherein n is 1 and $R_6$ is hydroxy. In some embodiments is a compound of Formula (IV), wherein n is 1 and $R_6$ is substituted or unsubstituted $C_1$-$C_8$alkyl. In some embodiments is a compound of Formula (IV), wherein n is 1 and $R_6$ is unsubstituted $C_1$-$C_8$alkyl. In some embodiments is a compound of Formula (IV), wherein n is 1 and $R_6$ is substituted or unsubstituted $C_1$-$C_8$alkoxy. In some embodiments is a compound of Formula (IV), wherein n is 2 and each $R_6$ is halogen. In some embodiments is a compound of Formula (IV), wherein n is 2 and each $R_6$ is F. In some embodiments is a compound of Formula (IV), wherein n is 2 and each $R_6$ is Cl. In some embodiments is a compound of Formula (IV), wherein n is 2 and each $R_6$ is Br. In some embodiments is a compound of Formula (IV), wherein n is 2 and one $R_6$ is halogen and one $R_6$ is hydroxy. In some embodiments is a compound of Formula (IV), wherein n is 2 and each $R_6$ is hydroxy. In some embodiments is a compound of Formula (IV), wherein n is 2 and one $R_6$ is halogen and one $R_6$ is substituted or unsubstituted $C_1$-$C_8$alkyl. In some embodiments is a compound of Formula (IV), wherein n is 2 and each $R_6$ is substituted or unsubstituted $C_1$-$C_8$alkyl. In some embodiments is a compound of Formula (IV), wherein n is 2 and each $R_6$ is unsubstituted $C_1$-$C_8$alkyl. In some embodiments is a compound of Formula (IV), wherein n is 2 and one $R_6$ is halogen and one $R_6$ is substituted or unsubstituted $C_1$-$C_8$alkoxy. In some embodiments is a compound of Formula (IV), wherein n is 2 and each $R_6$ is substituted or unsubstituted $C_1$-$C_8$alkoxy.

In some embodiments is a compound of Formula (IV), wherein $R_2$, $R_3$, $R_4$, and $R_5$ are each deuterium. In some embodiments is a compound of Formula (IV), wherein $R_2$, $R_3$, $R_4$, and $R_5$ are each hydrogen. In some embodiments is a compound of Formula (IV), wherein $R_2$ is —OH, and $R_3$, $R_4$, and $R_5$ are each hydrogen. In some embodiments is a compound of Formula (IV), wherein $R_3$ is —OH, and $R_2$, $R_4$, and $R_5$ are each hydrogen. In some embodiments is a compound of Formula (IV), wherein $R_2$ and $R_4$ are each —OH, and $R_3$ and $R_5$ are each hydrogen. In some embodiments is a compound of Formula (IV), wherein $R_2$ and $R_5$ are each —OH, and $R_3$ and $R_4$ are each hydrogen. In some embodiments is a compound of Formula (IV), wherein $R_3$ and $R_4$ are each —OH, and $R_2$ and $R_5$ are each hydrogen. In some embodiments is a compound of Formula (IV), wherein $R_3$ and $R_5$ are each —OH, and $R_2$ and $R_4$ are each hydrogen.

In some embodiments is a compound of Formula (IV), wherein $R_1$ is substituted or unsubstituted $C_1$-$C_8$alkyl. In some embodiments is a compound of Formula (IV), wherein $R_1$ is substituted $C_1$-$C_8$alkyl. In some embodiments is a compound of Formula (IV), wherein $R_1$ is —$CF_3$. In some embodiments is a compound of Formula (IV), wherein $R_1$ is unsubstituted $C_1$-$C_8$alkyl. In some embodiments is a compound of Formula (IV), wherein $R_1$ is —$CH_3$. In some embodiments is a compound of Formula (IV), wherein $R_1$ is —$CH_2CH_3$. In some embodiments is a compound of Formula (IV), wherein $R_1$ is substituted or unsubstituted aryl. In some embodiments is a compound of Formula (IV), wherein $R_1$ is unsubstituted phenyl.

In some embodiments is a compound having the structure of Formula (IVa):

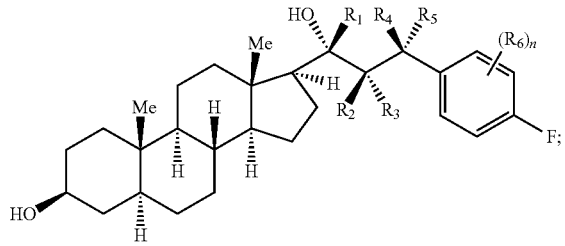

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
- $R_2$, $R_3$, $R_4$, and $R_5$ are independently hydrogen, deuterium, or —OH; and
- n is 0, 1, or 2.

In some embodiments is a compound of Formula (IVa), wherein n is 0. In some embodiments is a compound of Formula (IVa), wherein n is 1 and $R_6$ is halogen. In some embodiments is a compound of Formula (IVa), wherein n is 1 and R$_6$ is F. In some embodiments is a compound of Formula (IVa), wherein n is 1 and R$_6$ is Cl. In some embodiments is a compound of Formula (IVa), wherein n is 1 and R$_6$ is Br. In some embodiments is a compound of Formula (IVa), wherein n is 1 and R$_6$ is hydroxy. In some embodiments is a compound of Formula (IVa), wherein n is 1 and R$_6$ is substituted or unsubstituted C$_1$-C$_8$alkyl. In some embodiments is a compound of Formula (IVa), wherein n is 1 and R$_6$ is unsubstituted C$_1$-C$_8$alkyl. In some embodiments is a compound of Formula (IVa), wherein n is 1 and R$_6$ is substituted or unsubstituted C$_1$-C$_8$alkoxy. In some embodiments is a compound of Formula (IVa), wherein n is 2 and each R$_6$ is halogen. In some embodiments is a compound of Formula (IVa), wherein n is 2 and each R$_6$ is F. In some embodiments is a compound of Formula (IVa), wherein n is 2 and each R$_6$ is Cl. In some embodiments is a compound of Formula (IVa), wherein n is 2 and each R$_6$ is Br. In some embodiments is a compound of Formula (IVa), wherein n is 2 and one R$_6$ is halogen and one R$_6$ is hydroxy. In some embodiments is a compound of Formula (IVa), wherein n is 2 and each R$_6$ is hydroxy. In some embodiments is a compound of Formula (IVa), wherein n is 2 and one R$_6$ is halogen and one R$_6$ is substituted or unsubstituted C$_1$-C$_8$alkyl. In some embodiments is a compound of Formula (IVa), wherein n is 2 and each R$_6$ is substituted or unsubstituted C$_1$-C$_8$alkyl. In some embodiments is a compound of Formula (IVa), wherein n is 2 and each R$_6$ is unsubstituted C$_1$-C$_8$alkyl. In some embodiments is a compound of Formula (IVa), wherein n is 2 and one R$_6$ is halogen and one R$_6$ is substituted or unsubstituted C$_1$-C$_8$alkoxy. In some embodiments is a compound of Formula (IVa), wherein n is 2 and each R$_6$ is substituted or unsubstituted C$_1$-C$_8$alkoxy.

In some embodiments is a compound of Formula (IVa), wherein R$_2$, R$_3$, R$_4$, and R$_5$ are each deuterium. In some embodiments is a compound of Formula (IVa), wherein R$_2$, R$_3$, R$_4$, and R$_5$ are each hydrogen. In some embodiments is a compound of Formula (IVa), wherein R$_2$ is —OH, and R$_3$, R$_4$, and R$_5$ are each hydrogen. In some embodiments is a compound of Formula (IVa), wherein R$_3$ is —OH, and R$_2$, R$_4$, and R$_5$ are each hydrogen. In some embodiments is a compound of Formula (IVa), wherein R$_2$ and R$_4$ are each —OH, and R$_3$ and R$_5$ are each hydrogen. In some embodiments is a compound of Formula (IVa), wherein R$_2$ and R$_5$ are each —OH, and R$_3$ and R$_4$ are each hydrogen. In some embodiments is a compound of Formula (IVa), wherein R$_3$ and R$_4$ are each —OH, and R$_2$ and R$_5$ are each hydrogen. In some embodiments is a compound of Formula (IVa), wherein R$_3$ and R$_5$ are each —OH, and R$_2$ and R$_4$ are each hydrogen.

In some embodiments is a compound of Formula (IVa), wherein R$_1$ is substituted or unsubstituted C$_1$-C$_8$alkyl. In some embodiments is a compound of Formula (IVa), wherein R$_1$ is substituted C$_1$-C$_8$alkyl. In some embodiments is a compound of Formula (IVa), wherein R$_1$ is —CF$_3$. In some embodiments is a compound of Formula (IVa), wherein R$_1$ is unsubstituted C$_1$-C$_8$alkyl. In some embodiments is a compound of Formula (IVa), wherein R$_1$ is —CH$_3$. In some embodiments is a compound of Formula (IVa), wherein R$_1$ is —CH$_2$CH$_3$. In some embodiments is a compound of Formula (IVa), wherein R$_1$ is substituted or unsubstituted aryl. In some embodiments is a compound of Formula (IVa), wherein R$_1$ is unsubstituted phenyl.

In some embodiments is a compound selected from:

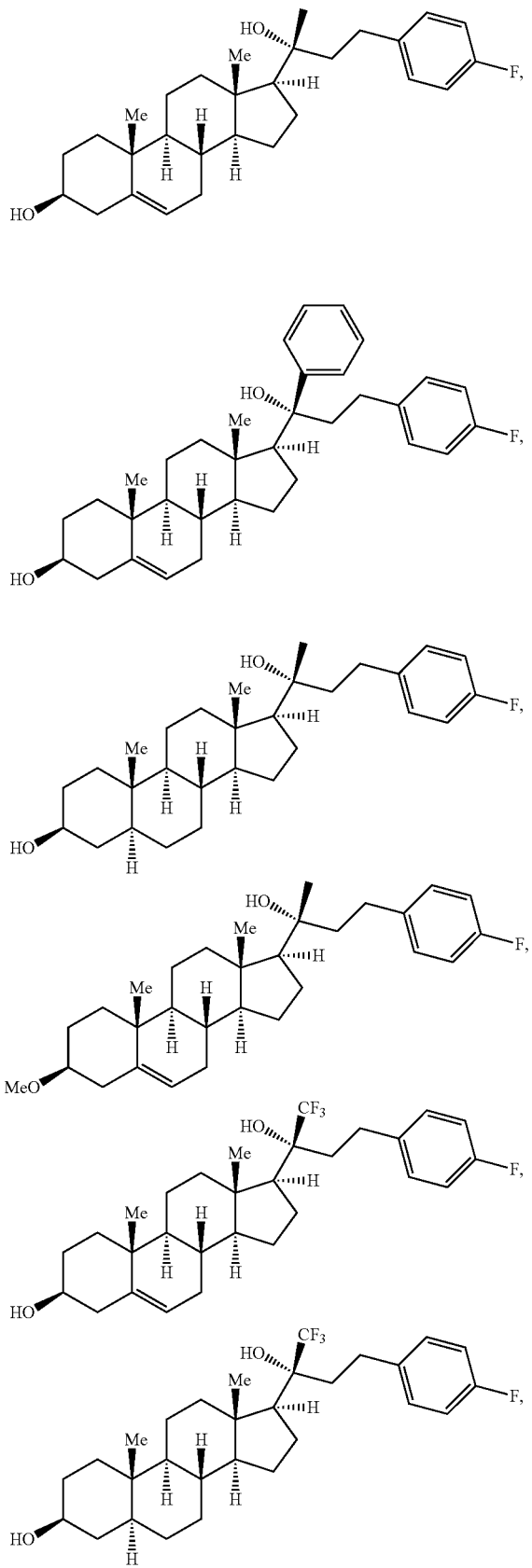

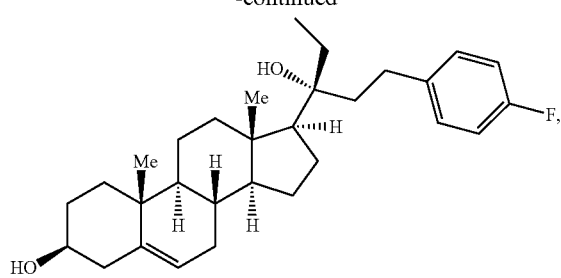
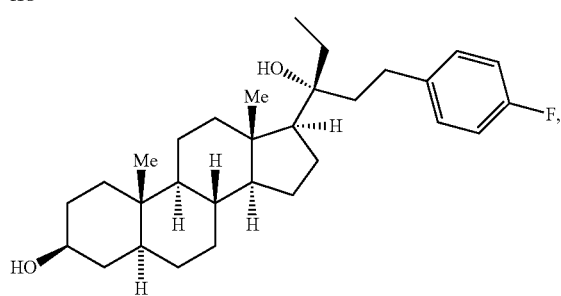
and
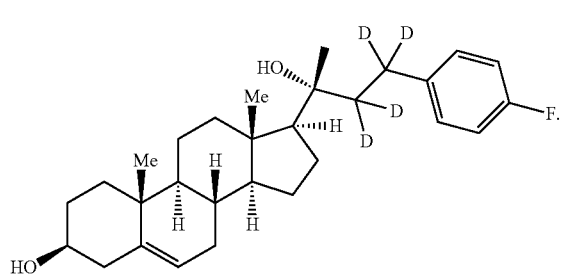
In some embodiments is a compound selected from:
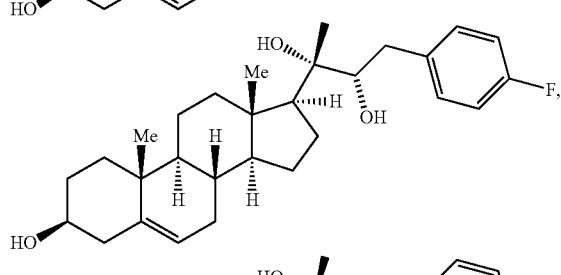
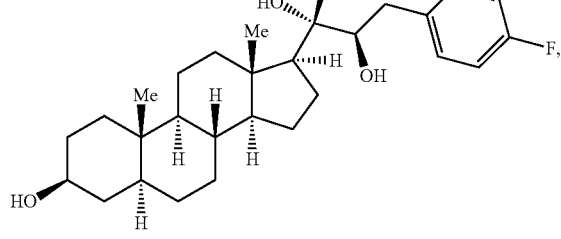
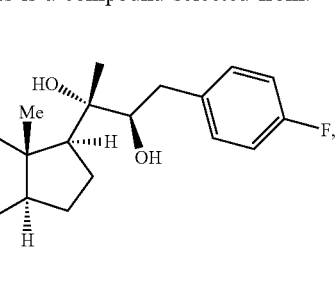
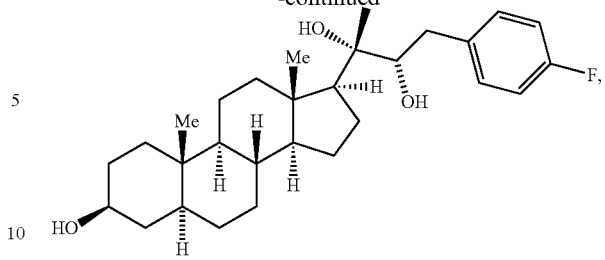
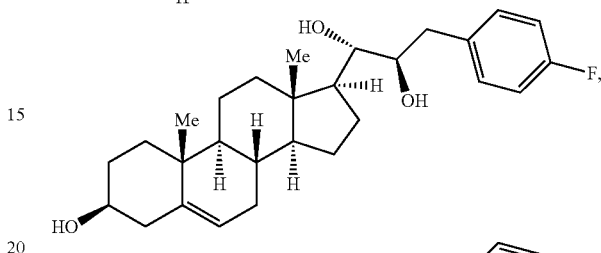
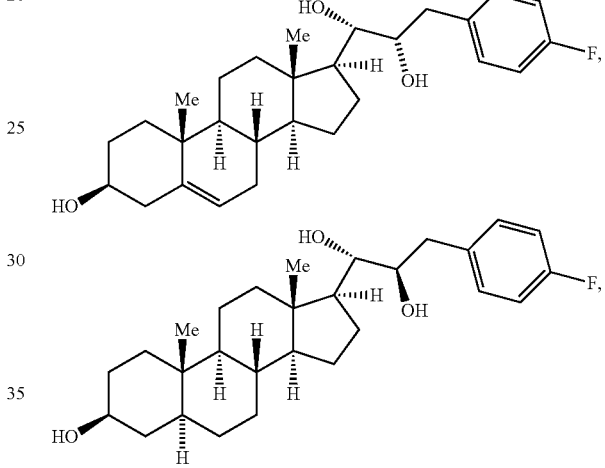

27
-continued
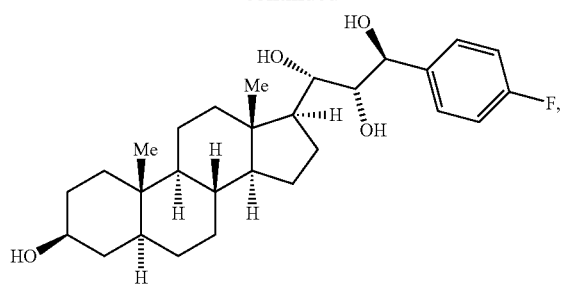
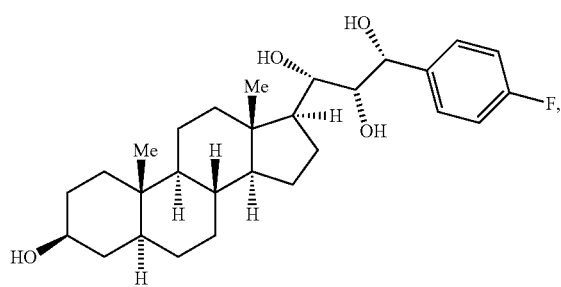
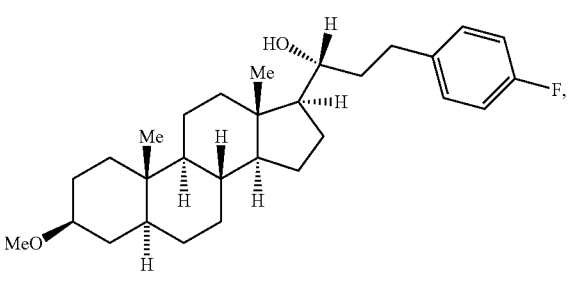
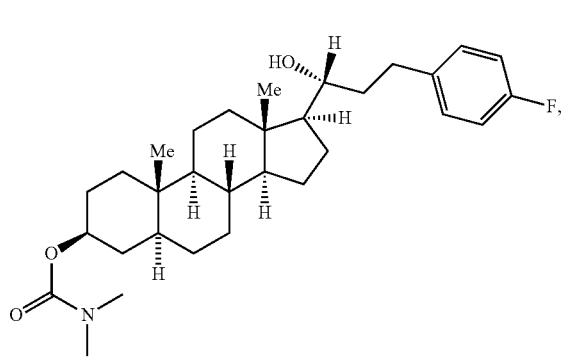
and
28
-continued
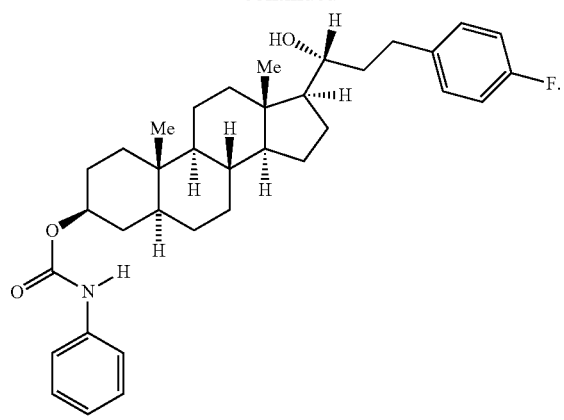
In some embodiments is a compound selected from:
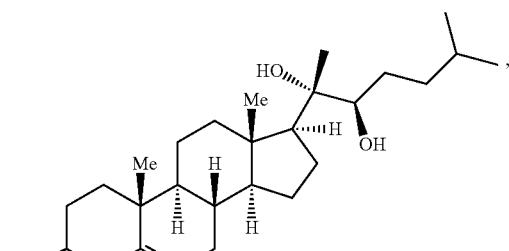
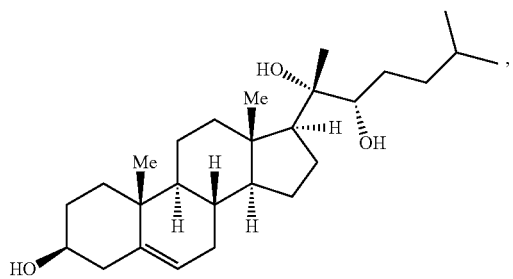
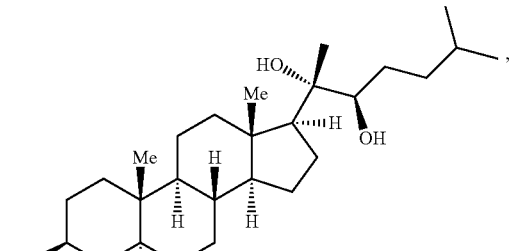
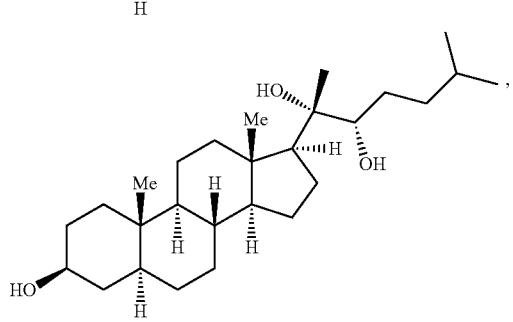

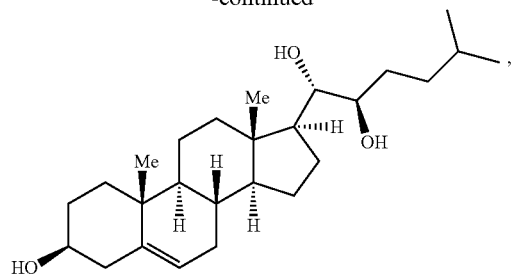
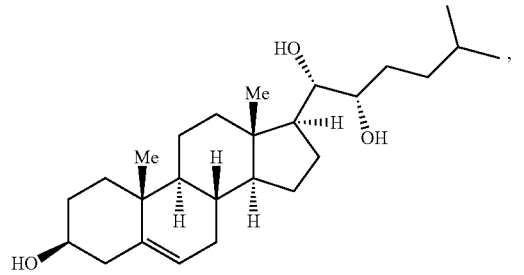
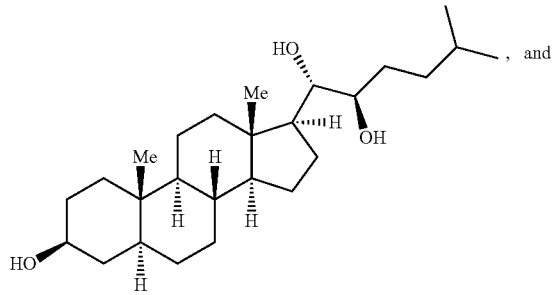
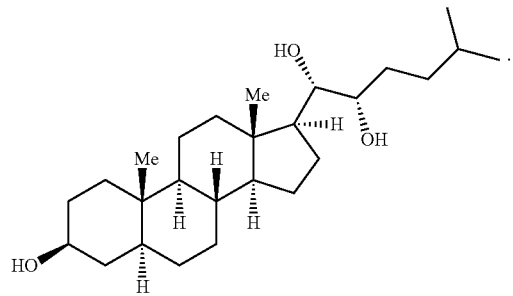
In some embodiments is a compound selected from:
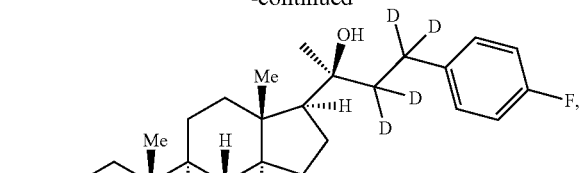
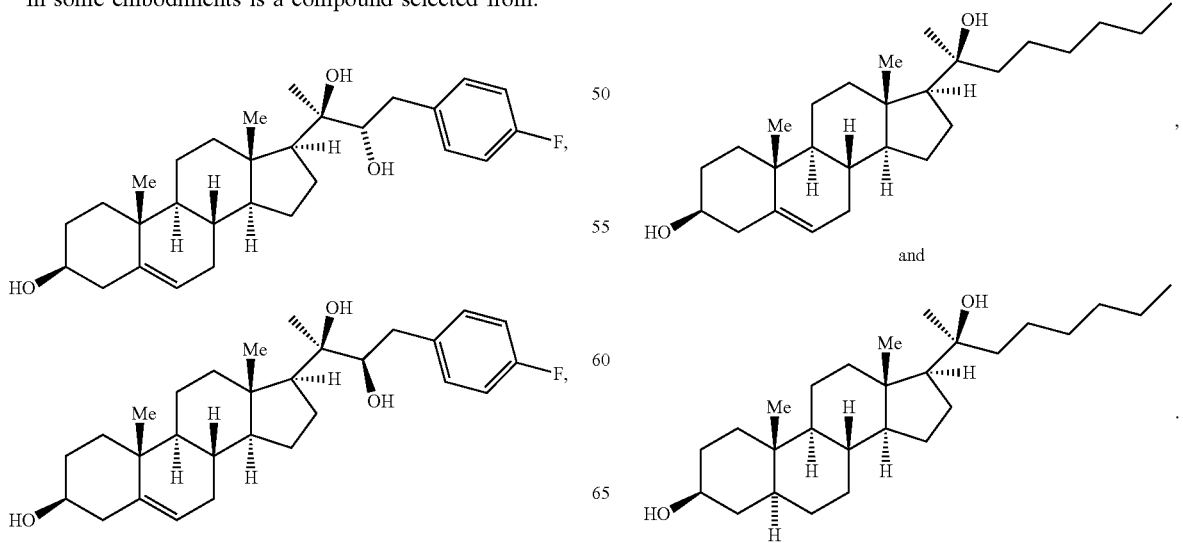
In some embodiments is a compound selected from:

Provided herein are pharmaceutical compositions comprising a therapeutically effective amount of a compound of Formula (I), (Ia), (Ib), (II), (IIa), (III), (IIIa), (IV), or (IVa). Further provided herein are pharmaceutical compositions comprising a therapeutically effective amount of a compound of Formula (I), (Ia), (Ib), (II), (IIa), (III), (IIIa), (IV), or (IVa) or a pharmaceutically acceptable salt or solvate thereof, and a pharmaceutically acceptable excipient, wherein the compound of Formula (I), (Ia), (Ib), (II), (IIa), (III), (IIIa), (IV), or (IVa) is as described herein.

Methods of Use

In some embodiments is a method of treating cancer in a mammal in need thereof comprising administering to the mammal a therapeutically effective amount of a compound having the structure of Formula (I):

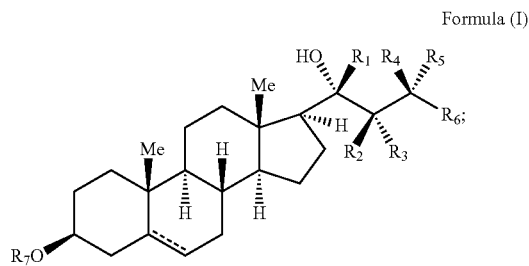

Formula (I)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- $R_6$ is substituted or unsubstituted aryl or substituted or unsubstituted heteroaryl;
- ====== is a single or double bond;
- $R_2$, $R_3$, $R_4$, and $R_5$ are independently hydrogen, deuterium, or —OH;
- $R_7$ is hydrogen, substituted or unsubstituted $C_1$-$C_8$alkyl, or —C(O)NR$_8$R$_9$; and
- $R_8$ and $R_9$ are independently hydrogen, substituted or unsubstituted $C_1$-$C_8$alkyl, or substituted or unsubstituted aryl.

In some embodiments is a method of treating cancer in a mammal in need thereof comprising administering to the mammal a therapeutically effective amount of a compound of Formula (I) wherein ====== is a single bond. In some embodiments is a method of treating cancer in a mammal in need thereof comprising administering to the mammal a therapeutically effective amount of a compound of Formula (I) wherein ====== is a double bond.

In some embodiments is a method of treating cancer in a mammal in need thereof comprising administering to the mammal a therapeutically effective amount of a compound of Formula (I), wherein $R_6$ is substituted or unsubstituted aryl. In some embodiments is a method of treating cancer in a mammal in need thereof comprising administering to the mammal a therapeutically effective amount of a compound of Formula (I), wherein $R_6$ is substituted or unsubstituted phenyl. In some embodiments is a method of treating cancer in a mammal in need thereof comprising administering to the mammal a therapeutically effective amount of a compound of Formula (I), wherein $R_6$ is unsubstituted phenyl. In some embodiments is a method of treating cancer in a mammal in need thereof comprising administering to the mammal a therapeutically effective amount of a compound of Formula (I), wherein $R_6$ is substituted phenyl. In some embodiments is a method of treating cancer in a mammal in need thereof comprising administering to the mammal a therapeutically effective amount of a compound of Formula (I), wherein $R_6$ is phenyl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkylamino, dialkyl-amino, and amido. In some embodiments is a method of treating cancer in a mammal in need thereof comprising administering to the mammal a therapeutically effective amount of a compound of Formula (I), wherein $R_6$ is phenyl substituted with at least one substituent selected from alkyl, hydroxy, alkoxy, halogen, and haloalkyl. In some embodiments is a method of treating cancer in a mammal in need thereof comprising administering to the mammal a therapeutically effective amount of a compound of Formula (I), wherein $R_6$ is phenyl substituted with at least one halogen substituent. In some embodiments is a method of treating cancer in a mammal in need thereof comprising administering to the mammal a therapeutically effective amount of a compound of Formula (I), wherein $R_6$ is phenyl substituted with at least one fluoro substituent.

In some embodiments is a method of treating cancer in a mammal in need thereof comprising administering to the mammal a therapeutically effective amount of a compound of Formula (I), wherein $R_6$ is substituted or unsubstituted heteroaryl. In some embodiments is a method of treating cancer in a mammal in need thereof comprising administering to the mammal a therapeutically effective amount of a compound of Formula (I), wherein $R_6$ is unsubstituted heteroaryl. In some embodiments is a method of treating cancer in a mammal in need thereof comprising administering to the mammal a therapeutically effective amount of a compound of Formula (I), wherein $R_6$ is substituted heteroaryl. In some embodiments is a method of treating cancer in a mammal in need thereof comprising administering to the mammal a therapeutically effective amount of a compound of Formula (I), wherein $R_6$ is heteroaryl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a method of treating cancer in a mammal in need thereof comprising administering to the mammal a therapeutically effective amount of a compound of Formula (I), wherein $R_6$ is heteroaryl substituted with at least one substituent selected from alkyl, hydroxy, alkoxy, halogen, and haloalkyl. In some embodiments is a method of treating cancer in a mammal in need thereof comprising administering to the mammal a therapeutically effective amount of a compound of Formula (I), wherein $R_6$ is heteroaryl substituted with at least one halogen substituent. In some embodiments is a method of treating cancer in a mammal in need thereof comprising administering to the mammal a therapeutically effective amount of a compound of Formula (I), wherein $R_6$ is a heteroaryl selected from thienyl, furyl, thiadiazolyl, benzothiadiazolyl, pyrrolyl, imidazolyl, oxazolyl, pyrazolyl, isothiazolyl, isoxazolyl, pyridyl, pyrazinyl, pyrimidinyl, pyridazinyl, pyrazolo-pyrimidinyl, triazolo-pyrimidinyl, and imidazo-pyrimidinyl.

In some embodiments is a method of treating cancer in a mammal in need thereof comprising administering to the mammal a therapeutically effective amount of a compound of Formula (I), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (I), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (I), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (I), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (I), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (I), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (I), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (I), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (I), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (I), wherein $R_1$ is substituted $C_1$-$C_8$alkyl. In some embodiments is a method of treating cancer in a mammal in need thereof comprising administering to the mammal a therapeutically effective amount of a compound of Formula (I), wherein $R_1$ is —CF$_3$. In some embodiments is a method of treating cancer in a mammal in need thereof comprising administering to the mammal a therapeutically effective amount of a compound of Formula (I), wherein $R_1$ is unsubstituted $C_1$-$C_8$alkyl. In some embodiments is a method of treating cancer in a mammal in need thereof comprising administering to the mammal a therapeutically effective amount of a compound of Formula (I), wherein $R_1$ is —CH$_3$. In some embodiments is a method of treating cancer in a mammal in need thereof comprising administering to the mammal a therapeutically effective amount of a compound of Formula (I), wherein $R_1$ is —CH$_2$CH$_3$. In some embodiments is a method of treating cancer in a mammal in need thereof comprising administering to the mammal a therapeutically effective amount of a compound of Formula (I), wherein $R_1$ is substituted or unsubstituted aryl. In some embodiments is a method of treating cancer in a mammal in need thereof comprising administering to the mammal a therapeutically effective amount of a compound of Formula (I), wherein $R_1$ is unsubstituted phenyl.

In some embodiments is a method of treating cancer in a mammal in need thereof comprising administering to the mammal a therapeutically effective amount of a compound of Formula (I), wherein $R_7$ is hydrogen. In some embodiments is a method of treating cancer in a mammal in need thereof comprising administering to the mammal a therapeutically effective amount of a compound of Formula (I), wherein $R_7$ is substituted or unsubstituted $C_1$-$C_8$alkyl. In some embodiments is a method of treating cancer in a mammal in need thereof comprising administering to the mammal a therapeutically effective amount of a compound of Formula (I), wherein $R_7$ is —CH$_3$. In some embodiments is a method of treating cancer in a mammal in need thereof comprising administering to the mammal a therapeutically effective amount of a compound of Formula (I), wherein $R_7$ is —C(O)NR$_8$R$_9$. In some embodiments is a method of treating cancer in a mammal in need thereof comprising administering to the mammal a therapeutically effective amount of a compound of Formula (I), wherein $R_7$ is substituted or unsubstituted $C_1$-$C_8$alkyl. In some embodiments is a method of treating cancer in a mammal in need thereof comprising administering to the mammal a therapeutically effective amount of a compound of Formula (I), wherein $R_7$ is —C(O)NR$_8$R$_9$, and $R_8$ and $R_9$ are independently substituted or unsubstituted $C_1$-$C_8$alkyl. In some embodiments is a method of treating cancer in a mammal in need thereof comprising administering to the mammal a therapeutically effective amount of a compound of Formula (I), wherein $R_7$ is —C(O)NR$_8$R$_9$, and $R_8$ and $R_9$ are each —CH$_3$. In some embodiments is a method of treating cancer in a mammal in need thereof comprising administering to the mammal a therapeutically effective amount of a compound of Formula (I), wherein $R_7$ is —C(O)NR$_8$R$_9$, $R_8$ is hydrogen, and $R_9$ is substituted or unsubstituted $C_1$-$C_8$alkyl. In some embodiments is a method of treating cancer in a mammal in need thereof comprising administering to the mammal a therapeutically effective amount of a compound of Formula (I), wherein $R_7$ is —C(O)NR$_8$R$_9$, $R_8$ is hydrogen, and $R_9$ is —CH$_3$. In some embodiments is a method of treating cancer in a mammal in need thereof comprising administering to the mammal a therapeutically effective amount of a compound of Formula (I), wherein $R_7$ is —C(O)NR$_8$R$_9$, $R_8$ is substituted or unsubstituted aryl, and $R_9$ is substituted or unsubstituted $C_1$-$C_8$alkyl. In some embodiments is a method of treating cancer in a mammal in need thereof comprising administering to the mammal a therapeutically effective amount of a compound of Formula (I), wherein $R_7$ is —C(O)NR$_8$R$_9$, $R_8$ is substituted or unsubstituted aryl, and $R_9$ is hydrogen.

In some embodiments is a method of treating cancer in a mammal in need thereof comprising administering to the mammal a therapeutically effective amount of a compound having the structure of Formula (Ia):

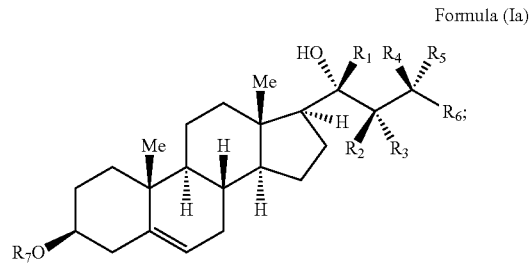

Formula (Ia)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- $R_6$ is substituted or unsubstituted aryl or substituted or unsubstituted heteroaryl;
- $R_2$, $R_3$, $R_4$, and $R_5$ are independently hydrogen, deuterium, or —OH;
- $R_7$ is hydrogen, substituted or unsubstituted $C_1$-$C_8$alkyl, or —C(O)$NR_8R_9$; and
- $R_8$ and $R_9$ are independently hydrogen, substituted or unsubstituted $C_1$-$C_8$alkyl, or substituted or unsubstituted aryl.

In some embodiments is a method of treating cancer in a mammal in need thereof comprising administering to the mammal a therapeutically effective amount of a compound of Formula (Ia), wherein $R_6$ is substituted or unsubstituted aryl. In some embodiments is a method of treating cancer in a mammal in need thereof comprising administering to the mammal a therapeutically effective amount of a compound of Formula (Ia), wherein $R_6$ is substituted or unsubstituted phenyl. In some embodiments is a method of treating cancer in a mammal in need thereof comprising administering to the mammal a therapeutically effective amount of a compound of Formula (Ia), wherein $R_6$ is unsubstituted phenyl. In some embodiments is a method of treating cancer in a mammal in need thereof comprising administering to the mammal a therapeutically effective amount of a compound of Formula (Ia), wherein $R_6$ is substituted phenyl. In some embodiments is a method of treating cancer in a mammal in need thereof comprising administering to the mammal a therapeutically effective amount of a compound of Formula (Ia), wherein $R_6$ is phenyl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a method of treating cancer in a mammal in need thereof comprising administering to the mammal a therapeutically effective amount of a compound of Formula (Ia), wherein $R_6$ is phenyl substituted with at least one substituent selected from alkyl, hydroxy, alkoxy, halogen, and haloalkyl. In some embodiments is a method of treating cancer in a mammal in need thereof comprising administering to the mammal a therapeutically effective amount of a compound of Formula (Ia), wherein $R_6$ is phenyl substituted with at least one halogen substituent. In some embodiments is a method of treating cancer in a mammal in need thereof comprising administering to the mammal a therapeutically effective amount of a compound of Formula (Ia), wherein $R_6$ is phenyl substituted with at least one fluoro substituent.

In some embodiments is a method of treating cancer in a mammal in need thereof comprising administering to the mammal a therapeutically effective amount of a compound of Formula (Ia), wherein $R_6$ is substituted or unsubstituted heteroaryl. In some embodiments is a method of treating cancer in a mammal in need thereof comprising administering to the mammal a therapeutically effective amount of a compound of Formula (Ia), wherein $R_6$ is unsubstituted heteroaryl. In some embodiments is a method of treating cancer in a mammal in need thereof comprising administering to the mammal a therapeutically effective amount of a compound of Formula (Ia), wherein $R_6$ is substituted heteroaryl. In some embodiments is a method of treating cancer in a mammal in need thereof comprising administering to the mammal a therapeutically effective amount of a compound of Formula (Ia), wherein $R_6$ is heteroaryl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a method of treating cancer in a mammal in need thereof comprising administering to the mammal a therapeutically effective amount of a compound of Formula (Ia), wherein $R_6$ is heteroaryl substituted with at least one substituent selected from alkyl, hydroxy, alkoxy, halogen, and haloalkyl. In some embodiments is a method of treating cancer in a mammal in need thereof comprising administering to the mammal a therapeutically effective amount of a compound of Formula (Ia), wherein $R_6$ is heteroaryl substituted with at least one halogen substituent. In some embodiments is a method of treating cancer in a mammal in need thereof comprising administering to the mammal a therapeutically effective amount of a compound of Formula (Ia), wherein $R_6$ is a heteroaryl selected from thienyl, furyl, thiadiazolyl, benzothiadiazolyl, pyrrolyl, imidazolyl, oxazolyl, pyrazolyl, isothiazolyl, isoxazolyl, pyridyl, pyrazinyl, pyrimidinyl, pyridazinyl, pyrazolo-pyrimidinyl, triazolo-pyrimidinyl, and imidazo-pyrimidinyl.

In some embodiments is a method of treating cancer in a mammal in need thereof comprising administering to the mammal a therapeutically effective amount of a compound of Formula (Ia), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (Ia), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (Ia), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (Ia), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (Ia), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (Ia), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (Ia), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (Ia), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (Ia), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (Ia), wherein $R_1$ is substituted $C_1$-$C_8$alkyl. In some embodiments is a method of treating cancer in a mammal in need thereof comprising administering to the mammal a therapeutically effective amount of a compound of Formula (Ia), wherein $R_1$ is —$CF_3$. In some embodiments is a method of treating cancer in a mammal in need thereof comprising administering to the mammal a therapeutically effective amount of a compound of Formula (Ia), wherein $R_1$ is unsubstituted $C_1$-$C_8$alkyl. In some embodiments is a method of treating cancer in a mammal in need thereof comprising administering to the mammal a therapeutically effective amount of a compound of Formula (Ia), wherein $R_1$ is —$CH_3$. In some embodiments is a method of treating cancer in a mammal in need thereof comprising administering to the mammal a therapeutically effective amount of a compound of Formula (Ia), wherein $R_1$ is —$CH_2CH_3$. In some embodiments is a method of treating cancer in a mammal in need thereof comprising administering to the mammal a therapeutically effective amount of a compound of Formula (Ia), wherein $R_1$ is substituted or unsubstituted aryl. In some embodiments is a method of treating cancer in a mammal in need thereof comprising administering to the mammal a therapeutically effective amount of a compound of Formula (Ia), wherein $R_1$ is unsubstituted phenyl.

In some embodiments is a method of treating cancer in a mammal in need thereof comprising administering to the mammal a therapeutically effective amount of a compound of Formula (Ia), wherein $R_7$ is hydrogen. In some embodiments is a method of treating cancer in a mammal in need thereof comprising administering to the mammal a therapeutically effective amount of a compound of Formula (Ia), wherein $R_7$ is substituted or unsubstituted $C_1$-$C_8$alkyl. In some embodiments is a method of treating cancer in a mammal in need thereof comprising administering to the mammal a therapeutically effective amount of a compound of Formula (Ia), wherein $R_7$ is —$CH_3$. In some embodiments is a method of treating cancer in a mammal in need thereof comprising administering to the mammal a therapeutically effective amount of a compound of Formula (Ia), wherein $R_7$ is —$C(O)NR_8R_9$. In some embodiments is a method of treating cancer in a mammal in need thereof comprising administering to the mammal a therapeutically effective amount of a compound of Formula (Ia), wherein $R_7$ is substituted or unsubstituted $C_1$-$C_8$alkyl. In some embodiments is a method of treating cancer in a mammal in need thereof comprising administering to the mammal a therapeutically effective amount of a compound of Formula (Ia), wherein $R_7$ is —$C(O)NR_8R_9$, and $R_8$ and $R_9$ are independently substituted or unsubstituted $C_1$-$C_8$alkyl. In some embodiments is a method of treating cancer in a mammal in need thereof comprising administering to the mammal a therapeutically effective amount of a compound of Formula (Ia), wherein $R_7$ is —$C(O)NR_8R_9$, and $R_8$ and $R_9$ are each —$CH_3$. In some embodiments is a method of treating cancer in a mammal in need thereof comprising administering to the mammal a therapeutically effective amount of a compound of Formula (Ia), wherein $R_7$ is —$C(O)NR_8R_9$, $R_8$ is hydrogen, and $R_9$ is substituted or unsubstituted $C_1$-$C_8$alkyl. In some embodiments is a method of treating cancer in a mammal in need thereof comprising administering to the mammal a therapeutically effective amount of a compound of Formula (Ia), wherein $R_7$ is —$C(O)NR_8R_9$, $R_8$ is hydrogen, and $R_9$ is —$CH_3$. In some embodiments is a method of treating cancer in a mammal in need thereof comprising administering to the mammal a therapeutically effective amount of a compound of Formula (Ia), wherein $R_7$ is —$C(O)NR_8R_9$, $R_8$ is substituted or unsubstituted aryl, and $R_9$ is substituted or unsubstituted $C_1$-$C_8$alkyl. In some embodiments is a method of treating cancer in a mammal in need thereof comprising administering to the mammal a therapeutically effective amount of a compound of Formula (Ia), wherein $R_7$ is —$C(O)NR_8R_9$, $R_8$ is substituted or unsubstituted aryl, and $R_9$ is hydrogen.

In some embodiments is a method of treating cancer in a mammal in need thereof comprising administering to the mammal a therapeutically effective amount of a compound having the structure of Formula (Ib):

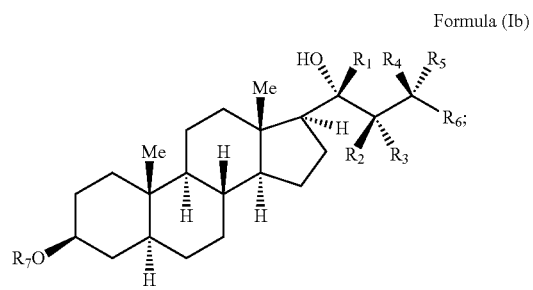

Formula (Ib)

wherein:
  $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
  $R_6$ is substituted or unsubstituted aryl or substituted or unsubstituted heteroaryl;
  $R_2$, $R_3$, $R_4$, and $R_5$ are independently hydrogen, deuterium, or —OH;
  $R_7$ is hydrogen, substituted or unsubstituted $C_1$-$C_8$alkyl, or —$C(O)NR_8R_9$; and
  $R_8$ and $R_9$ are independently hydrogen, substituted or unsubstituted $C_1$-$C_8$alkyl, or substituted or unsubstituted aryl.

In some embodiments is a method of treating cancer in a mammal in need thereof comprising administering to the mammal a therapeutically effective amount of a compound of Formula (Ib), wherein $R_6$ is substituted or unsubstituted aryl. In some embodiments is a method of treating cancer in a mammal in need thereof comprising administering to the mammal a therapeutically effective amount of a compound of Formula (Ib), wherein $R_6$ is substituted or unsubstituted phenyl. In some embodiments is a method of treating cancer in a mammal in need thereof comprising administering to the mammal a therapeutically effective amount of a compound of Formula (Ib), wherein $R_6$ is unsubstituted phenyl. In some embodiments is a method of treating cancer in a mammal in need thereof comprising administering to the mammal a therapeutically effective amount of a compound of Formula (Ib), wherein $R_6$ is substituted phenyl. In some embodiments is a method of treating cancer in a mammal in need thereof comprising administering to the mammal a therapeutically effective amount of a compound of Formula (Ib), wherein $R_6$ is phenyl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkylamino, dialkyl-amino, and amido. In some embodiments is a method of treating cancer in a mammal in need thereof comprising administering to the mammal a therapeutically effective amount of a compound of Formula (Ib), wherein $R_6$ is phenyl substituted with at least one substituent selected from alkyl, hydroxy, alkoxy, halogen, and haloalkyl. In some embodiments is a method of treating cancer in a mammal in need thereof comprising administering to the mammal a therapeutically effective amount of a compound of Formula (Ib), wherein $R_6$ is phenyl substituted with at least one halogen substituent. In some embodiments is a method of treating cancer in a mammal in need thereof comprising administering to the mammal a therapeutically effective amount of a compound of Formula (Ib), wherein $R_6$ is phenyl substituted with at least one fluoro substituent.

In some embodiments is a method of treating cancer in a mammal in need thereof comprising administering to the mammal a therapeutically effective amount of a compound of Formula (Ib), wherein $R_6$ is substituted or unsubstituted heteroaryl. In some embodiments is a method of treating cancer in a mammal in need thereof comprising administering to the mammal a therapeutically effective amount of a compound of Formula (Ib), wherein $R_6$ is unsubstituted heteroaryl. In some embodiments is a method of treating cancer in a mammal in need thereof comprising administering to the mammal a therapeutically effective amount of a compound of Formula (Ib), wherein $R_6$ is substituted heteroaryl. In some embodiments is a method of treating cancer in a mammal in need thereof comprising administering to the mammal a therapeutically effective amount of a compound of Formula (Ib), wherein $R_6$ is heteroaryl substituted with at least one substituent selected from amide, ester, alkyl, cycloalkyl, heteroalkyl, aryl, heteroaryl, heterocycloalkyl, hydroxy, alkoxy, aryloxy, alkylthio, arylthio, alkylsulfoxide, arylsulfoxide, ester, alkylsulfone, arylsulfone, cyano, halogen, alkoyl, alkoyloxo, isocyanato, thiocyanato, isothiocyanato, nitro, haloalkyl, haloalkoxy, fluoroalkyl, amino, alkyl-amino, dialkyl-amino, and amido. In some embodiments is a method of treating cancer in a mammal in need thereof comprising administering to the mammal a therapeutically effective amount of a compound of Formula (Ib), wherein $R_6$ is heteroaryl substituted with at least one substituent selected from alkyl, hydroxy, alkoxy, halogen, and haloalkyl. In some embodiments is a method of treating cancer in a mammal in need thereof comprising administering to the mammal a therapeutically effective amount of a compound of Formula (Ib), wherein $R_6$ is heteroaryl substituted with at least one halogen substituent. In some embodiments is a method of treating cancer in a mammal in need thereof comprising administering to the mammal a therapeutically effective amount of a compound of Formula (Ib), wherein $R_6$ is a heteroaryl selected from thienyl, furyl, thiadiazolyl, benzothiadiazolyl, pyrrolyl, imidazolyl, oxazolyl, pyrazolyl, isothiazolyl, isoxazolyl, pyridyl, pyrazinyl, pyrimidinyl, pyridazinyl, pyrazolo-pyrimidinyl, triazolo-pyrimidinyl, and imidazo-pyrimidinyl.

In some embodiments is a method of treating cancer in a mammal in need thereof comprising administering to the mammal a therapeutically effective amount of a compound of Formula (Ib), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (Ib), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (Ib), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (Ib), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (Ib), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (Ib), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (Ib), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (Ib), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (Ib), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (Ib), wherein $R_1$ is substituted $C_1$-$C_8$alkyl. In some embodiments is a method of treating cancer in a mammal in need thereof comprising administering to the mammal a therapeutically effective amount of a compound of Formula (Ib), wherein $R_1$ is —$CF_3$. In some embodiments is a method of treating cancer in a mammal in need thereof comprising administering to the mammal a therapeutically effective amount of a compound of Formula (Ib), wherein $R_1$ is unsubstituted $C_1$-$C_8$alkyl. In some embodiments is a method of treating cancer in a mammal in need thereof comprising administering to the mammal a therapeutically effective amount of a compound of Formula (Ib), wherein $R_1$ is —$CH_3$. In some embodiments is a method of treating cancer in a mammal in need thereof comprising administering to the mammal a therapeutically effective amount of a compound of Formula (Ib), wherein $R_1$ is —$CH_2CH_3$. In some embodiments is a method of treating cancer in a mammal in need thereof comprising administering to the mammal a therapeutically effective amount of a compound of Formula (Ib), wherein $R_1$ is substituted or unsubstituted aryl. In some embodiments is a method of treating cancer in a mammal in need thereof comprising administering to the mammal a therapeutically effective amount of a compound of Formula (Ib), wherein $R_1$ is unsubstituted phenyl.

In some embodiments is a method of treating cancer in a mammal in need thereof comprising administering to the mammal a therapeutically effective amount of a compound of Formula (Ib), wherein $R_7$ is hydrogen. In some embodiments is a method of treating cancer in a mammal in need thereof comprising administering to the mammal a therapeutically effective amount of a compound of Formula (Ib), wherein $R_7$ is substituted or unsubstituted $C_1$-$C_8$alkyl. In some embodiments is a method of treating cancer in a mammal in need thereof comprising administering to the mammal a therapeutically effective amount of a compound of Formula (Ib), wherein $R_7$ is —$CH_3$. In some embodiments is a method of treating cancer in a mammal in need thereof comprising administering to the mammal a therapeutically effective amount of a compound of Formula (Ib), wherein $R_7$ is —C(O)$NR_8R_9$. In some embodiments is a method of treating cancer in a mammal in need thereof comprising administering to the mammal a therapeutically effective amount of a compound of Formula (Ib), wherein $R_7$ is substituted or unsubstituted $C_1$-$C_8$alkyl. In some embodiments is a method of treating cancer in a mammal in need thereof comprising administering to the mammal a therapeutically effective amount of a compound of Formula (Ib), wherein $R_7$ is —C(O)$NR_8R_9$, and $R_8$ and $R_9$ are independently substituted or unsubstituted $C_1$-$C_8$alkyl. In some embodiments is a method of treating cancer in a mammal in need thereof comprising administering to the mammal a therapeutically effective amount of a compound of Formula (Ib), wherein $R_7$ is —C(O)$NR_8R_9$, and $R_8$ and $R_9$ are each —$CH_3$. In some embodiments is a method of treating cancer in a mammal in need thereof comprising administering to the mammal a therapeutically effective amount of a compound of Formula (Ib), wherein $R_7$ is —C(O)$NR_8R_9$, $R_8$ is hydrogen, and $R_9$ is substituted or unsubstituted $C_1$-$C_8$alkyl. In some embodiments is a method of treating cancer in a mammal in need thereof comprising administering to the mammal a therapeutically effective amount of a compound of Formula (Ib), wherein $R_7$ is —C(O)$NR_8R_9$, $R_8$ is hydrogen, and $R_9$ is —$CH_3$. In some embodiments is a method of treating cancer in a mammal in need thereof comprising administering to the mammal a therapeutically effective amount of a compound of Formula (Ib), wherein $R_7$ is —C(O)$NR_8R_9$, $R_8$ is substituted or unsubstituted aryl, and $R_9$ is substituted or unsubstituted $C_1$-$C_8$alkyl. In some embodiments is a method of treating cancer in a mammal in need thereof comprising administering to the mammal a therapeutically effective amount of a compound of Formula (Ib), wherein $R_7$ is —C(O)$NR_8R_9$, $R_8$ is substituted or unsubstituted aryl, and $R_9$ is hydrogen.

In some embodiments is a method of treating cancer in a mammal in need thereof comprising administering to the mammal a therapeutically effective amount of a compound having the structure of Formula (II):

Formula (II)

wherein:
  $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
  each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
  ====== is a single or double bond;
  $R_2$, $R_3$, $R_4$, and $R_5$ are independently hydrogen, deuterium, or —OH; and
  n is 0, 1, 2, or 3.

In some embodiments is a method of treating cancer in a mammal in need thereof comprising administering to the mammal a therapeutically effective amount of a compound of Formula (II) wherein ====== is a single bond. In some embodiments is a method of treating cancer in a mammal in need thereof comprising administering to the mammal a therapeutically effective amount of a compound of Formula (II) wherein ====== is a double bond.

In some embodiments is a method of treating cancer in a mammal in need thereof comprising administering to the mammal a therapeutically effective amount of a compound of Formula (II), wherein n is 0. In some embodiments is a method of treating cancer in a mammal in need thereof comprising administering to the mammal a therapeutically effective amount of a compound of Formula (II), wherein n is 1 and $R_6$ is halogen. In some embodiments is a method of treating cancer in a mammal in need thereof comprising administering to the mammal a therapeutically effective amount of a compound of Formula (II), wherein n is 1 and $R_6$ is F. In some embodiments is a method of treating cancer in a mammal in need thereof comprising administering to the mammal a therapeutically effective amount of a compound of Formula (II), wherein n is 1 and $R_6$ is Cl. In some embodiments is a method of treating cancer in a mammal in need thereof comprising administering to the mammal a therapeutically effective amount of a compound of Formula (II), wherein n is 1 and $R_6$ is Br. In some embodiments is a method of treating cancer in a mammal in need thereof comprising administering to the mammal a therapeutically effective amount of a compound of Formula (II), wherein n is 1 and $R_6$ is hydroxy. In some embodiments is a method of treating cancer in a mammal in need thereof comprising administering to the mammal a therapeutically effective amount of a compound of Formula (II), wherein n is 1 and $R_6$ is substituted or unsubstituted $C_1$-$C_8$alkyl. In some embodiments is a method of treating cancer in a mammal in need thereof comprising administering to the mammal a therapeutically effective amount of a compound of Formula (II), wherein n is 1 and $R_6$ is unsubstituted $C_1$-$C_8$alkyl. In some embodiments is a method of treating cancer in a mammal in need thereof comprising administering to the mammal a therapeutically effective amount of a compound of Formula (II), wherein n is 1 and $R_6$ is substituted or unsubstituted $C_1$-$C_8$alkoxy. In some embodiments is a method of treating cancer in a mammal in need thereof comprising administering to the mammal a therapeutically effective amount of a compound of Formula (II), wherein n is 2 and each $R_6$ is halogen. In some embodiments is a method of treating cancer in a mammal in need thereof comprising administering to the mammal a therapeutically effective amount of a compound of Formula (II), wherein n is 2 and each $R_6$ is F. In some embodiments is a method of treating cancer in a mammal in need thereof comprising administering to the mammal a therapeutically effective amount of a compound of Formula (II), wherein n is 2 and each $R_6$ is Cl. In some embodiments is a method of treating cancer in a mammal in need thereof comprising administering to the mammal a therapeutically effective amount of a compound of Formula (II), wherein n is 2 and each $R_6$ is Br. In some embodiments is a method of treating cancer in a mammal in need thereof comprising administering to the mammal a therapeutically effective amount of a compound of Formula (II), wherein n is 2 and one $R_6$ is halogen and one $R_6$ is hydroxy. In some embodiments is a method of treating cancer in a mammal in need thereof comprising administering to the mammal a therapeutically effective amount of a compound of Formula (II), wherein n is 2 and each $R_6$ is hydroxy. In some embodiments is a method of treating cancer in a mammal in need thereof comprising administering to the mammal a therapeutically effective amount of a compound of Formula (II), wherein n is 2 and one $R_6$ is halogen and one $R_6$ is substituted or unsubstituted $C_1$-$C_8$alkyl. In some embodiments is a method of treating cancer in a mammal in need thereof comprising administering to the mammal a therapeutically effective amount of a compound of Formula (II), wherein n is 2 and each $R_6$ is substituted or unsubstituted $C_1$-$C_8$alkyl. In some embodiments is a method of treating cancer in a mammal in need thereof comprising administering to the mammal a therapeutically effective amount of a compound of Formula (II), wherein n is 2 and each $R_6$ is unsubstituted $C_1$-$C_8$alkyl. In some embodiments is a method of treating cancer in a mammal in need thereof comprising administering to the mammal a therapeutically effective amount of a compound of Formula (II), wherein n is 2 and one $R_6$ is halogen and one $R_6$ is substituted or unsubstituted $C_1$-$C_8$alkoxy. In some embodiments is a method of treating cancer in a mammal in need thereof comprising administering to the mammal a therapeutically effective amount of a compound of Formula (II), wherein n is 2 and each $R_6$ is substituted or unsubstituted $C_1$-$C_8$alkoxy.

In some embodiments is a method of treating cancer in a mammal in need thereof comprising administering to the mammal a therapeutically effective amount of a compound of Formula (II), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (II), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (II), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (II), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (II), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (II), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (II), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (II), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (II), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (II), wherein $R_1$ is substituted $C_1$-$C_8$alkyl. In some embodiments is a method of treating cancer in a mammal in need thereof comprising administering to the mammal a therapeutically effective amount of a compound of Formula (II), wherein $R_1$ is —$CF_3$. In some embodiments is a method of treating cancer in a mammal in need thereof comprising administering to the mammal a therapeutically effective amount of a compound of Formula (II), wherein $R_1$ is unsubstituted $C_1$-$C_8$alkyl. In some embodiments is a method of treating cancer in a mammal in need thereof comprising administering to the mammal a therapeutically effective amount of a compound of Formula (II), wherein $R_1$ is —$CH_3$. In some embodiments is a method of treating cancer in a mammal in need thereof comprising administering to the mammal a therapeutically effective amount of a compound of Formula (II), wherein $R_1$ is —$CH_2CH_3$. In some embodiments is a method of treating cancer in a mammal in need thereof comprising administering to the mammal a therapeutically effective amount of a compound of Formula (II), wherein $R_1$ is substituted or unsubstituted aryl. In some embodiments is a method of treating cancer in a mammal in need thereof comprising administering to the mammal a therapeutically effective amount of a compound of Formula (II), wherein $R_1$ is unsubstituted phenyl.

In some embodiments is a method of treating cancer in a mammal in need thereof comprising administering to the mammal a therapeutically effective amount of a compound having the structure of Formula (IIa):

Formula (IIa)

wherein:
R$_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;

each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;

===== is a single or double bond;

R$_2$, R$_3$, R$_4$, and R$_5$ are independently hydrogen, deuterium, or —OH; and n is 0, 1, or 2.

In some embodiments is a method of treating cancer in a mammal in need thereof comprising administering to the mammal a therapeutically effective amount of a compound of Formula (IIa) wherein ===== is a single bond. In some embodiments is a method of treating cancer in a mammal in need thereof comprising administering to the mammal a therapeutically effective amount of a compound of Formula (IIa) wherein ===== is a double bond.

In some embodiments is a method of treating cancer in a mammal in need thereof comprising administering to the mammal a therapeutically effective amount of a compound of Formula (IIa), wherein n is 0. In some embodiments is a method of treating cancer in a mammal in need thereof comprising administering to the mammal a therapeutically effective amount of a compound of Formula (IIa), wherein n is 1 and R$_6$ is halogen. In some embodiments is a method of treating cancer in a mammal in need thereof comprising administering to the mammal a therapeutically effective amount of a compound of Formula (IIa), wherein n is 1 and R$_6$ is F. In some embodiments is a method of treating cancer in a mammal in need thereof comprising administering to the mammal a therapeutically effective amount of a compound of Formula (IIa), wherein n is 1 and R$_6$ is Cl. In some embodiments is a method of treating cancer in a mammal in need thereof comprising administering to the mammal a therapeutically effective amount of a compound of Formula (IIa), wherein n is 1 and R$_6$ is Br. In some embodiments is a method of treating cancer in a mammal in need thereof comprising administering to the mammal a therapeutically effective amount of a compound of Formula (IIa), wherein n is 1 and R$_6$ is hydroxy. In some embodiments is a method of treating cancer in a mammal in need thereof comprising administering to the mammal a therapeutically effective amount of a compound of Formula (IIa), wherein n is 1 and R$_6$ is substituted or unsubstituted C$_1$-C$_8$alkyl. In some embodiments is a method of treating cancer in a mammal in need thereof comprising administering to the mammal a therapeutically effective amount of a compound of Formula (IIa), wherein n is 1 and R$_6$ is unsubstituted C$_1$-C$_8$alkyl. In some embodiments is a method of treating cancer in a mammal in need thereof comprising administering to the mammal a therapeutically effective amount of a compound of Formula (IIa), wherein n is 1 and R$_6$ is substituted or unsubstituted C$_1$-C$_8$alkoxy. In some embodiments is a method of treating cancer in a mammal in need thereof comprising administering to the mammal a therapeutically effective amount of a compound of Formula (IIa), wherein n is 2 and each R$_6$ is halogen. In some embodiments is a method of treating cancer in a mammal in need thereof comprising administering to the mammal a therapeutically effective amount of a compound of Formula (IIa), wherein n is 2 and each R$_6$ is F. In some embodiments is a method of treating cancer in a mammal in need thereof comprising administering to the mammal a therapeutically effective amount of a compound of Formula (IIa), wherein n is 2 and each R$_6$ is Cl. In some embodiments is a method of treating cancer in a mammal in need thereof comprising administering to the mammal a therapeutically effective amount of a compound of Formula (IIa), wherein n is 2 and each R$_6$ is Br. In some embodiments is a method of treating cancer in a mammal in need thereof comprising administering to the mammal a therapeutically effective amount of a compound of Formula (IIa), wherein n is 2 and one R$_6$ is halogen and one R$_6$ is hydroxy. In some embodiments is a method of treating cancer in a mammal in need thereof comprising administering to the mammal a therapeutically effective amount of a compound of Formula (IIa), wherein n is 2 and each R$_6$ is hydroxy. In some embodiments is a method of treating cancer in a mammal in need thereof comprising administering to the mammal a therapeutically effective amount of a compound of Formula (IIa), wherein n is 2 and one R$_6$ is halogen and one R$_6$ is substituted or unsubstituted C$_1$-C$_8$alkyl. In some embodiments is a method of treating cancer in a mammal in need thereof comprising administering to the mammal a therapeutically effective amount of a compound of Formula (IIa), wherein n is 2 and each R$_6$ is substituted or unsubstituted C$_1$-C$_8$alkyl. In some embodiments is a method of treating cancer in a mammal in need thereof comprising administering to the mammal a therapeutically effective amount of a compound of Formula (IIa), wherein n is 2 and each R$_6$ is unsubstituted C$_1$-C$_8$alkyl. In some embodiments is a method of treating cancer in a mammal in need thereof comprising administering to the mammal a therapeutically effective amount of a compound of Formula (IIa), wherein n is 2 and one R$_6$ is halogen and one R$_6$ is substituted or unsubstituted C$_1$-C$_8$alkoxy. In some embodiments is a method of treating cancer in a mammal in need thereof comprising administering to the mammal a therapeutically effective amount of a compound of Formula (IIa), wherein n is 2 and each R$_6$ is substituted or unsubstituted C$_1$-C$_8$alkoxy.

In some embodiments is a method of treating cancer in a mammal in need thereof comprising administering to the mammal a therapeutically effective amount of a compound of Formula (IIa), wherein R$_2$, R$_3$, R$_4$, and R$_5$ are each deuterium. In some embodiments is a method of treating cancer in a mammal in need thereof comprising administering to the mammal a therapeutically effective amount of a compound of Formula (IIa), wherein R$_2$, R$_3$, R$_4$, and R$_5$ are each hydrogen. In some embodiments is a method of treating cancer in a mammal in need thereof comprising administering to the mammal a therapeutically effective amount of a compound of Formula (IIa), wherein R$_2$ is —OH, and R$_3$, R$_4$, and R$_5$ are each hydrogen. In some embodiments is a method of treating cancer in a mammal in need thereof comprising administering to the mammal a therapeutically effective amount of a compound of Formula (IIa), wherein R$_3$ is —OH, and R$_2$, R$_4$, and R$_5$ are each hydrogen. In some embodiments is a method of treating cancer in a mammal in need thereof comprising administering to the mammal a therapeutically effective amount of a compound of Formula (IIa), wherein R$_2$ and R$_4$ are each —OH, and R$_3$ and R$_5$ are each hydrogen. In some embodiments is a method of treating cancer in a mammal in need thereof comprising administering to the mammal a therapeutically effective amount of a compound of Formula (IIa), wherein R$_2$ and R$_5$ are each —OH, and R$_3$ and R$_4$ are each hydrogen. In some embodiments is a method of treating cancer in a mammal in need thereof comprising administering to the mammal a therapeutically effective amount of a compound of Formula (IIa), wherein R$_3$ and R$_4$ are each —OH, and R$_2$ and R$_5$ are each hydrogen. In some embodiments is a method of treating cancer in a mammal in need thereof comprising administering to the mammal a therapeutically effective amount of a compound of Formula (IIa), wherein R$_3$ and R$_5$ are each —OH, and R$_2$ and R$_4$ are each hydrogen.

In some embodiments is a method of treating cancer in a mammal in need thereof comprising administering to the mammal a therapeutically effective amount of a compound of Formula (IIa), wherein R$_1$ is substituted or unsubstituted C$_1$-C$_8$alkyl. In some embodiments is a method of treating cancer in a mammal in need thereof comprising administering to the mammal a therapeutically effective amount of a compound of Formula (IIa), wherein $R_1$ is substituted $C_1$-$C_8$alkyl. In some embodiments is a method of treating cancer in a mammal in need thereof comprising administering to the mammal a therapeutically effective amount of a compound of Formula (IIa), wherein $R_1$ is —$CF_3$. In some embodiments is a method of treating cancer in a mammal in need thereof comprising administering to the mammal a therapeutically effective amount of a compound of Formula (IIa), wherein $R_1$ is unsubstituted $C_1$-$C_8$alkyl. In some embodiments is a method of treating cancer in a mammal in need thereof comprising administering to the mammal a therapeutically effective amount of a compound of Formula (IIa), wherein $R_1$ is —$CH_3$. In some embodiments is a method of treating cancer in a mammal in need thereof comprising administering to the mammal a therapeutically effective amount of a compound of Formula (IIa), wherein $R_1$ is —$CH_2CH_3$. In some embodiments is a method of treating cancer in a mammal in need thereof comprising administering to the mammal a therapeutically effective amount of a compound of Formula (IIa), wherein $R_1$ is substituted or unsubstituted aryl. In some embodiments is a method of treating cancer in a mammal in need thereof comprising administering to the mammal a therapeutically effective amount of a compound of Formula (IIa), wherein $R_1$ is unsubstituted phenyl.

In some embodiments is a method of treating cancer in a mammal in need thereof comprising administering to the mammal a therapeutically effective amount of a compound having the structure of Formula (III):

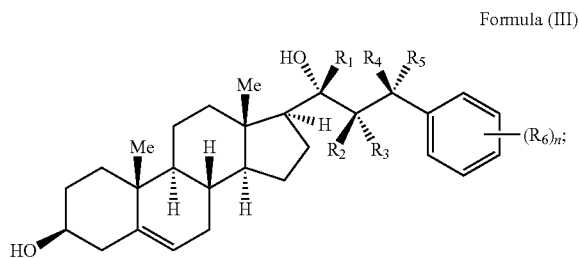

Formula (III)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
- $R_2$, $R_3$, $R_4$, and $R_5$ are independently hydrogen, deuterium, or —OH; and
- n is 0, 1, 2, or 3.

In some embodiments is a method of treating cancer in a mammal in need thereof comprising administering to the mammal a therapeutically effective amount of a compound of Formula (III), wherein n is 0. In some embodiments is a method of treating cancer in a mammal in need thereof comprising administering to the mammal a therapeutically effective amount of a compound of Formula (III), wherein n is 1 and $R_6$ is halogen. In some embodiments is a method of treating cancer in a mammal in need thereof comprising administering to the mammal a therapeutically effective amount of a compound of Formula (III), wherein n is 1 and $R_6$ is F. In some embodiments is a method of treating cancer in a mammal in need thereof comprising administering to the mammal a therapeutically effective amount of a compound of Formula (III), wherein n is 1 and $R_6$ is Cl. In some embodiments is a method of treating cancer in a mammal in need thereof comprising administering to the mammal a therapeutically effective amount of a compound of Formula (III), wherein n is 1 and $R_6$ is Br. In some embodiments is a method of treating cancer in a mammal in need thereof comprising administering to the mammal a therapeutically effective amount of a compound of Formula (III), wherein n is 1 and $R_6$ is hydroxy. In some embodiments is a method of treating cancer in a mammal in need thereof comprising administering to the mammal a therapeutically effective amount of a compound of Formula (III), wherein n is 1 and $R_6$ is substituted or unsubstituted $C_1$-$C_8$alkyl. In some embodiments is a method of treating cancer in a mammal in need thereof comprising administering to the mammal a therapeutically effective amount of a compound of Formula (III), wherein n is 1 and $R_6$ is unsubstituted $C_1$-$C_8$alkyl. In some embodiments is a method of treating cancer in a mammal in need thereof comprising administering to the mammal a therapeutically effective amount of a compound of Formula (III), wherein n is 1 and $R_6$ is substituted or unsubstituted $C_1$-$C_8$alkoxy. In some embodiments is a method of treating cancer in a mammal in need thereof comprising administering to the mammal a therapeutically effective amount of a compound of Formula (III), wherein n is 2 and each $R_6$ is halogen. In some embodiments is a method of treating cancer in a mammal in need thereof comprising administering to the mammal a therapeutically effective amount of a compound of Formula (III), wherein n is 2 and each $R_6$ is F. In some embodiments is a method of treating cancer in a mammal in need thereof comprising administering to the mammal a therapeutically effective amount of a compound of Formula (III), wherein n is 2 and each $R_6$ is Cl. In some embodiments is a method of treating cancer in a mammal in need thereof comprising administering to the mammal a therapeutically effective amount of a compound of Formula (III), wherein n is 2 and each $R_6$ is Br. In some embodiments is a method of treating cancer in a mammal in need thereof comprising administering to the mammal a therapeutically effective amount of a compound of Formula (III), wherein n is 2 and one $R_6$ is halogen and one $R_6$ is hydroxy. In some embodiments is a method of treating cancer in a mammal in need thereof comprising administering to the mammal a therapeutically effective amount of a compound of Formula (III), wherein n is 2 and each $R_6$ is hydroxy. In some embodiments is a method of treating cancer in a mammal in need thereof comprising administering to the mammal a therapeutically effective amount of a compound of Formula (III), wherein n is 2 and one $R_6$ is halogen and one $R_6$ is substituted or unsubstituted $C_1$-$C_8$alkyl. In some embodiments is a method of treating cancer in a mammal in need thereof comprising administering to the mammal a therapeutically effective amount of a compound of Formula (III), wherein n is 2 and each $R_6$ is substituted or unsubstituted $C_1$-$C_8$alkyl. In some embodiments is a method of treating cancer in a mammal in need thereof comprising administering to the mammal a therapeutically effective amount of a compound of Formula (III), wherein n is 2 and each $R_6$ is unsubstituted $C_1$-$C_8$alkyl. In some embodiments is a method of treating cancer in a mammal in need thereof comprising administering to the mammal a therapeutically effective amount of a compound of Formula (III), wherein n is 2 and one $R_6$ is halogen and one $R_6$ is substituted or unsubstituted $C_1$-$C_8$alkoxy. In some embodiments is a method of treating cancer in a mammal in need thereof comprising administering to the mammal a therapeutically effective amount of a compound of Formula (III), wherein n is 2 and each $R_6$ is substituted or unsubstituted $C_1$-$C_8$alkoxy.

In some embodiments is a method of treating cancer in a mammal in need thereof comprising administering to the mammal a therapeutically effective amount of a compound of Formula (III), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (III), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (III), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (III), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (III), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (III), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (III), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (III), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (III), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (III), wherein $R_1$ is substituted $C_1$-$C_8$alkyl. In some embodiments is a method of treating cancer in a mammal in need thereof comprising administering to the mammal a therapeutically effective amount of a compound of Formula (III), wherein $R_1$ is —$CF_3$. In some embodiments is a method of treating cancer in a mammal in need thereof comprising administering to the mammal a therapeutically effective amount of a compound of Formula (III), wherein $R_1$ is unsubstituted $C_1$-$C_8$alkyl. In some embodiments is a method of treating cancer in a mammal in need thereof comprising administering to the mammal a therapeutically effective amount of a compound of Formula (III), wherein $R_1$ is —$CH_3$. In some embodiments is a method of treating cancer in a mammal in need thereof comprising administering to the mammal a therapeutically effective amount of a compound of Formula (III), wherein $R_1$ is —$CH_2CH_3$. In some embodiments is a method of treating cancer in a mammal in need thereof comprising administering to the mammal a therapeutically effective amount of a compound of Formula (III), wherein $R_1$ is substituted or unsubstituted aryl. In some embodiments is a method of treating cancer in a mammal in need thereof comprising administering to the mammal a therapeutically effective amount of a compound of Formula (III), wherein $R_1$ is unsubstituted phenyl.

In some embodiments is a method of treating cancer in a mammal in need thereof comprising administering to the mammal a therapeutically effective amount of a compound having the structure of Formula (IIIa):

Formula (IIIa)

wherein:
  $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
  each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
  $R_2$, $R_3$, $R_4$, and $R_5$ are independently hydrogen, deuterium, or —OH; and
  n is 0, 1, or 2.

In some embodiments is a method of treating cancer in a mammal in need thereof comprising administering to the mammal a therapeutically effective amount of a compound of Formula (IIIa), wherein n is 0. In some embodiments is a method of treating cancer in a mammal in need thereof comprising administering to the mammal a therapeutically effective amount of a compound of Formula (IIIa), wherein n is 1 and $R_6$ is halogen. In some embodiments is a method of treating cancer in a mammal in need thereof comprising administering to the mammal a therapeutically effective amount of a compound of Formula (IIIa), wherein n is 1 and $R_6$ is F. In some embodiments is a method of treating cancer in a mammal in need thereof comprising administering to the mammal a therapeutically effective amount of a compound of Formula (IIIa), wherein n is 1 and $R_6$ is Cl. In some embodiments is a method of treating cancer in a mammal in need thereof comprising administering to the mammal a therapeutically effective amount of a compound of Formula (IIIa), wherein n is 1 and $R_6$ is Br. In some embodiments is a method of treating cancer in a mammal in need thereof comprising administering to the mammal a therapeutically effective amount of a compound of Formula (IIIa), wherein n is 1 and $R_6$ is hydroxy. In some embodiments is a method of treating cancer in a mammal in need thereof comprising administering to the mammal a therapeutically effective amount of a compound of Formula (IIIa), wherein n is 1 and $R_6$ is substituted or unsubstituted $C_1$-$C_8$alkyl. In some embodiments is a method of treating cancer in a mammal in need thereof comprising administering to the mammal a therapeutically effective amount of a compound of Formula (IIIa), wherein n is 1 and $R_6$ is unsubstituted $C_1$-$C_8$alkyl. In some embodiments is a method of treating cancer in a mammal in need thereof comprising administering to the mammal a therapeutically effective amount of a compound of Formula (IIIa), wherein n is 1 and $R_6$ is substituted or unsubstituted $C_1$-$C_8$alkoxy. In some embodiments is a method of treating cancer in a mammal in need thereof comprising administering to the mammal a therapeutically effective amount of a compound of Formula (IIIa), wherein n is 2 and each $R_6$ is halogen. In some embodiments is a method of treating cancer in a mammal in need thereof comprising administering to the mammal a therapeutically effective amount of a compound of Formula (IIIa), wherein n is 2 and each $R_6$ is F. In some embodiments is a method of treating cancer in a mammal in need thereof comprising administering to the mammal a therapeutically effective amount of a compound of Formula (IIIa), wherein n is 2 and each $R_6$ is Cl. In some embodiments is a method of treating cancer in a mammal in need thereof comprising administering to the mammal a therapeutically effective amount of a compound of Formula (IIIa), wherein n is 2 and each $R_6$ is Br. In some embodiments is a method of treating cancer in a mammal in need thereof comprising administering to the mammal a therapeutically effective amount of a compound of Formula (IIIa), wherein n is 2 and one $R_6$ is halogen and one $R_6$ is hydroxy. In some embodiments is a method of treating cancer in a mammal in need thereof comprising administering to the mammal a therapeutically effective amount of a compound of Formula (IIIa), wherein n is 2 and each $R_6$ is hydroxy. In some embodiments is a method of treating cancer in a mammal in need thereof comprising administering to the mammal a therapeutically effective amount of a compound of Formula (IIIa), wherein n is 2 and one $R_6$ is halogen and one $R_6$ is substituted or unsubstituted $C_1$-$C_8$alkyl. In some embodiments is a method of treating cancer in a mammal in need thereof comprising administering to the mammal a therapeutically effective amount of a compound of Formula (IIIa), wherein n is 2 and each $R_6$ is substituted or unsubstituted $C_1$-$C_8$alkyl. In some embodiments is a method of treating cancer in a mammal in need thereof comprising administering to the mammal a therapeutically effective amount of a compound of Formula (IIIa), wherein n is 2 and each $R_6$ is unsubstituted $C_1$-$C_8$alkyl. In some embodiments is a method of treating cancer in a mammal in need thereof comprising administering to the mammal a therapeutically effective amount of a compound of Formula (IIIa), wherein n is 2 and one $R_6$ is halogen and one $R_6$ is substituted or unsubstituted $C_1$-$C_8$alkoxy. In some embodiments is a method of treating cancer in a mammal in need thereof comprising administering to the mammal a therapeutically effective amount of a compound of Formula (IIIa), wherein n is 2 and each $R_6$ is substituted or unsubstituted $C_1$-$C_8$alkoxy.

In some embodiments is a method of treating cancer in a mammal in need thereof comprising administering to the mammal a therapeutically effective amount of a compound of Formula (IIIa), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (IIIa), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (IIIa), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (IIIa), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (IIIa), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (IIIa), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (IIIa), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (IIIa), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (IIIa), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (IIIa), wherein $R_1$ is substituted $C_1$-$C_8$alkyl. In some embodiments is a method of treating cancer in a mammal in need thereof comprising administering to the mammal a therapeutically effective amount of a compound of Formula (IIIa), wherein $R_1$ is —$CF_3$. In some embodiments is a method of treating cancer in a mammal in need thereof comprising administering to the mammal a therapeutically effective amount of a compound of Formula (IIIa), wherein $R_1$ is unsubstituted $C_1$-$C_8$alkyl. In some embodiments is a method of treating cancer in a mammal in need thereof comprising administering to the mammal a therapeutically effective amount of a compound of Formula (IIIa), wherein $R_1$ is —$CH_3$. In some embodiments is a method of treating cancer in a mammal in need thereof comprising administering to the mammal a therapeutically effective amount of a compound of Formula (IIIa), wherein $R_1$ is —$CH_2CH_3$. In some embodiments is a method of treating cancer in a mammal in need thereof comprising administering to the mammal a therapeutically effective amount of a compound of Formula (IIIa), wherein $R_1$ is substituted or unsubstituted aryl. In some embodiments is a method of treating cancer in a mammal in need thereof comprising administering to the mammal a therapeutically effective amount of a compound of Formula (IIIa), wherein $R_1$ is unsubstituted phenyl.

In some embodiments is a method of treating cancer in a mammal in need thereof comprising administering to the mammal a therapeutically effective amount of a compound having the structure of Formula (IV):

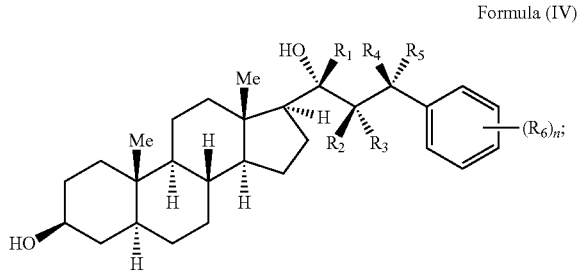

Formula (IV)

wherein:
- $R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;
- each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;
- $R_2$, $R_3$, $R_4$, and $R_5$ are independently hydrogen, deuterium, or —OH; and
- n is 0, 1, 2, or 3.

In some embodiments is a method of treating cancer in a mammal in need thereof comprising administering to the mammal a therapeutically effective amount of a compound of Formula (IV), wherein n is 0. In some embodiments is a method of treating cancer in a mammal in need thereof comprising administering to the mammal a therapeutically effective amount of a compound of Formula (IV), wherein n is 1 and $R_6$ is halogen. In some embodiments is a method of treating cancer in a mammal in need thereof comprising administering to the mammal a therapeutically effective amount of a compound of Formula (IV), wherein n is 1 and $R_6$ is F. In some embodiments is a method of treating cancer in a mammal in need thereof comprising administering to the mammal a therapeutically effective amount of a compound of Formula (IV), wherein n is 1 and $R_6$ is Cl. In some embodiments is a method of treating cancer in a mammal in need thereof comprising administering to the mammal a therapeutically effective amount of a compound of Formula (IV), wherein n is 1 and $R_6$ is Br. In some embodiments is a method of treating cancer in a mammal in need thereof comprising administering to the mammal a therapeutically effective amount of a compound of Formula (IV), wherein n is 1 and $R_6$ is hydroxy. In some embodiments is a method of treating cancer in a mammal in need thereof comprising administering to the mammal a therapeutically effective amount of a compound of Formula (IV), wherein n is 1 and $R_6$ is substituted or unsubstituted $C_1$-$C_8$alkyl. In some embodiments is a method of treating cancer in a mammal in need thereof comprising administering to the mammal a therapeutically effective amount of a compound of Formula (IV), wherein n is 1 and $R_6$ is unsubstituted $C_1$-$C_8$alkyl. In some embodiments is a method of treating cancer in a mammal in need thereof comprising administering to the mammal a therapeutically effective amount of a compound of Formula (IV), wherein n is 1 and $R_6$ is substituted or unsubstituted $C_1$-$C_8$alkoxy. In some embodiments is a method of treating cancer in a mammal in need thereof comprising administering to the mammal a therapeutically effective amount of a compound of Formula (IV), wherein n is 2 and each $R_6$ is halogen. In some embodiments is a method of treating cancer in a mammal in need thereof comprising administering to the mammal a therapeutically effective amount of a compound of Formula (IV), wherein n is 2 and each $R_6$ is F. In some embodiments is a method of treating cancer in a mammal in need thereof comprising administering to the mammal a therapeutically effective amount of a compound of Formula (IV), wherein n is 2 and each $R_6$ is Cl. In some embodiments is a method of treating cancer in a mammal in need thereof comprising administering to the mammal a therapeutically effective amount of a compound of Formula (IV), wherein n is 2 and each $R_6$ is Br. In some embodiments is a method of treating cancer in a mammal in need thereof comprising administering to the mammal a therapeutically effective amount of a compound of Formula (IV), wherein n is 2 and one $R_6$ is halogen and one $R_6$ is hydroxy. In some embodiments is a method of treating cancer in a mammal in need thereof comprising administering to the mammal a therapeutically effective amount of a compound of Formula (IV), wherein n is 2 and each $R_6$ is hydroxy. In some embodiments is a method of treating cancer in a mammal in need thereof comprising administering to the mammal a therapeutically effective amount of a compound of Formula (IV), wherein n is 2 and one $R_6$ is halogen and one $R_6$ is substituted or unsubstituted $C_1$-$C_8$alkyl. In some embodiments is a method of treating cancer in a mammal in need thereof comprising administering to the mammal a therapeutically effective amount of a compound of Formula (IV), wherein n is 2 and each $R_6$ is substituted or unsubstituted $C_1$-$C_8$alkyl. In some embodiments is a method of treating cancer in a mammal in need thereof comprising administering to the mammal a therapeutically effective amount of a compound of Formula (IV), wherein n is 2 and each $R_6$ is unsubstituted $C_1$-$C_8$alkyl. In some embodiments is a method of treating cancer in a mammal in need thereof comprising administering to the mammal a therapeutically effective amount of a compound of Formula (IV), wherein n is 2 and one $R_6$ is halogen and one $R_6$ is substituted or unsubstituted $C_1$-$C_8$alkoxy. In some embodiments is a method of treating cancer in a mammal in need thereof comprising administering to the mammal a therapeutically effective amount of a compound of Formula (IV), wherein n is 2 and each $R_6$ is substituted or unsubstituted $C_1$-$C_8$alkoxy.

In some embodiments is a method of treating cancer in a mammal in need thereof comprising administering to the mammal a therapeutically effective amount of a compound of Formula (IV), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (IV), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (IV), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (IV), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (IV), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (IV), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (IV), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (IV), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (IV), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (IV), wherein $R_1$ is substituted $C_1$-$C_8$alkyl. In some embodiments is a method of treating cancer in a mammal in need thereof comprising administering to the mammal a therapeutically effective amount of a compound of Formula (IV), wherein $R_1$ is —$CF_3$. In some embodiments is a method of treating cancer in a mammal in need thereof comprising administering to the mammal a therapeutically effective amount of a compound of Formula (IV), wherein $R_1$ is unsubstituted $C_1$-$C_8$alkyl. In some embodiments is a method of treating cancer in a mammal in need thereof comprising administering to the mammal a therapeutically effective amount of a compound of Formula (IV), wherein $R_1$ is —$CH_3$. In some embodiments is a method of treating cancer in a mammal in need thereof comprising administering to the mammal a therapeutically effective amount of a compound of Formula (IV), wherein $R_1$ is —$CH_2CH_3$. In some embodiments is a method of treating cancer in a mammal in need thereof comprising administering to the mammal a therapeutically effective amount of a compound of Formula (IV), wherein $R_1$ is substituted or unsubstituted aryl. In some embodiments is a method of treating cancer in a mammal in need thereof comprising administering to the mammal a therapeutically effective amount of a compound of Formula (IV), wherein $R_1$ is unsubstituted phenyl.

In some embodiments is a method of treating cancer in a mammal in need thereof comprising administering to the mammal a therapeutically effective amount of a compound having the structure of Formula (IVa):

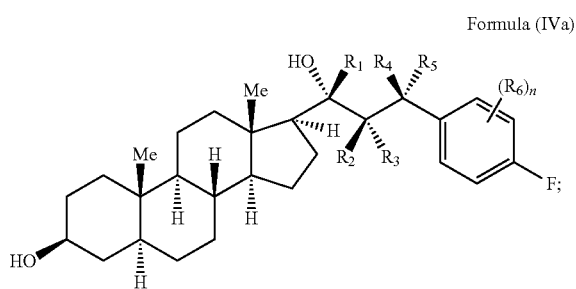

Formula (IVa)

wherein:
$R_1$ is substituted or unsubstituted $C_1$-$C_8$alkyl, substituted or unsubstituted $C_1$-$C_8$alkenyl, substituted or unsubstituted $C_1$-$C_8$alkynyl, substituted or unsubstituted aryl, substituted or unsubstituted heteroaryl, or substituted or unsubstituted —$C_1$-$C_4$alkylaryl;

each $R_6$ is independently halogen, hydroxy, substituted or unsubstituted $C_1$-$C_8$alkyl, substituted or unsubstituted $C_1$-$C_8$alkoxy, substituted or unsubstituted $C_1$-$C_8$heteroalkyl, substituted or unsubstituted $C_3$-$C_8$cycloalkyl, substituted or unsubstituted aryl, or substituted or unsubstituted heteroaryl;

$R_2$, $R_3$, $R_4$, and $R_5$ are independently hydrogen, deuterium, or —OH; and n is 0, 1, or 2.

In some embodiments is a method of treating cancer in a mammal in need thereof comprising administering to the mammal a therapeutically effective amount of a compound of Formula (IVa), wherein n is 0. In some embodiments is a method of treating cancer in a mammal in need thereof comprising administering to the mammal a therapeutically effective amount of a compound of Formula (IVa), wherein n is 1 and $R_6$ is halogen. In some embodiments is a method of treating cancer in a mammal in need thereof comprising administering to the mammal a therapeutically effective amount of a compound of Formula (IVa), wherein n is 1 and $R_6$ is F. In some embodiments is a method of treating cancer in a mammal in need thereof comprising administering to the mammal a therapeutically effective amount of a compound of Formula (IVa), wherein n is 1 and $R_6$ is Cl. In some embodiments is a method of treating cancer in a mammal in need thereof comprising administering to the mammal a therapeutically effective amount of a compound of Formula (IVa), wherein n is 1 and $R_6$ is Br. In some embodiments is a method of treating cancer in a mammal in need thereof comprising administering to the mammal a therapeutically effective amount of a compound of Formula (IVa), wherein n is 1 and $R_6$ is hydroxy. In some embodiments is a method of treating cancer in a mammal in need thereof comprising administering to the mammal a therapeutically effective amount of a compound of Formula (IVa), wherein n is 1 and $R_6$ is substituted or unsubstituted $C_1$-$C_8$alkyl. In some embodiments is a method of treating cancer in a mammal in need thereof comprising administering to the mammal a therapeutically effective amount of a compound of Formula (IVa), wherein n is 1 and $R_6$ is unsubstituted $C_1$-$C_8$alkyl. In some embodiments is a method of treating cancer in a mammal in need thereof comprising administering to the mammal a therapeutically effective amount of a compound of Formula (IVa), wherein n is 1 and $R_6$ is substituted or unsubstituted $C_1$-$C_8$alkoxy. In some embodiments is a method of treating cancer in a mammal in need thereof comprising administering to the mammal a therapeutically effective amount of a compound of Formula (IVa), wherein n is 2 and each $R_6$ is halogen. In some embodiments is a method of treating cancer in a mammal in need thereof comprising administering to the mammal a therapeutically effective amount of a compound of Formula (IVa), wherein n is 2 and each $R_6$ is F. In some embodiments is a method of treating cancer in a mammal in need thereof comprising administering to the mammal a therapeutically effective amount of a compound of Formula (IVa), wherein n is 2 and each $R_6$ is Cl. In some embodiments is a method of treating cancer in a mammal in need thereof comprising administering to the mammal a therapeutically effective amount of a compound of Formula (IVa), wherein n is 2 and each $R_6$ is Br. In some embodiments is a method of treating cancer in a mammal in need thereof comprising administering to the mammal a therapeutically effective amount of a compound of Formula (IVa), wherein n is 2 and one $R_6$ is halogen and one $R_6$ is hydroxy. In some embodiments is a method of treating cancer in a mammal in need thereof comprising administering to the mammal a therapeutically effective amount of a compound of Formula (IVa), wherein n is 2 and each $R_6$ is hydroxy. In some embodiments is a method of treating cancer in a mammal in need thereof comprising administering to the mammal a therapeutically effective amount of a compound of Formula (IVa), wherein n is 2 and one $R_6$ is halogen and one $R_6$ is substituted or unsubstituted $C_1$-$C_8$alkyl. In some embodiments is a method of treating cancer in a mammal in need thereof comprising administering to the mammal a therapeutically effective amount of a compound of Formula (IVa), wherein n is 2 and each $R_6$ is substituted or unsubstituted $C_1$-$C_8$alkyl. In some embodiments is a method of treating cancer in a mammal in need thereof comprising administering to the mammal a therapeutically effective amount of a compound of Formula (IVa), wherein n is 2 and each $R_6$ is unsubstituted $C_1$-$C_8$alkyl. In some embodiments is a method of treating cancer in a mammal in need thereof comprising administering to the mammal a therapeutically effective amount of a compound of Formula (IVa), wherein n is 2 and one $R_6$ is halogen and one $R_6$ is substituted or unsubstituted $C_1$-$C_8$alkoxy. In some embodiments is a method of treating cancer in a mammal in need thereof comprising administering to the mammal a therapeutically effective amount of a compound of Formula (IVa), wherein n is 2 and each $R_6$ is substituted or unsubstituted $C_1$-$C_8$alkoxy.

In some embodiments is a method of treating cancer in a mammal in need thereof comprising administering to the mammal a therapeutically effective amount of a compound of Formula (IVa), wherein $R_2$, $R_3$, $R_4$, and $R_5$ are each deuterium. In some embodiments is a method of treating cancer in a mammal in need thereof comprising administering to the mammal a therapeutically effective amount of a compound of Formula (IVa), wherein $R_2$, $R_3$, $R_4$, and $R_5$ are each hydrogen. In some embodiments is a method of treating cancer in a mammal in need thereof comprising administering to the mammal a therapeutically effective amount of a compound of Formula (IVa), wherein $R_2$ is —OH, and $R_3$, $R_4$, and $R_5$ are each hydrogen. In some embodiments is a method of treating cancer in a mammal in need thereof comprising administering to the mammal a therapeutically effective amount of a compound of Formula (IVa), wherein $R_3$ is —OH, and $R_2$, $R_4$, and $R_5$ are each hydrogen. In some embodiments is a method of treating cancer in a mammal in need thereof comprising administering to the mammal a therapeutically effective amount of a compound of Formula (IVa), wherein $R_2$ and $R_4$ are each —OH, and $R_3$ and $R_5$ are each hydrogen. In some embodiments is a method of treating cancer in a mammal in need thereof comprising administering to the mammal a therapeutically effective amount of a compound of Formula (IVa), wherein $R_2$ and $R_5$ are each —OH, and $R_3$ and $R_4$ are each hydrogen. In some embodiments is a method of treating cancer in a mammal in need thereof comprising administering to the mammal a therapeutically effective amount of a compound of Formula (IVa), wherein $R_3$ and $R_4$ are each —OH, and $R_2$ and $R_5$ are each hydrogen. In some embodiments is a method of treating cancer in a mammal in need thereof comprising administering to the mammal a therapeutically effective amount of a compound of Formula (IVa), wherein $R_3$ and $R_5$ are each —OH, and $R_2$ and $R_4$ are each hydrogen.

In some embodiments is a method of treating cancer in a mammal in need thereof comprising administering to the mammal a therapeutically effective amount of a compound of Formula (IVa), wherein $R_1$ is substituted or unsubstituted $C_1$-$C_8$alkyl. In some embodiments is a method of treating cancer in a mammal in need thereof comprising administering to the mammal a therapeutically effective amount of a compound of Formula (IVa), wherein $R_1$ is substituted $C_1$-$C_8$alkyl. In some embodiments is a method of treating cancer in a mammal in need thereof comprising administering to the mammal a therapeutically effective amount of a compound of Formula (IVa), wherein $R_1$ is —$CF_3$. In some embodiments is a method of treating cancer in a mammal in need thereof comprising administering to the mammal a therapeutically effective amount of a compound of Formula (IVa), wherein $R_1$ is unsubstituted $C_1$-$C_8$alkyl. In some embodiments is a method of treating cancer in a mammal in need thereof comprising administering to the mammal a therapeutically effective amount of a compound of Formula (IVa), wherein $R_1$ is —$CH_3$. In some embodiments is a method of treating cancer in a mammal in need thereof comprising administering to the mammal a therapeutically effective amount of a compound of Formula (IVa), wherein $R_1$ is —$CH_2CH_3$. In some embodiments is a method of treating cancer in a mammal in need thereof comprising administering to the mammal a therapeutically effective amount of a compound of Formula (IVa), wherein $R_1$ is substituted or unsubstituted aryl. In some embodiments is a method of treating cancer in a mammal in need thereof comprising administering to the mammal a therapeutically effective amount of a compound of Formula (IVa), wherein $R_1$ is unsubstituted phenyl.

In some embodiments is a method of treating cancer in a mammal in need thereof comprising administering to the mammal a therapeutically effective amount of a compound having a structure selected from:

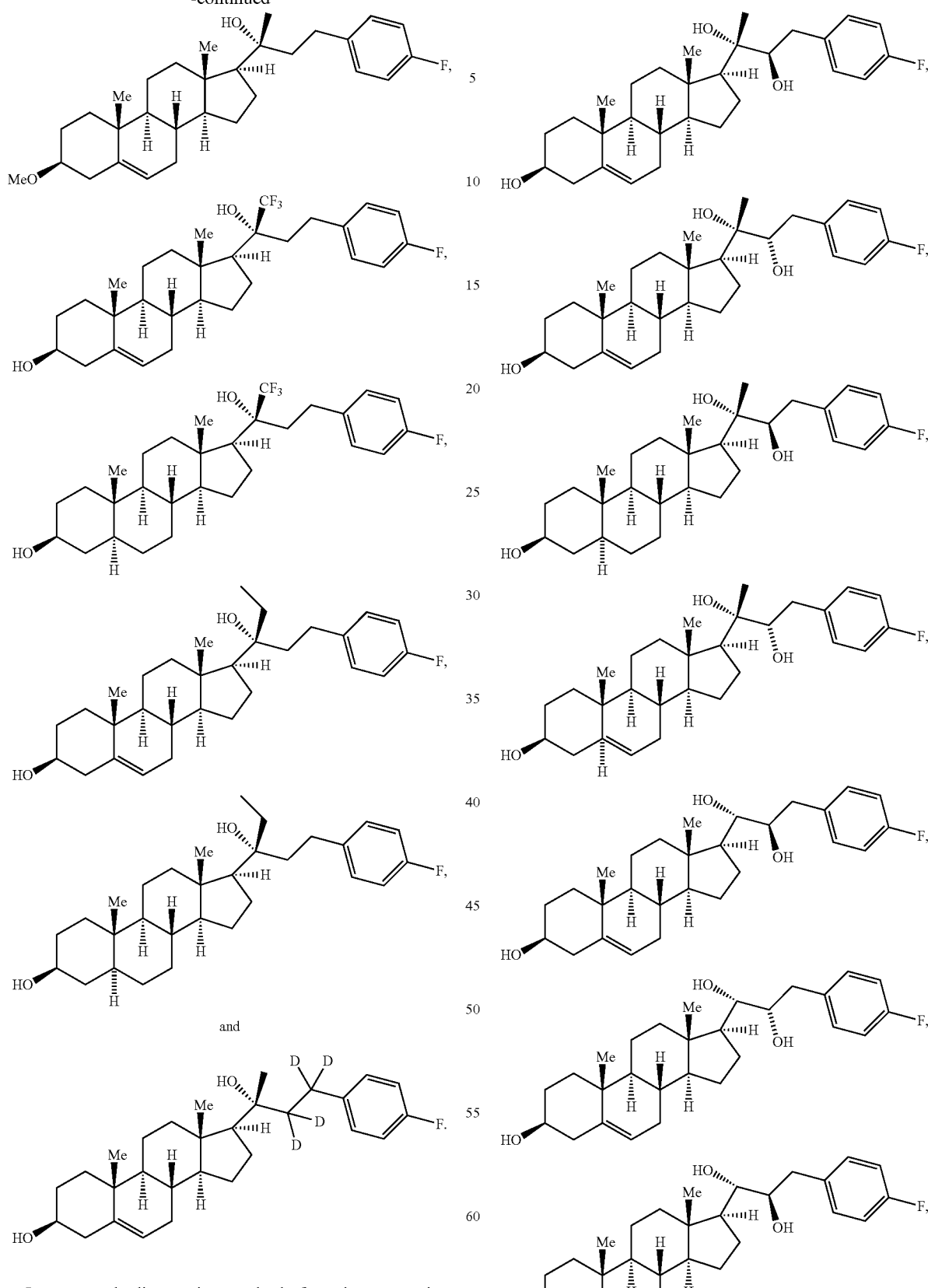
In some embodiments is a method of treating cancer in a mammal in need thereof comprising administering to the mammal a therapeutically effective amount of a compound having a structure selected from:

61
-continued
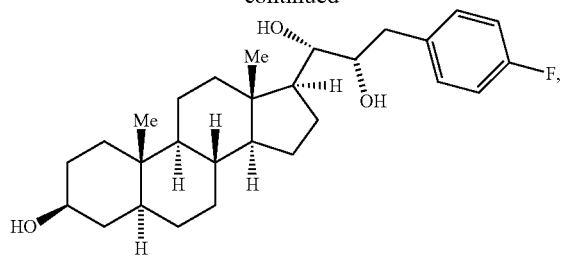
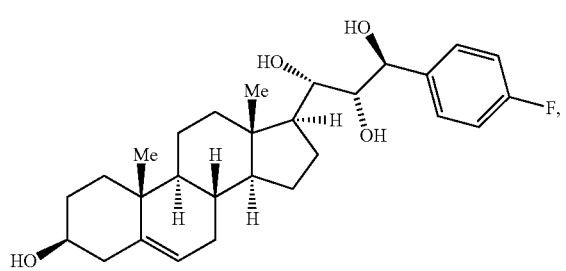
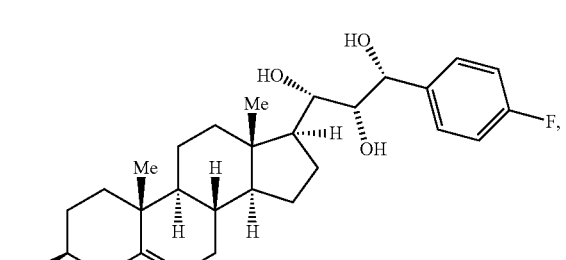
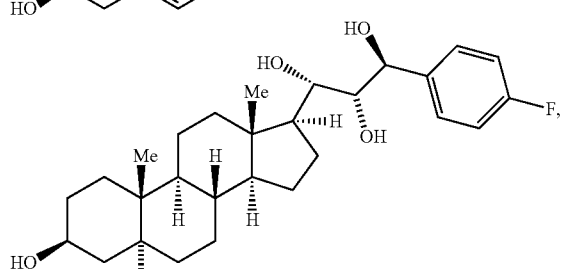
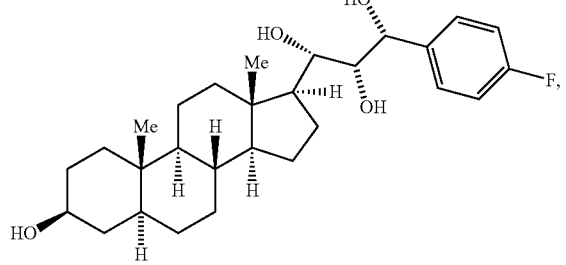
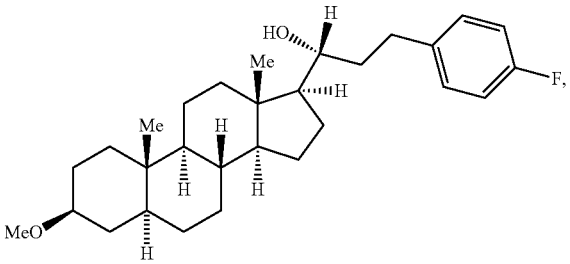
62
-continued
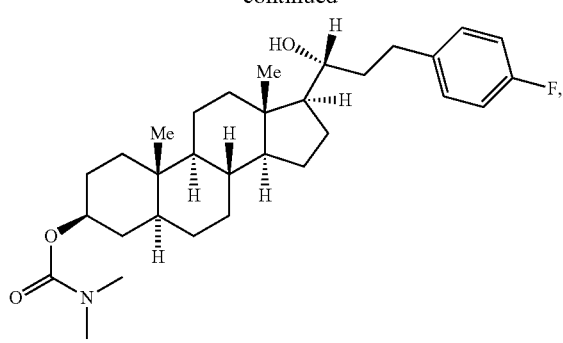
and
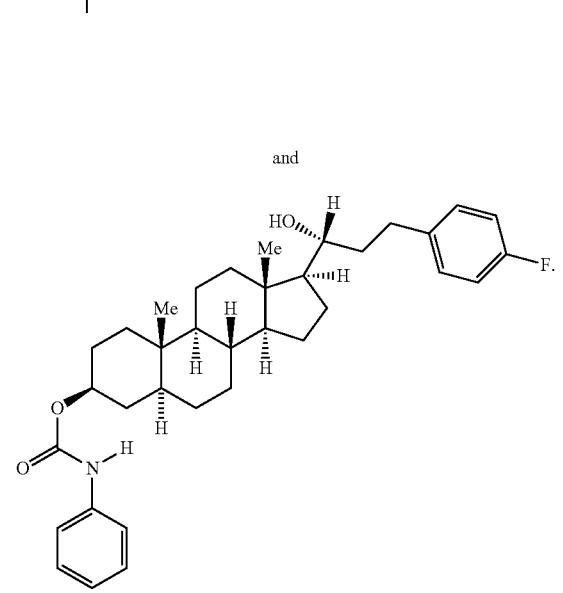
In some embodiments is a method of treating cancer in a mammal in need thereof comprising administering to the mammal a therapeutically effective amount of a compound having a structure selected from:
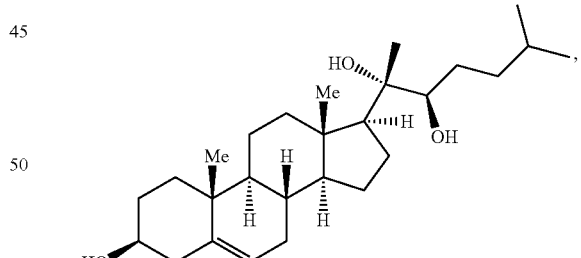
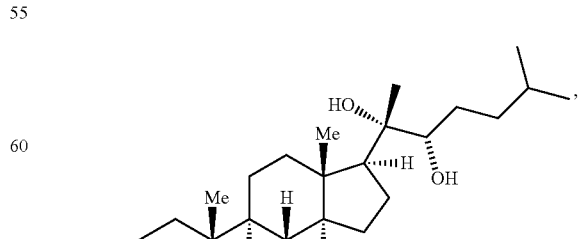

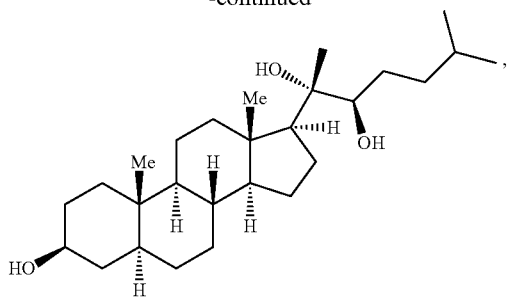
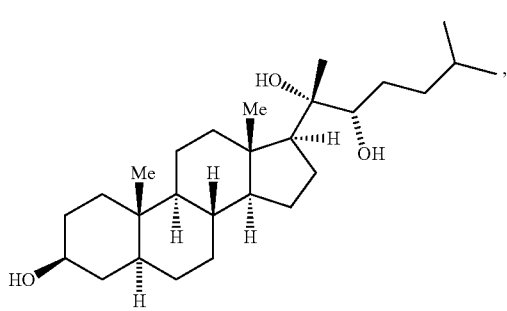
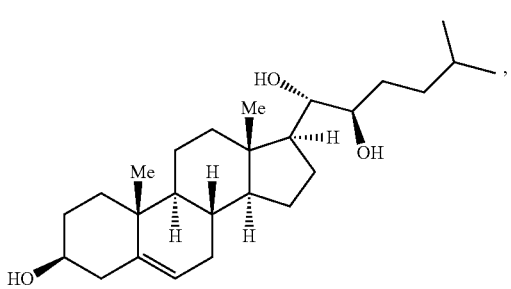
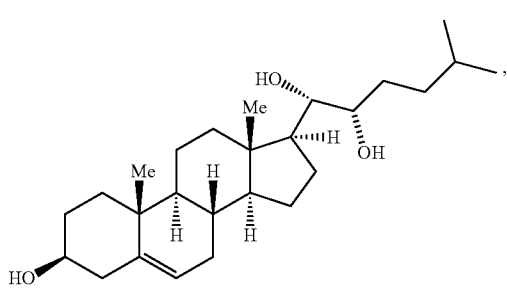
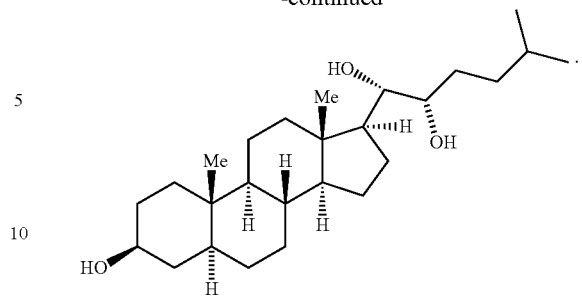
In some embodiments is a method of treating cancer in a mammal in need thereof comprising administering to the mammal a therapeutically effective amount of a compound having a structure selected from:
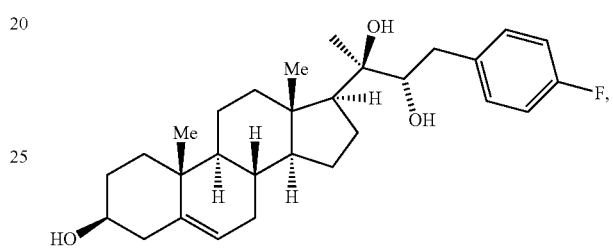
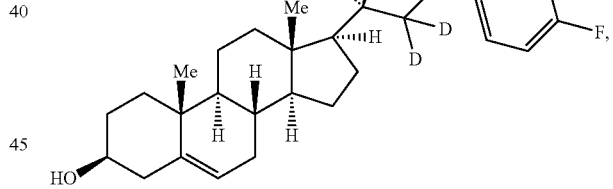
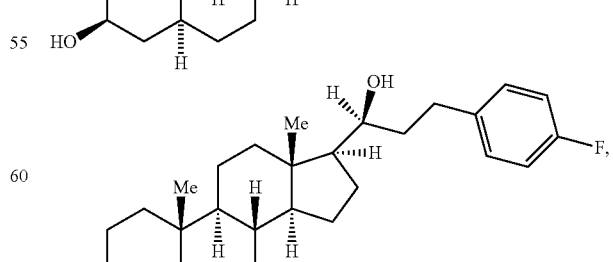
and -continued

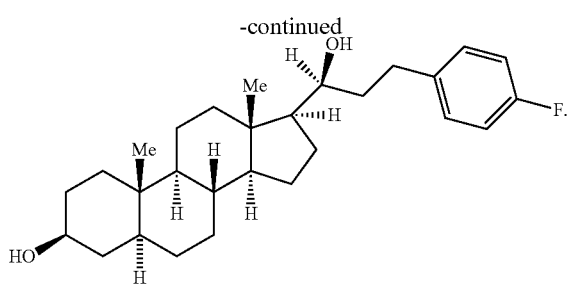

In some embodiments is a method of treating cancer in a mammal in need thereof comprising administering to the mammal a therapeutically effective amount of a compound having a structure selected from:

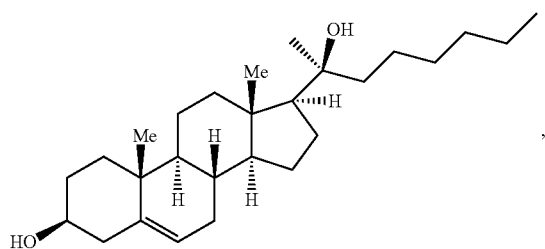

and

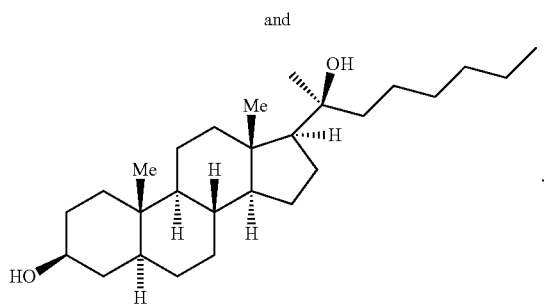

Further provided herein, for any of the aforementioned embodiments of methods of treating cancer in a mammal in need thereof comprising administering to the mammal a therapeutically effective amount of a comprising a compound of Formula (I), (Ia), (Ib), (II), (IIa), (III), (IIIa), (IV), or (IVa), is a compound of Formula (I), (Ia), (Ib), (II), (IIa), (III), (IIIa), (IV), or (IVa) for use in treating cancer. Also provided herein, for any of the aforementioned embodiments of methods of treating cancer in a mammal in need thereof comprising administering to the mammal a therapeutically effective amount of a comprising a compound of Formula (I), (Ia), (Ib), (II), (IIa), (III), (IIIa), (IV), or (IVa), is the use of a compound of Formula (I), (Ia), (Ib), (II), (IIa), (III), (IIIa), (IV), or (IVa) for the manufacture of a medicament for the treatment of cancer.

Also provided herein, in some embodiments, is a method for inhibiting a Hedgehog signaling pathway in a cell, the method comprising contacting the cell with one or more compounds of Formula (I), (Ia), (Ib), (II), (IIa), (III), (IIIa), (IV), or (IVa) in a sufficient amount to inhibit the Hedgehog signaling.

Also provided herein, in some embodiments, is a method of inhibiting tumorigenesis through interfering with tumorigenic signaling pathways in a mammal comprising locally or systemically administering to the mammal a therapeutically effective amount of a compound of Formula (I), (Ia), (Ib), (II), (IIa), (III), (IIIa), (IV), or (IVa).

Also provided herein, in some embodiments, is a method of treating a disease, disorder or condition associated with an aberrant regulation of a Hedgehog pathway in a mammal comprising locally or systemically administering to the mammal a therapeutically effective amount of a compound of Formula (I), (Ia), (Ib), (II), (IIa), (III), (IIIa), (IV), or (IVa). In some embodiments is a method of treating a disease, disorder or condition associated with an aberrant regulation of a Hedgehog pathway in a mammal comprising locally or systemically administering to the mammal a therapeutically effective amount of a compound of Formula (I), (Ia), (Ib), (II), (IIa), (III), (IIIa), (IV), or (IVa); wherein the disease is cancer. In some embodiments is a method of treating a disease, disorder or condition associated with an aberrant regulation of a Hedgehog pathway in a mammal comprising locally or systemically administering to the mammal a therapeutically effective amount of a compound of Formula (I), (Ia), (Ib), (II), (IIa), (III), (IIIa), (IV), or (IVa); wherein the disease is cancer and the cancer is selected from basal cell carcinoma, melanoma, leukemia, multiple myeloma, stomach cancer, pancreatic cancer, bladder cancer, prostate cancer, ovarian cancer, bone cancer, brain cancer, lung cancer, breast cancer, and skin cancer.

Synthesis of the Compounds

The compounds used in the reactions described herein are made according to organic synthesis techniques, starting from commercially available chemicals and/or from compounds described in the chemical literature.

Compounds of Formula (I), (Ia), (Ib), (II), (IIa), (III), (IIIa), (IV), or (IVa) are prepared by the general synthetic routes described below in Schemes 1-4, wherein $R_1$, $R_6$, and n, are as defined herein, and $Q^1$, $Q^2$, and $Q^3$ are defined such that compounds of formula (D), formula (H), and formula (T) are compounds of Formulas (I), (Ia), (II), (III), (IIIa), (IV), (IVa), (V), (Va), (VI), (VIa), (VII), (VIIa), or (VIII).

Scheme 1
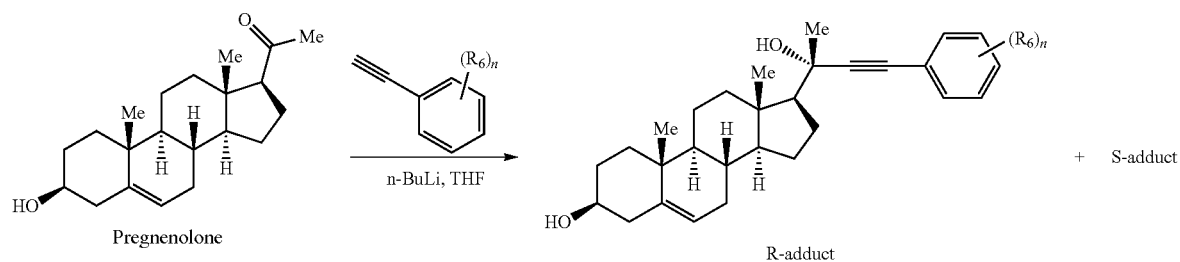
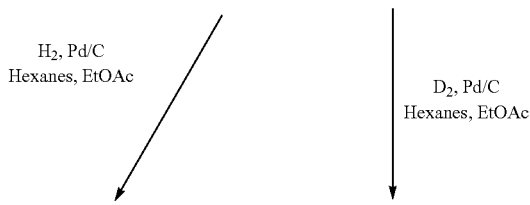
A method for preparing compounds described herein is provided in Scheme 1. Addition of an ethynylbenzene to pregnenolone affords a mixture of addition products, R-adduct and S-adduct. Reduction of the R-adduct with $H_2$ or $D_2$ with palladium on carbon catalyst gives the hydrogen or deuterium product, respectively.
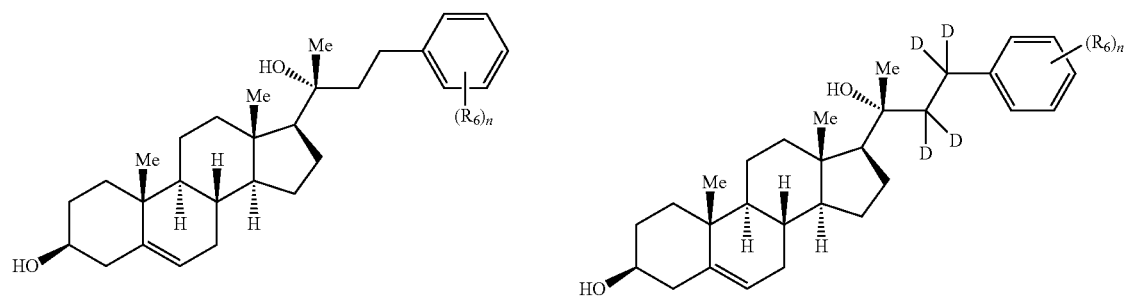
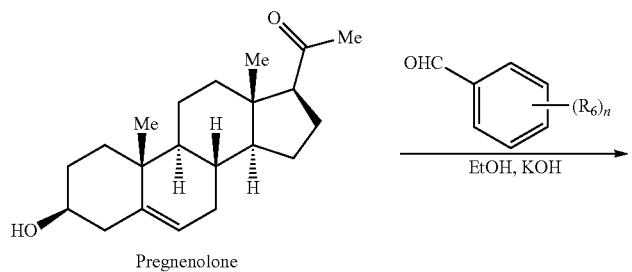

-continued
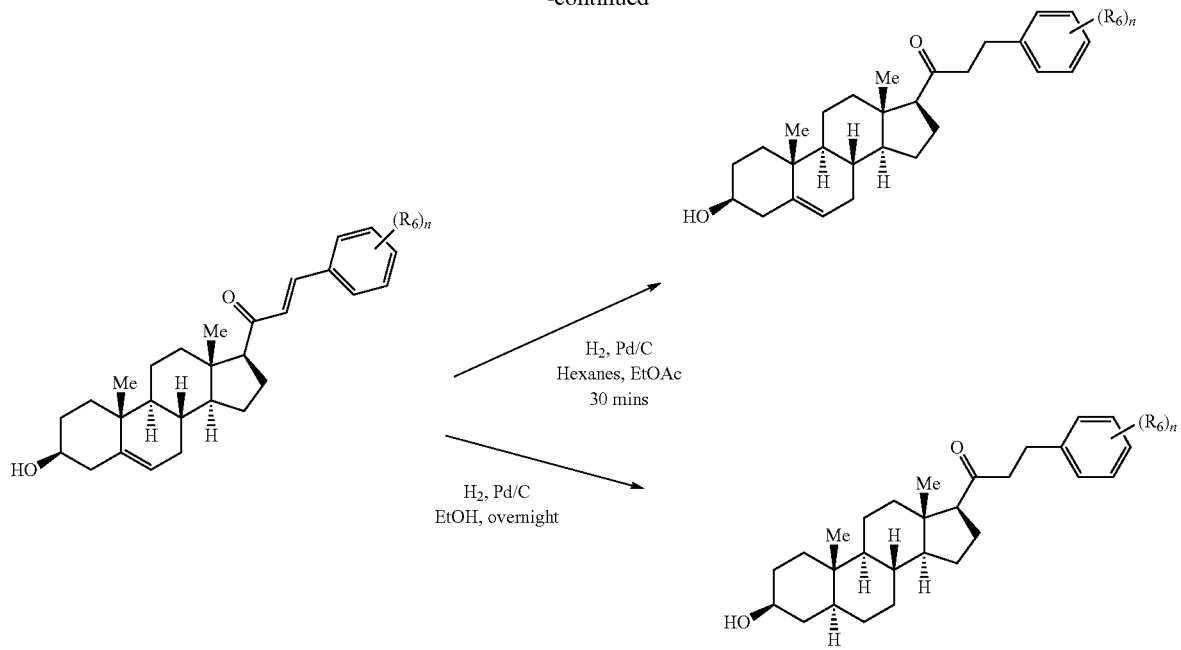
Another method for preparing compounds described herein is provided in Scheme 2. Aldol condensation of a benzaldehyde and pregnenolone affords the ketone. Reduction of the ketone with $H_2$ and palladium on carbon catalyst under varying conditions yields the partially unsaturated or fully saturated products, respectively.
Scheme 3
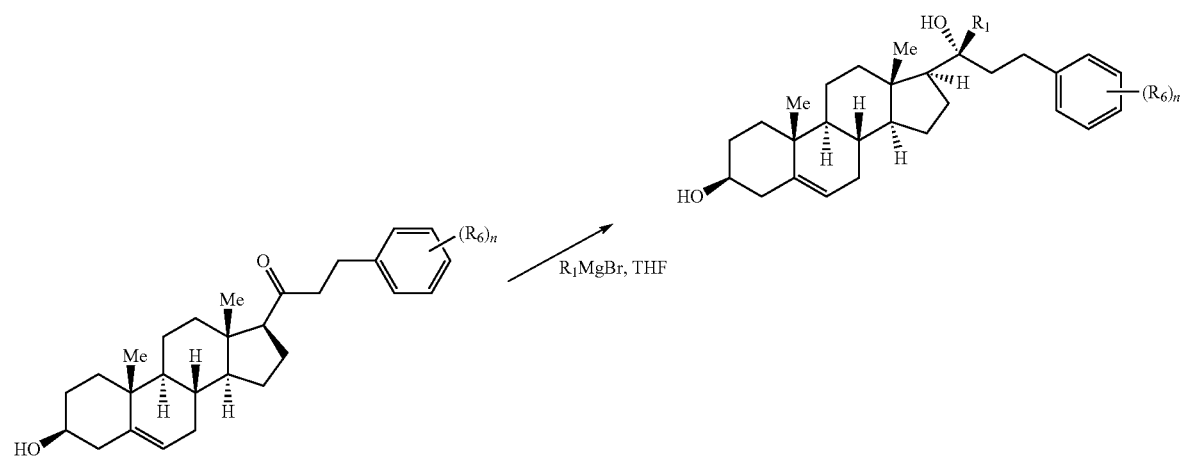

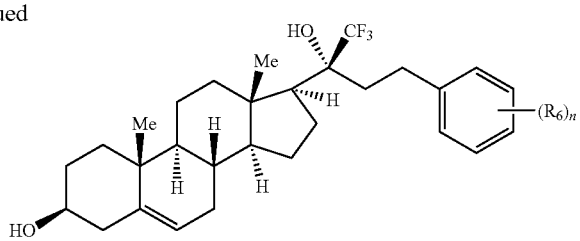

Another method for preparing compounds described herein is provided in Scheme 3. The addition of a Grignard reagent to the partially unsaturated ketone of Scheme 2 affords the tertiary alcohol. Alternatively, the trifluormethyl adduct is prepared in a two step procedure outlined above.

Scheme 4

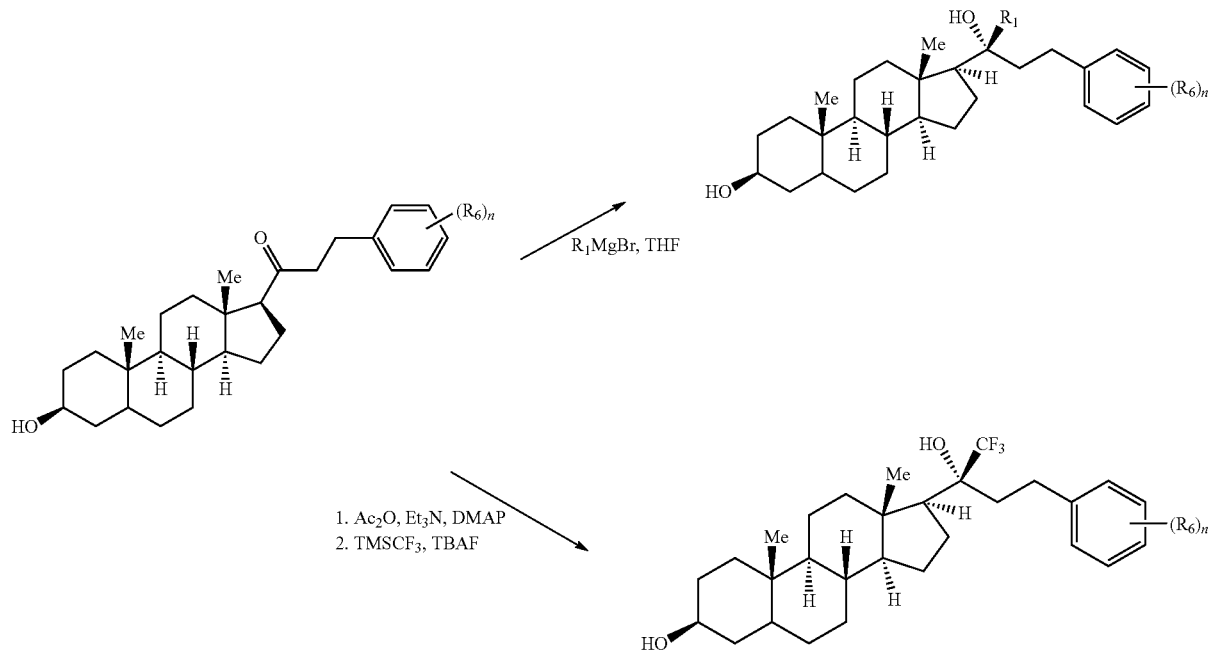

Another method for preparing compounds described herein is provided in Scheme 4. The addition of a Grignard reagent to the saturated ketone of Scheme 2 affords the tertiary alcohol. Alternatively, the trifluormethyl adduct is prepared in a two step procedure outlined above.

Routes of Administration

Suitable routes of administration include, but are not limited to, oral, intravenous, aerosol, parenteral, ophthalmic, pulmonary, transmucosal, transdermal, nasal, and topical administration. In addition, by way of example only, parenteral delivery includes intramuscular, subcutaneous, intravenous, intramedullary injections, as well as intrathecal, direct intraventricular, intraperitoneal, intralymphatic, and/or intranasal injections.

In some embodiments, a compound of Formula (I), (Ia), (Ib), (II), (IIa), (III), (IIIa), (IV), or (IVa) is administered orally, intravenously, intraperitoneally, subcutaneously, or as an aerosol. In some embodiments, a compound of Formula (I), (Ia), (Ib), (II), (IIa), (III), (IIIa), (IV), or (IVa) is administered orally, intravenously, intraperitoneally, or subcutaneously. In some embodiments, a compound of Formula (I), (Ia), (Ib), (II), (IIa), (III), (IIIa), (IV), or (IVa) is administered orally. In some embodiments, a compound of Formula (I), (Ia), (Ib), (II), (IIa), (III), (IIIa), (IV), or (IVa) is administered intravenously. In some embodiments, a compound of Formula (I), (Ia), (Ib), (II), (IIa), (III), (IIIa), (IV), or (IVa) is administered intraperitoneally. In some embodiments, a compound of Formula (I), (Ia), (Ib), (II), (IIa), (III), (IIIa), (IV), or (IVa) is administered subcutaneously. In some embodiments, a compound of Formula (I), (Ia), (Ib), (II), (IIa), (III), (IIIa), (IV), or (IVa) is administered as an aerosol.

In certain embodiments, a compound of Formula (I), (Ia), (Ib), (II), (IIa), (III), (IIIa), (IV), or (IVa) is administered in a local rather than systemic manner, for example, via topical application of the compound directly on to skin, or intravenously, or subcutaneously, often in a depot preparation or sustained release formulation. In specific embodiments, long acting formulations are administered by implantation (for example subcutaneously or intramuscularly) or by intramuscular injection. In yet other embodiments, the compound as described herein is provided in the form of a rapid release formulation, in the form of an extended release formulation, or in the form of an intermediate release formulation. In yet other embodiments, the compound described herein is administered topically (e.g., as a patch, an ointment, or in combination with a wound dressing, or as a wash or a spray). In alternative embodiments, a formulation is administered systemically (e.g., by injection, or as a pill).

Pharmaceutical Compositions/Formulations

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins1999), herein incorporated by reference for such disclosure.

Provided herein are pharmaceutical compositions that include a compound of Formula (I), (Ia), (Ib), (II), (IIa), (III), (IIIa), (IV), or (IVa) and at least one pharmaceutically acceptable inactive ingredient. In some embodiments, the compounds described herein are administered as pharmaceutical compositions in which compounds of Formula (I), (Ia), (Ib), (II), (IIa), (III), (IIIa), (IV), or (IVa) are mixed with other active ingredients, as in combination therapy. In other embodiments, the pharmaceutical compositions include other medicinal or pharmaceutical agents, carriers, adjuvants, preserving, stabilizing, wetting or emulsifying agents, solution promoters, salts for regulating the osmotic pressure, and/or buffers. In yet other embodiments, the pharmaceutical compositions include other therapeutically valuable substances.

A pharmaceutical composition, as used herein, refers to a mixture of a compound of Formula (I), (Ia), (Ib), (II), (IIa), (III), (IIIa), (IV), or (IVa) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

Pharmaceutical compositions including a compound of Formula (I), (Ia), (Ib), (II), (IIa), (III), (IIIa), (IV), or (IVa) are manufactured in a conventional manner, such as, by way of example only, by means of conventional mixing, dissolving, granulating, dragee-making, levigating, emulsifying, encapsulating, entrapping or compression processes.

In some embodiments, the pharmaceutical compositions will include at least one compound of Formula (I), (Ia), (Ib), (II), (IIa), (III), (IIIa), (IV), or (IVa) as an active ingredient in free-acid or free-base form, or in a pharmaceutically acceptable salt form. In addition, the methods and pharmaceutical compositions described herein include the use of N-oxides (if appropriate), crystalline forms, amorphous phases, as well as active metabolites of these compounds having the same type of activity.

In some embodiments, compounds of Formula (I), (Ia), (Ib), (II), (IIa), (III), (IIIa), (IV), or (IVa) exist in unsolvated form or in solvated forms with pharmaceutically acceptable solvents such as water, ethanol, and the like. The solvated forms of the compounds of Formula (I), (Ia), (Ib), (II), (IIa), (III), (IIIa), (IV), or (IVa) are also considered to be disclosed herein. In some embodiments, the compounds of Formula (I), (Ia), (Ib), (II), (IIa), (III), (IIIa), (IV), or (IVa) exist as tautomers. All tautomers are included within the scope of the compounds presented herein.

In certain embodiments, compositions provided herein include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In some embodiments, formulations described herein benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

The pharmaceutical compositions described herein, which include a compound of Formula (I), (Ia), (Ib), (II), (IIa), (III), (IIIa), (IV), or (IVa) are formulated into any suitable dosage form, including but not limited to, aqueous oral dispersions, liquids, gels, syrups, elixirs, slurries, suspensions, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations.

Certain Systemically Administered Compositions

In one aspect, a compound of Formula (I), (Ia), (Ib), (II), (IIa), (III), (IIIa), (IV), or (IVa) is formulated into a pharmaceutical composition suitable for intramuscular, subcutaneous, or intravenous injection. In one aspect, formulations suitable for intramuscular, subcutaneous, or intravenous injection include physiologically acceptable sterile aqueous or non-aqueous solutions, dispersions, suspensions or emulsions, and sterile powders for reconstitution into sterile injectable solutions or dispersions. Examples of suitable aqueous and non-aqueous carriers, diluents, solvents, or vehicles include water, ethanol, polyols (propyleneglycol, polyethylene-glycol, glycerol, cremophor and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. In some embodiments, formulations suitable for subcutaneous injection also contain additives such as preserving, wetting, emulsifying, and dispensing agents. Prevention of the growth of microorganisms can be ensured by various antibacterial and antifungal agents, such as parabens, chlorobutanol, phenol, sorbic acid, and the like. In some cases it is desirable to include isotonic agents, such as sugars, sodium chloride, and the like. Prolonged absorption of the injectable pharmaceutical form can be brought about by the use of agents delaying absorption, such as aluminum monostearate and gelatin.

For intravenous injections or drips or infusions, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspensions, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

For administration by inhalation, a compound of Formula (I), (Ia), (Ib), (II), (IIa), (III), (IIIa), (IV), or (IVa) is formulated for use as an aerosol, a mist or a powder. Pharmaceutical compositions described herein are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Representative intranasal formulations are described in, for example, U.S. Pat. Nos. 4,476,116, 5,116,817 and 6,391,452. Formulations that include a compound of Formula (I) are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions.

Pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as, for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. If desired, disintegrating agents are added, such as the cross-linked croscarmellose sodium, polyvinylpyrrolidone, agar, or alginic acid or a salt thereof such as sodium alginate. In some embodiments, dyestuffs or pigments are added to the tablets or dragee coatings for identification or to characterize different combinations of active compound doses.

In some embodiments, pharmaceutical formulations of a compound of Formula (I), (Ia), (Ib), (II), (IL), (III), (IIIa), (IV), or (IVa) are in the form of a capsules, including push-fit capsules made of gelatin, as well as soft, sealed capsules made of gelatin and a plasticizer, such as glycerol or sorbitol. The push-fit capsules contain the active ingredients in admixture with filler such as lactose, binders such as starches, and/or lubricants such as talc or magnesium stearate and, optionally, stabilizers. In soft capsules, the active compounds are dissolved or suspended in suitable liquids, such as fatty oils, liquid paraffin, or liquid polyethylene glycols. In some embodiments, stabilizers are added. A capsule may be prepared, for example, by placing the bulk blend of the formulation of the compound described above, inside of a capsule. In some embodiments, the formulations (non-aqueous suspensions and solutions) are placed in a soft gelatin capsule. In other embodiments, the formulations are placed in standard gelatin capsules or non-gelatin capsules such as capsules comprising HPMC. In other embodiments, the formulation is placed in a sprinkle capsule, wherein the capsule is swallowed whole or the capsule is opened and the contents sprinkled on food prior to eating.

All formulations for oral administration are in dosages suitable for such administration.

In one aspect, solid oral dosage forms are prepared by mixing a compound of Formula (I), (Ia), (Ib), (II), (IL), (III), (IIIa), (IV), or (IVa) with one or more of the following: antioxidants, flavoring agents, and carrier materials such as binders, suspending agents, disintegration agents, filling agents, surfactants, solubilizers, stabilizers, lubricants, wetting agents, and diluents.

In some embodiments, the solid dosage forms disclosed herein are in the form of a tablet, (including a suspension tablet, a fast-melt tablet, a bite-disintegration tablet, a rapid-disintegration tablet, an effervescent tablet, or a caplet), a pill, a powder, a capsule, solid dispersion, solid solution, bioerodible dosage form, controlled release formulations, pulsatile release dosage forms, multiparticulate dosage forms, beads, pellets, granules. In other embodiments, the pharmaceutical formulation is in the form of a powder.

Compressed tablets are solid dosage forms prepared by compacting the bulk blend of the formulations described above. In various embodiments, tablets will include one or more flavoring agents.

In other embodiments, the tablets will include a film surrounding the final compressed tablet. In some embodiments, the film coating can provide a delayed release of the compound of Formula (I), (Ia), (Ib), (II), (IL), (III), (IIIa), (IV), or (IVa) from the formulation. In other embodiments, the film coating aids in patient compliance (e.g., Opadry® coatings or sugar coating). Film coatings including Opadry® typically range from about 1% to about 3% of the tablet weight.

In some embodiments, solid dosage forms, e.g., tablets, effervescent tablets, and capsules, are prepared by mixing particles of a compound with one or more pharmaceutical excipients to form a bulk blend composition. The bulk blend is readily subdivided into equally effective unit dosage forms, such as tablets, pills, and capsules. In some embodiments, the individual unit dosages include film coatings. These formulations are manufactured by conventional formulation techniques.

In another aspect, dosage forms include microencapsulated formulations. In some embodiments, one or more other compatible materials are present in the microencapsulation material. Exemplary materials include, but are not limited to, pH modifiers, erosion facilitators, anti-foaming agents, antioxidants, flavoring agents, and carrier materials such as binders, suspending agents, disintegration agents, filling agents, surfactants, solubilizers, stabilizers, lubricants, wetting agents, and diluents.

Exemplary useful microencapsulation materials include, but are not limited to, hydroxypropyl cellulose ethers (HPC) such as Klucel® or Nisso HPC, low-substituted hydroxypropyl cellulose ethers (L-HPC), hydroxypropyl methyl cellulose ethers (HPMC) such as Seppifilm-LC, Pharmacoat®, Metolose SR, Methocel®-E, Opadry YS, PrimaFlo, Benecel MP824, and Benecel MP843, methylcellulose polymers such as Methocel®-A, hydroxypropylmethylcellulose acetate stearate Aqoat (HF-LS, HF-LG, HF-MS) and Metolose®, Ethylcelluloses (EC) and mixtures thereof such as E461, Ethocel®, Aqualon®-EC, Surelease®, Polyvinyl alcohol (PVA) such as Opadry AMB, hydroxyethylcelluloses such as Natrosol®, carboxymethylcelluloses and salts of carboxymethylcelluloses (CMC) such as Aqualon®-CMC, polyvinyl alcohol and polyethylene glycol co-polymers such as Kollicoat IR®, monoglycerides (Myverol), triglycerides (KLX), polyethylene glycols, modified food starch, acrylic polymers and mixtures of acrylic polymers with cellulose ethers such as Eudragit® EPO, Eudragit® L30D-55, Eudragit® FS 30D Eudragit® L100-55, Eudragit® L100, Eudragit® S100, Eudragit® RD100, Eudragit® E100, Eudragit® L12.5, Eudragit® 512.5, Eudragit® NE30D, and Eudragit® NE 40D, cellulose acetate phthalate, sepifilms such as mixtures of HPMC and stearic acid, cyclodextrins, and mixtures of these materials.

Liquid formulation dosage forms for oral administration are optionally aqueous suspensions selected from the group including, but not limited to, pharmaceutically acceptable aqueous oral dispersions, emulsions, solutions, elixirs, gels, and syrups. See, e.g., Singh et al., Encyclopedia of Pharmaceutical Technology, 2nd Ed., pp. 754-757 (2002). In addition to a Hedgehog signaling inhibitor, the liquid dosage forms optionally include additives, such as: (a) disintegrating agents; (b) dispersing agents; (c) wetting agents; (d) at least one preservative, (e) viscosity enhancing agents, (f) at least one sweetening agent, and (g) at least one flavoring agent. In some embodiments, the aqueous dispersions further includes a crystal-forming inhibitor.

In some embodiments, the pharmaceutical formulations described herein are self-emulsifying drug delivery systems (SEDDS). Emulsions are dispersions of one immiscible phase in another, usually in the form of droplets. Generally, emulsions are created by vigorous mechanical dispersion. SEDDS, as opposed to emulsions or microemulsions, spontaneously form emulsions when added to an excess of water without any external mechanical dispersion or agitation. An advantage of SEDDS is that only gentle mixing is required to distribute the droplets throughout the solution. Additionally, water or the aqueous phase is optionally added just prior to administration, which ensures stability of an unstable or hydrophobic active ingredient. Thus, the SEDDS provides an effective delivery system for oral and parenteral delivery of hydrophobic active ingredients. In some embodiments, SEDDS provides improvements in the bioavailability of hydrophobic active ingredients. Methods of producing self-emulsifying dosage forms include, but are not limited to, for example, U.S. Pat. Nos. 5,858,401, 6,667,048, and 6,960,563.

Buccal formulations that include a compound of Formula (I), (Ia), (Ib), (II), (IL), (III), (IIIa), (IV), or (IVa) are administered using a variety of formulations known in the art. For example, such formulations include, but are not limited to, U.S. Pat. Nos. 4,229,447, 4,596,795, 4,755,386, and 5,739,136. In addition, the buccal dosage forms described herein can further include a bioerodible (hydrolysable) polymeric carrier that also serves to adhere the dosage form to the buccal mucosa. For buccal or sublingual administration, the compositions may take the form of tablets, lozenges, or gels formulated in a conventional manner.

For intravenous injections, a Hedgehog signaling inhibitor is optionally formulated in aqueous solutions, preferably in physiologically compatible buffers such as Hank's solution, Ringer's solution, or physiological saline buffer. For transmucosal administration, penetrants appropriate to the barrier to be permeated are used in the formulation. For other parenteral injections, appropriate formulations include aqueous or nonaqueous solutions, preferably with physiologically compatible buffers or excipients.

Parenteral injections optionally involve bolus injection or continuous infusion. Formulations for injection are optionally presented in unit dosage form, e.g., in ampoules or in multi dose containers, with an added preservative. In some embodiments, a pharmaceutical composition described herein is in a form suitable for parenteral injection as a sterile suspensions, solutions or emulsions in oily or aqueous vehicles, and contain formulatory agents such as suspending, stabilizing and/or dispersing agents. Pharmaceutical formulations for parenteral administration include aqueous solutions of an agent that modulates the activity of a carotid body in water soluble form. Additionally, suspensions of an agent that modulates the activity of a carotid body are optionally prepared as appropriate, e.g., oily injection suspensions.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropylmethylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethycellulose (HPMC), hydroxypropylmethylcellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powder-filled gelatin capsule formulations. Binder usage level in tablet formulations varies whether direct compression, wet granulation, roller compaction, or usage of other excipients such as fillers which itself can act as moderate binder. Binder levels of up to 70% in tablet formulations is common.

Suitable lubricants or glidants for use in the solid dosage forms described herein include, but are not limited to, stearic acid, calcium hydroxide, talc, corn starch, sodium stearyl fumerate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxy-propylmethylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Suitable antioxidants for use in the solid dosage forms described herein include, for example, e.g., butylated hydroxytoluene (BHT), sodium ascorbate, and tocopherol.

It should be appreciated that there is considerable overlap between additives used in the solid dosage forms described herein. Thus, the above-listed additives should be taken as merely exemplary, and not limiting, of the types of additives that can be included in solid dosage forms of the pharmaceutical compositions described herein. The amounts of such additives can be readily determined by one skilled in the art, according to the particular properties desired.

In various embodiments, the particles of a compound of Formula (I), (Ia), (Ib), (II), (IIa), (III), (IIIa), (IV), or (IVa) and one or more excipients are dry blended and compressed into a mass, such as a tablet, having a hardness sufficient to provide a pharmaceutical composition that substantially disintegrates within less than about 30 minutes, less than about 35 minutes, less than about 40 minutes, less than about 45 minutes, less than about 50 minutes, less than about 55 minutes, or less than about 60 minutes, after oral administration, thereby releasing the formulation into the gastrointestinal fluid.

In other embodiments, a powder including a compound of Formula (I), (Ia), (Ib), (II), (IIa), (III), (IIIa), (IV), or (IVa) is formulated to include one or more pharmaceutical excipients and flavors. Such a powder is prepared, for example, by mixing the compound and optional pharmaceutical excipients to form a bulk blend composition. Additional embodiments also include a suspending agent and/or a wetting agent. This bulk blend is uniformly subdivided into unit dosage packaging or multi-dosage packaging units.

In still other embodiments, effervescent powders are also prepared. Effervescent salts have been used to disperse medicines in water for oral administration.

Controlled Release Formulations

In some embodiments, the pharmaceutical dosage forms are formulated to provide a controlled release of a compound of Formula (I), (Ia), (Ib), (II), (IL), (III), (IIIa), (IV), or (IVa). Controlled release refers to the release of the compound from a dosage form in which it is incorporated according to a desired profile over an extended period of time. Controlled release profiles include, for example, sustained release, prolonged release, pulsatile release, and delayed release profiles. In contrast to immediate release compositions, controlled release compositions allow delivery of an agent to a subject over an extended period of time according to a predetermined profile. Such release rates can provide therapeutically effective levels of agent for an extended period of time and thereby provide a longer period of pharmacologic response while minimizing side effects as compared to conventional rapid release dosage forms. Such longer periods of response provide for many inherent benefits that are not achieved with the corresponding short acting, immediate release preparations.

In some embodiments, the solid dosage forms described herein are formulated as enteric coated delayed release oral dosage forms, i.e., as an oral dosage form of a pharmaceutical composition as described herein which utilizes an enteric coating to affect release in the small intestine or large intestine. In one aspect, the enteric coated dosage form is a compressed or molded or extruded tablet/mold (coated or uncoated) containing granules, powder, pellets, beads or particles of the active ingredient and/or other composition components, which are themselves coated or uncoated. In one aspect, the enteric coated oral dosage form is in the form of a capsule containing pellets, beads or granules, which include a compound of Formula (I), (Ia), (Ib), (II), (IL), (III), (IIIa), (IV), or (IVa), that are coated or uncoated.

Any coatings should be applied to a sufficient thickness such that the entire coating does not dissolve in the gastrointestinal fluids at pH below about 5, but does dissolve at pH about 5 and above. Coatings are typically selected from any of the following:

Shellac—this coating dissolves in media of pH>7; Acrylic polymers—examples of suitable acrylic polymers include methacrylic acid copolymers and ammonium methacrylate copolymers. The Eudragit series E, L, S, RL, RS and NE (Rohm Pharma) are available as solubilized in organic solvent, aqueous dispersion, or dry powders. The Eudragit series RL, NE, and RS are insoluble in the gastrointestinal tract but are permeable and are used primarily for colonic targeting. The Eudragit series E dissolve in the stomach. The Eudragit series L, L-30D and S are insoluble in stomach and dissolve in the intestine; Poly Vinyl Acetate Phthalate (PVAP)—PVAP dissolves in pH>5, and it is much less permeable to water vapor and gastric fluids.

Conventional coating techniques such as spray or pan coating are employed to apply coatings. The coating thickness must be sufficient to ensure that the oral dosage form remains intact until the desired site of topical delivery in the intestinal tract is reached.

In other embodiments, the formulations described herein are delivered using a pulsatile dosage form. A pulsatile dosage form is capable of providing one or more immediate release pulses at predetermined time points after a controlled lag time or at specific sites. Exemplary pulsatile dosage forms and methods of their manufacture are disclosed in U.S. Pat. Nos. 5,011,692, 5,017,381, 5,229,135, 5,840,329 and 5,837,284. In one embodiment, the pulsatile dosage form includes at least two groups of particles, (i.e. multiparticulate) each containing the formulation described herein. The first group of particles provides a substantially immediate dose of the compound of Formula (I) upon ingestion by a mammal. The first group of particles can be either uncoated or include a coating and/or sealant. In one aspect, the second group of particles comprises coated particles. The coating on the second group of particles provides a delay of from about 2 hours to about 7 hours following ingestion before release of the second dose. Suitable coatings for pharmaceutical compositions are described herein or known in the art.

In some embodiments, pharmaceutical formulations are provided that include particles of a compound of Formula (I), (Ia), (Ib), (II), (IL), (III), (IIIa), (IV), or (IVa) and at least one dispersing agent or suspending agent for oral administration to a subject. The formulations may be a powder and/or granules for suspension, and upon admixture with water, a substantially uniform suspension is obtained.

In some embodiments, the liquid formulations also include inert diluents commonly used in the art, such as water or other solvents, solubilizing agents, and emulsifiers. Exemplary emulsifiers are ethyl alcohol, isopropyl alcohol, ethyl carbonate, ethyl acetate, benzyl alcohol, benzyl benzoate, propyleneglycol, 1,3-butyleneglycol, dimethylformamide, sodium lauryl sulfate, sodium doccusate, cholesterol, cholesterol esters, taurocholic acid, phosphotidylcholine, oils, such as cottonseed oil, groundnut oil, corn germ oil, olive oil, castor oil, and sesame oil, glycerol, tetrahydrofurfuryl alcohol, polyethylene glycols, fatty acid esters of sorbitan, or mixtures of these substances, and the like.

Furthermore, pharmaceutical compositions optionally include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

Additionally, pharmaceutical compositions optionally include one or more salts in an amount required to bring osmolality of the composition into an acceptable range.

Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

Other pharmaceutical compositions optionally include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

In one embodiment, the aqueous suspensions and dispersions described herein remain in a homogenous state, as defined in The USP Pharmacists' Pharmacopeia (2005 edition, chapter 905), for at least 4 hours. In one embodiment, an aqueous suspension is re-suspended into a homogenous suspension by physical agitation lasting less than 1 minute. In still another embodiment, no agitation is necessary to maintain a homogeneous aqueous dispersion.

Examples of disintegrating agents for use in the aqueous suspensions and dispersions include, but are not limited to, a starch, e.g., a natural starch such as corn starch or potato starch, a pregelatinized starch, or sodium starch glycolate; a cellulose such as methylcrystalline cellulose, methylcellulose, croscarmellose, or a cross-linked cellulose, such as cross-linked sodium carboxymethylcellulose, cross-linked carboxymethylcellulose, or cross-linked croscarmellose; a cross-linked starch such as sodium starch glycolate; a cross-linked polymer such as crospovidone; a cross-linked polyvinylpyrrolidone; alginate such as alginic acid or a salt of alginic acid such as sodium alginate; a gum such as agar, guar, locust bean, Karaya, pectin, or tragacanth; sodium starch glycolate; bentonite; a natural sponge; a surfactant; a resin such as a cation-exchange resin; citrus pulp; sodium lauryl sulfate; sodium lauryl sulfate in combination starch; and the like.

In some embodiments, the dispersing agents suitable for the aqueous suspensions and dispersions described herein include, for example, hydrophilic polymers, electrolytes, Tween® 60 or 80, PEG, polyvinylpyrrolidone, and the carbohydrate-based dispersing agents such as, for example, hydroxypropylcellulose and hydroxypropyl cellulose ethers, hydroxypropyl methylcellulose and hydroxypropyl methylcellulose ethers, carboxymethylcellulose sodium, methylcellulose, hydroxyethylcellulose, hydroxypropylmethyl-cellulose phthalate, hydroxypropylmethyl-cellulose acetate stearate, noncrystalline cellulose, magnesium aluminum silicate, triethanolamine, polyvinyl alcohol (PVA), polyvinylpyrrolidone/vinyl acetate copolymer, 4-(1,1,3,3-tetramethylbutyl)-phenol polymer with ethylene oxide and formaldehyde (also known as tyloxapol), poloxamers; and poloxamines. In other embodiments, the dispersing agent is selected from a group not comprising one of the following agents: hydrophilic polymers; electrolytes; Tween® 60 or 80; PEG; polyvinylpyrrolidone (PVP); hydroxypropylcellulose and hydroxypropyl cellulose ethers; hydroxypropyl methylcellulose and hydroxypropyl methylcellulose ethers; carboxymethylcellulose sodium; methylcellulose; hydroxyethylcellulose; hydroxypropylmethyl-cellulose phthalate; hydroxypropylmethyl-cellulose acetate stearate; non-crystalline cellulose; magnesium aluminum silicate; triethanolamine; polyvinyl alcohol (PVA); 4-(1,1,3,3-tetramethylbutyl)-phenol polymer with ethylene oxide and formaldehyde; poloxamers; or poloxamines.

Wetting agents suitable for the aqueous suspensions and dispersions described herein include, but are not limited to, cetyl alcohol, glycerol monostearate, polyoxyethylene sorbitan fatty acid esters (e.g., the commercially available Tweens® such as e.g., Tween 20® and Tween 80®, and polyethylene glycols, oleic acid, glyceryl monostearate, sorbitan monooleate, sorbitan monolaurate, triethanolamine oleate, polyoxyethylene sorbitan monooleate, polyoxyethylene sorbitan monolaurate, sodium oleate, sodium lauryl sulfate, sodium docusate, triacetin, vitamin E TPGS, sodium taurocholate, simethicone, phosphotidylcholine and the like Suitable preservatives for the aqueous suspensions or dispersions described herein include, for example, potassium sorbate, parabens (e.g., methylparaben and propylparaben), benzoic acid and its salts, other esters of parahydroxybenzoic acid such as butylparaben, alcohols such as ethyl alcohol or benzyl alcohol, phenolic compounds such as phenol, or quaternary compounds such as benzalkonium chloride. Preservatives, as used herein, are incorporated into the dosage form at a concentration sufficient to inhibit microbial growth.

Suitable viscosity enhancing agents for the aqueous suspensions or dispersions described herein include, but are not limited to, methyl cellulose, xanthan gum, carboxymethyl cellulose, hydroxypropyl cellulose, hydroxypropylmethyl cellulose, Plasdon® S-630, carbomer, polyvinyl alcohol, alginates, acacia, chitosans and combinations thereof. The concentration of the viscosity enhancing agent will depend upon the agent selected and the viscosity desired.

Examples of sweetening agents suitable for the aqueous suspensions or dispersions described herein include, for example, acacia syrup, acesulfame K, alitame, aspartame, chocolate, cinnamon, citrus, cocoa, cyclamate, dextrose, fructose, ginger, glycyrrhetinate, *glycyrrhiza* (licorice) syrup, monoammonium glyrrhizinate (MagnaSweet®), maltol, mannitol, menthol, neohesperidine DC, neotame, Prosweet® Powder, saccharin, sorbitol, *stevia*, sucralose, sucrose, sodium saccharin, saccharin, aspartame, acesulfame potassium, mannitol, sucralose, tagatose, thaumatin, vanilla, xylitol, or any combination thereof.

Methods of Dosing and Treatment Regimens

A method for treating any of the diseases or conditions described herein in a mammal in need of such treatment, involves administration of pharmaceutical compositions that include at least one compound of Formula (I), (Ia), (Ib), (II), (IIa), (III), (IIIa), (IV), or (IVa) or a pharmaceutically acceptable salt, or pharmaceutically acceptable solvate thereof, in therapeutically effective amounts to said mammal. In another embodiment, the compounds of Formula (I), (Ia), (Ib), (II), (IIa), (III), (IIIa), (IV), or (IVa) are used in the preparation of medicaments for the treatment of cancer. In some embodiments, the compounds of Formula (I), (Ia), (Ib), (II), (IIa), (III), (IIIa), (IV), or (IVa) are used in the preparation of medicaments for the treatment of cancer, wherein the cancer is selected from basal cell carcinoma, melanoma, leukemia, multiple myeloma, stomach cancer, pancreatic cancer, bladder cancer, prostate cancer, ovarian cancer, bone cancer, brain cancer, lung cancer, breast cancer, and skin cancer.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound of Formula (I), (Ia), (Ib), (II), (IIa), (III), (IIIa), (IV), or (IVa) in order to prevent a return of the symptoms of the disease or condition.

In certain embodiments wherein the patient's condition does not improve, upon the doctor's discretion the administration of the compound of Formula (I), (Ia), (Ib), (II), (IIa), (III), (IIIa), (IV), or (IVa) is administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered may be temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

In certain embodiments the dose of drug being administered may be temporarily reduced or temporarily suspended for a certain length of time (i.e., a "drug diversion"). In specific embodiments, the length of the drug diversion is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug diversion is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%. After a suitable length of time, the normal dosing schedule is optionally reinstated.

In some embodiments, once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but can nevertheless be determined according to the particular circumstances surrounding the case, including, e.g., the specific agent being administered, the route of administration, the condition being treated, and the subject or host being treated. In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously (or over a short period of time) or at appropriate intervals, for example as two, three, four or more sub-doses per day.

In some embodiments, as a patient is started on a regimen of a Hedgehog signaling inhibitor, the patient is also weaned off (e.g., step-wise decrease in dose) a second treatment regimen (e.g., a methylxanthine).

In one embodiment, the daily dosages appropriate for a compound of Formula (I), (Ia), (Ib), (II), (IIa), (III), (IIIa), (IV), or (IVa) described herein are from about 0.01 to about 10 mg/kg per body weight. In specific embodiments, an indicated daily dosage in a large mammal, including, but not limited to, humans, is in the range from about 0.5 mg to about 1000 mg, conveniently administered in divided doses, including, but not limited to, up to four times a day. In one embodiment, the daily dosage is administered in extended release form. In certain embodiments, suitable unit dosage forms for oral administration comprise from about 1 to 500 mg active ingredient. In other embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

Combination Therapy

In some embodiments, a compound of Formula (I), (Ia), (Ib), (II), (IIa), (III), (IIIa), (IV), or (IVa) is administered to an individual in need thereof in combination with an anti-tumor agent. In some embodiments, a compound of Formula (I), (Ia), (Ib), (II), (IIa), (III), (IIIa), (IV), or (IVa) is administered to an individual in need thereof in combination with an anti-tumor agent, wherein the anti-tumor agent is an oxysterol, a Hedgehog pathway antagonist, a chemotherapeutic agent, or a combination thereof. In some embodiments, a compound of Formula (I), (Ia), (Ib), (II), (IIa), (III), (IIIa), (IV), or (IVa) is administered to an individual in need thereof in combination with an anti-tumor agent, wherein the anti-tumor agent is an oxysterol. In some embodiments, a compound of Formula (I), (Ia), (Ib), (II), (IIa), (III), (IIIa), (IV), or (IVa) is administered to an individual in need thereof in combination with an anti-tumor agent, wherein the anti-tumor agent is a Hedgehog pathway antagonist. In some embodiments, a compound of Formula (I), (Ia), (Ib), (II), (IIa), (III), (IIIa), (IV), or (IVa) is administered to an individual in need thereof in combination with an anti-tumor agent, wherein the anti-tumor agent is a chemotherapeutic agent. In some embodiments, a compound of Formula (I), (Ia), (Ib), (II), (IIa), (III), (IIIa), (IV), or (IVa) is administered to an individual in need thereof in combination with an anti-tumor agent, wherein the anti-tumor agent is a combination of an oxysterol, a Hedgehog pathway antagonist, or a chemotherapeutic agent.

Combination Formulations and Kits

Also provided herein are kits for therapies described herein. In some embodiments, the kit comprises a Hedgehog signaling inhibitor and a second treatment regimen. Such kits generally will comprise one or more of the active agent as disclosed herein, and instructions for using the kit.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

In certain embodiments, the pharmaceutical compositions are presented in a pack or dispenser device which contains one or more unit dosage forms containing a Hedgehog signaling inhibitor. In another embodiment, the pack for example contains metal or plastic foil, such as a blister pack.

EXAMPLES

The following specific examples are to be construed as merely illustrative, and not limitative of the remainder of the disclosure in any way whatsoever.

All synthetic chemistry was performed in standard laboratory glassware unless indicated otherwise in the examples. Commercial reagents were used as received.

Example 1

Synthesis of (E)-3-(4-fluorophenyl)-1-((3S,8S,9S, 10R,13S,14S,17S)-3-hydroxy-10,13-dimethyl-2,3,4, 7,8,9,10,11,12,13,14,15,16,17-tetradecahydro-1H-cyclopenta[a]phenanthren-17-yl)prop-2-en-1-one (1)

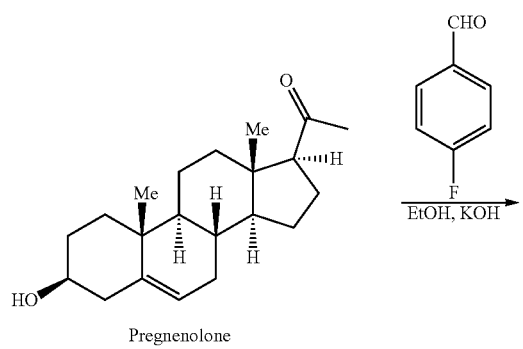

Pregnenolone

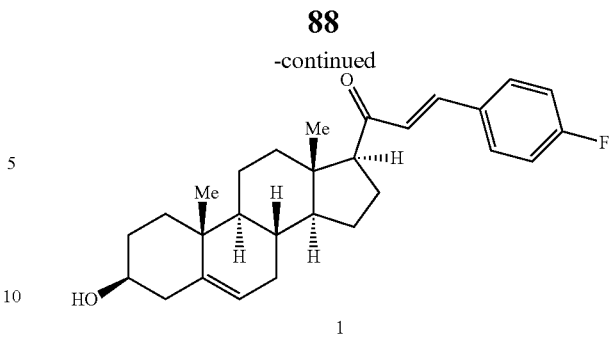

To a solution of pregnenolone (0.945 g, 3 mmol) and 4-fluorobenzaldehyde (0.446 g, 1.2 eq) in ethanol (30 mL) was added 2 mL of 4M KOH solution. After stirring for 24 at r.t., the resulting suspension was diluted with water (30 mL) and the solid product isolated by filtration, washed with water and dried by aspiration to give the title compound 1 (1.18 g, 93%).

Example 2

Synthesis of 3-(4-fluorophenyl)-1-((3S,8S,9S,10R, 13S,14S,17S)-3-hydroxy-10,13-dimethyl-2,3,4,7,8,9, 10,11,12,13,14,15,16,17-tetradecahydro-1H-cyclopenta[a]phenanthren-17-yl)propan-1-one (2)

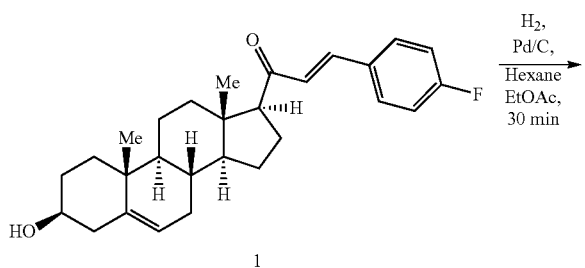

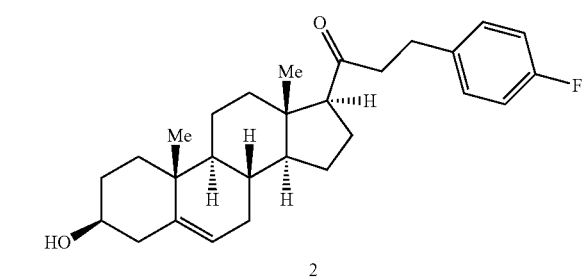

To a suspension of 1 (0.25 g, 0.6 mmol) in hexane (2 mL) was added just enough EtOAc to dissolve the sample (5 mL). To the resulting solution, Pd/C catalyst (10% on carbon, 25 mg) was added and the mixture degassed via house vacuum. The mixture was then exposed to hydrogen gas (1 atm, balloon) for 30 min, after which TLC analysis revealed disappearance of starting material. The catalyst was removed by filtration over celite. After evaporation of the solvent, the title compound 2 was obtained and used without further purification. $^1$H NMR (CDCl$_3$, 400 MHZ) δ 7.17-7.10 (2H, m), 6.95 (2H, dd, J=8.8, 8.8 Hz), 5.35-5.34 (1H, m), 3.48 (1H, dddd, J=10.9, 10.9, 5.5, 5.5 Hz), 2.83-2.80 (2H, m), 2.73-2.80 (2H, m), 2.53 (1H, dd, J=8.8, 8.8 Hz), 2.27-1.17 (15H, m), 1.06 (3H, s), 0.61 (3H, s). $^{13}$C NMR (CDCl$_3$, 100 MHZ) δ 210.4, 161.2 (d, J=242 Hz), 140.8, 138.2 (d, J=3.1), 129.6 (d, J=20 Hz), 121.6, 115.1 (d, J=20 Hz), 71.7, 63.1, 57.0, 50.0, 46.0, 44.3, 42.25, 39.0, 37.3, 36.5, 31.9, 31.6, 28.9, 24.5, 23.0, 21.1, 19.4, 13.4.

Example 3

Synthesis of 3-(4-fluorophenyl)-1-((3S,5S,8R,9S,10S,13S,14S,17S)-3-hydroxy-10,13-dimethylhexadecahydro-1H-cyclopenta[a]phenanthren-17-yl)propan-1-one (3)

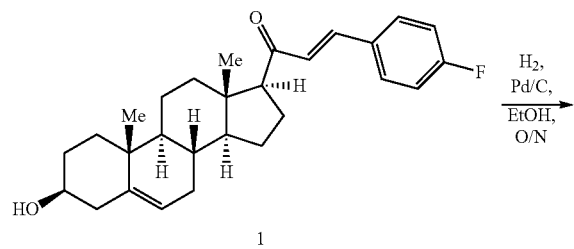

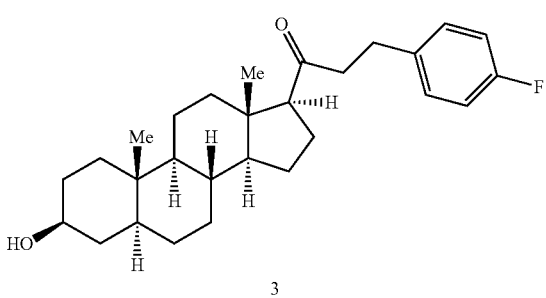

To a suspension of 1 (0.42 g, 1 mmol) in ethanol (10 mL) was added Pd/C catalyst (10% on carbon, 40 mg) and the mixture degassed via house vacuum. The mixture was then exposed to hydrogen gas (1 atm, balloon) for 72 h. The catalyst was removed by filtration over celite. The solvent was removed in vacuo to afford the title compound 3. $^1$H NMR (CDCl$_3$, 400 MHZ) δ 7.17-7.10 (2H, m), 6.95 (2H, dd, J=8.8, 8.8 Hz), 3.52 (1H, dddd, J=10.9, 10.9, 5.5, 5.5 Hz), 2.83-2.80 (2H, m), 2.73-2.80 (2H, m), 2.53 (1H, dd, J=8.8, 8.8 Hz), 2.27-0.89 (15H, m), 0.75 (3H, s), 0.61 (3H, s). $^{13}$C NMR (CDCl$_3$, 100 MHZ) δ 201.4, 161.2 (d, J=242 Hz), 137.1 (d, J=3.1), 129.6 (d, J=20 Hz), 115.1 (d, J=20 Hz), 71.3, 63.2, 56.8, 54.2, 46.0, 44.8, 44.6, 39.2, 38.15, 37.0, 35.5, 35.5, 32.0, 31.5, 28.9, 28.6, 24.4, 22.9, 21.2, 13.6, 12.3.

Example 4

Synthesis of (3S,8S,9S,10R,13S,14S,17S)-17-((R)-4-(4-fluorophenyl)-2-hydroxybutan-2-yl)-10,13-dimethyl-2,3,4,7,8,9,10,11,12,13,14,15,16,17-tetradecahydro-1H-cyclopenta[a]phenanthren-3-ol (4)

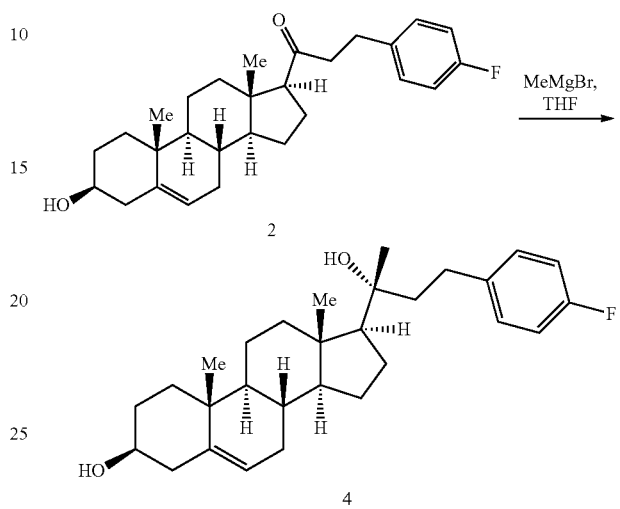

To a solution of 2 (77 mg, 0.18 mmol) in THF (1 mL) was added a commercial stock solution of methyl Grignard reagent (4 eq) in ether. After stirring the mixture at r.t. for 5 h, water (10 mL) was carefully added followed by EtOAc (10 mL). After separation of the layers, the aqueous layer was back extracted with EtOAc (2×10 mL) and the combined organic layers washed with brine dried over Na$_2$SO$_4$ and the solvent evaporated. The crude product was purified on an ISCO combiflash Rf system (4 g column, non polar gradient), to afford the title compound 4 (40 mg). $^1$H NMR (CDCl$_3$, 400 MHZ) δ 7.14-7.11 (2H, m), 6.97 (2H, dd, J=8.8, 8.8 Hz), 5.33 (1H, m), 3.54 (1H, dddd, J=10.9, 10.9, 5.5, 5.5 Hz), 2.73-2.64 (2H, m), 2.32-1.22 (15H, m), 1.21 (3H, s), 0.99 (3H, s), 0.86 (3H, s). $^{13}$C NMR (CDCl$_3$, 100 MHZ) δ 161.2 (d, J=242 Hz), 140.8, 138.2 (d, J=3.1), 129.6 (d, J=20 Hz), 121.6, 115.1 (d, J=20 Hz), 75.7, 71.7, 58.7, 56.9, 50.3, 44.7, 43.0, 42.3, 40.3, 37.3, 36.5, 31.8, 31.6, 31.4, 29.6, 26.8, 23.8, 23.3, 20.9, 19.4, 13.8.

Example 5

Synthesis of (3S,8S,9S,10R,13S,14S,17S)-17-((R)-3-(4-fluorophenyl)-1-hydroxy-1-phenylpropyl)-10,13-dimethyl-2,3,4,7,8,9,10,11,12,13,14,15,16,17-tetradecahydro-1H-cyclopenta[a]phenanthren-3-ol (5)

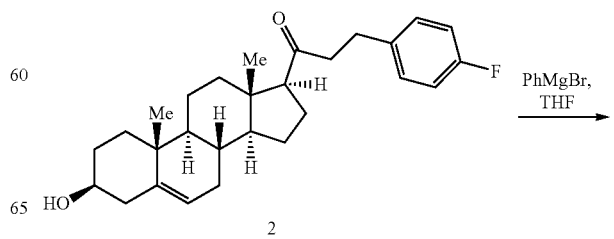

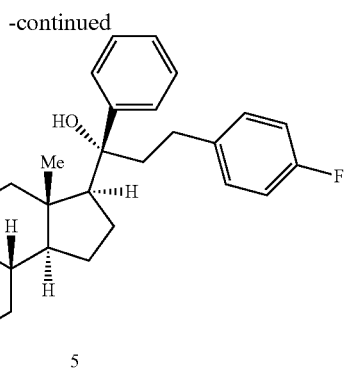

5

To a solution of 2 (77 mg, 0.18 mmol) in THF (1 mL) was added a commercial stock solution of phenyl Grignard reagent (4 eq) in ether. After stirring the mixture at r.t. for 5 h, water (10 mL) was carefully added followed by EtOAc (10 mL). After separation of the layers, the aqueous layer was back extracted with EtOAc (2×10 mL) and the combined organic layers washed with brine dried over $Na_2SO_4$ and the solvent evaporated. The crude product was purified on an ISCO combiflash Rf system (4 g column, non polar gradient), to afford the title compound 5 (40 mg). $^1$H NMR (CDCl$_3$, 400 MHZ) δ 7.40-7.21 (5H, m), 7.14-7.11 (2H, m), 6.97 (2H, dd, J=8.8, 8.8 Hz), 5.33 (1H, m), 3.54 (1H, dddd, J=10.9, 10.9, 5.5, 5.5 Hz), 2.73-2.64 (2H, m), 2.32-1.22 (15H, m), 0.99 (3H, s), 0.86 (3H, s). $^{13}$C NMR (CDCl$_3$, 100 MHZ) δ 161.2 (d, J=242 Hz), 146.6, 140.8, 138.2 (d, J=3.1), 129.6 (d, J=20 Hz), 128.0, 127.9, 126.1, 125.7, 125.1, 121.6, 115.1 (d, J=20 Hz), 79.5, 71.7, 61.0, 57.0, 50.0, 43.6, 43.1, 42.3, 40.5, 37.2, 36.5, 31.7, 31.3, 29.5, 23.4, 22.8, 20.9, 19.4, 13.6.

Example 6

Synthesis of (3S,5S,8R,9S,10S,13S,14S,17S)-17-((R)-4-(4-fluorophenyl)-2-hydroxybutan-2-yl)-10,13-dimethylhexadecahydro-1H-cyclopenta[a]phenanthren-3-ol (6)

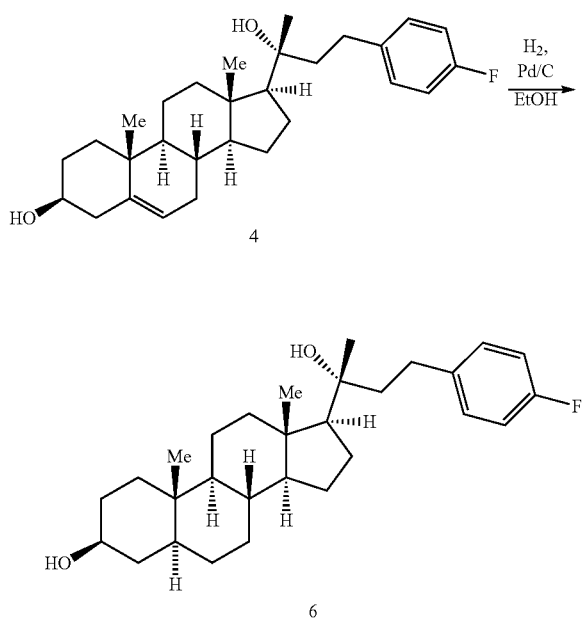

To a solution of 4 (32 mg, 0.075 mmol) in ethanol (3 mL) was added Pd/C catalyst (10% on carbon, 4 mg) and the mixture degassed via house vacuum. The mixture was then exposed to hydrogen gas (1 atm, balloon) for 72 h. The catalyst was removed by filtration over celite. The solvent was removed in vacuo to afford the title compound 6. $^1$H NMR (CDCl$_3$, 400 MHZ) δ 7.14-7.11 (2H, m), 6.97 (2H, dd, J=8.8, 8.8 Hz), 3.54 (1H, dddd, J=10.9, 10.9, 5.5, 5.5 Hz), 2.73-2.64 (2H, m), 2.32-1.22 (15H, m), 1.21 (3H, s), 0.80 (3H, s), 0.76 (3H, s). $^{13}$C NMR (CDCl$_3$, 100 MHZ) δ 161.2 (d, J=242 Hz), 138.2 (d, J=3.1), 129.6 (d, J=20 Hz), 115.1 (d, J=20 Hz), 75.7, 71.3, 58.8, 56.7, 54.3, 44.9, 44.7, 43.3, 40.6, 38.15, 37.0, 35.5, 34.9, 32.0, 31.5, 29.6, 28.7, 23.8, 26.8, 23.7, 23.3, 21.1, 14.0, 12.3.

Example 7

Synthesis of (R)-4-(4-fluorophenyl)-2-((3S,8S,9S,10R,13S,14S,17S)-3-methoxy-10,13-dimethyl-2,3,4,7,8,9,10,11,12,13,14,15,16,17-tetradecahydro-1H-cyclopenta[a]phenanthren-17-yl)butan-2-ol (8)

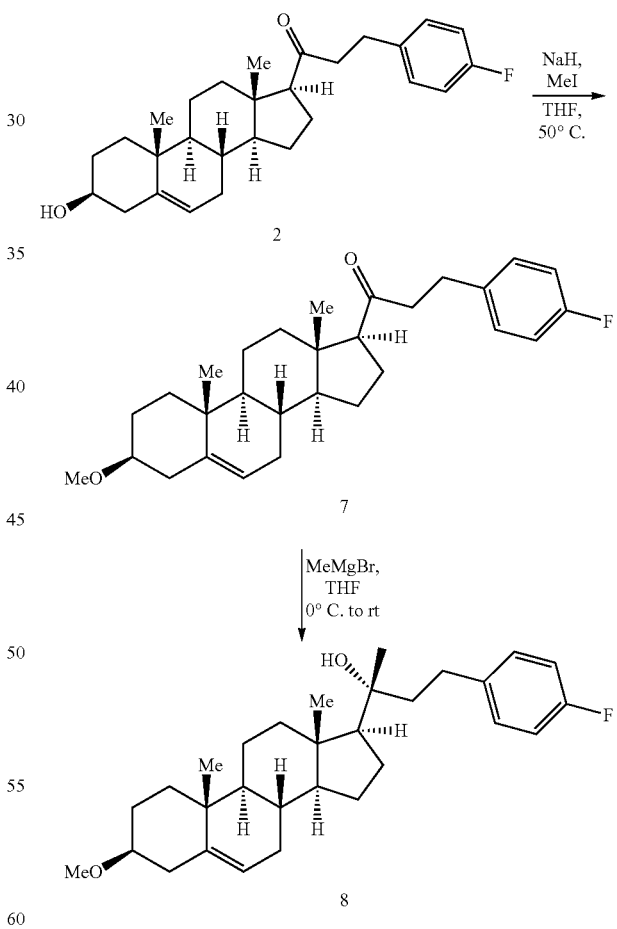

To a solution of 2 (247 mg, 0.58 mmol) in THF (2.5 mL) at 0° C., 60% sodium hydride dispersed in mineral oil (47 mg, 1.16 mmol) was added to the reaction mixture. The mixture was heated to 50° C. for 30 mins and iodomethane (55 μL, 0.87 mmol) was added. The mixture was allowed to stir at 50° C. for 4 h. After 4 h, additional iodomethane (55

μL, 0.87 mmol) was added and the reaction mixture was stirred overnight at 50° C. The mixture was cooled to 0° C. and then quenching with sat. ammonium chloride solution (4 mL). The mixture was extracted with DCM (10 mL×3) and the combined organic layers were dried over anhydrous sodium sulfate. The organic layers were concentrated in vacuo and purified by ISCO combiflash Rf system (12 g column, nonpolar gradient) to yield compound 7 (142 mg, 56%).

To a solution of 7 (142 mg, 0.32 mmol) in THF (2.6 mL) at 0° C., 3 M MeMgBr (640 μL, 1.92 mmol) was added dropwise to the reaction mixture. The mixture was warmed to room temperature and stirred overnight. The reaction mixture was cooled to 0° C. and quenched with sat. ammonium chloride solution (5 mL). The mixture was extracted with DCM (10 mL×3). The combined organic layers was dried with anhydrous sodium sulfate and concentrated in vacuo. The crude mixture was purified by ISCO combiflash Rf system (12 g gold column, nonpolar gradient) to yield the title compound 8 (48 mg, 33%). $^1$H NMR (500 MHz, CDCl$_3$) δ 7.15-7.13 (m, 2H), 6.98-6.94 (m, 2H), 5.36-5.35 (m, 1H), 3.35 (s, 3H), 3.08-3.02 (m, 1H), 2.70-2.66 (m, 2H), 2.38 (dq, J=13.2, 2.3 Hz, 1H), 2.18-2.07 (m, 2H), 2.01-1.96 (m, 1H), 1.93-1.89 (m, 1H), 1.87-1.83 (m, 3H), 1.78-1.71 (m, 2H), 1.68-1.62 (m, 1H), 1.52-1.49 (m, 3H), 1.48-1.45 (m, 2H), 1.43-1.40 (m, 1H), 1.31-1.24 (m, 2H), 1.22 (s, 3H), 1.18-1.11 (m, 1H), 1.06-1.00 (m, 2H), 0.99 (s, 3H), 0.95-0.89 (m, 1H), 0.87 (s, 3H). $^{13}$C NMR (125 MHz, CDCl$_3$) δ 162.4, 160.2, 140.9, 138.4, 138.3, 129.6, 121.4, 115.2, 115.0, 110.2, 80.3, 75.7, 58.6, 56.9, 55.6, 50.1, 44.7, 43.0, 40.3, 38.7, 37.2, 36.9, 31.8, 31.3, 29.6, 28.0, 26.8, 23.8, 23.2, 20.9, 19.4, 13.8.

Example 8

Synthesis of (3S,8S,9S,10R,13S,14S,17S)-10,13-dimethyl-17-((R)-1,1,1-trifluoro-4-(4-fluorophenyl)-2-hydroxybutan-2-yl)-2,3,4,7,8,9,10,11,12,13,14,15,16,17-tetradecahydro-1H-cyclopenta[a]phenanthren-3-ol (11)

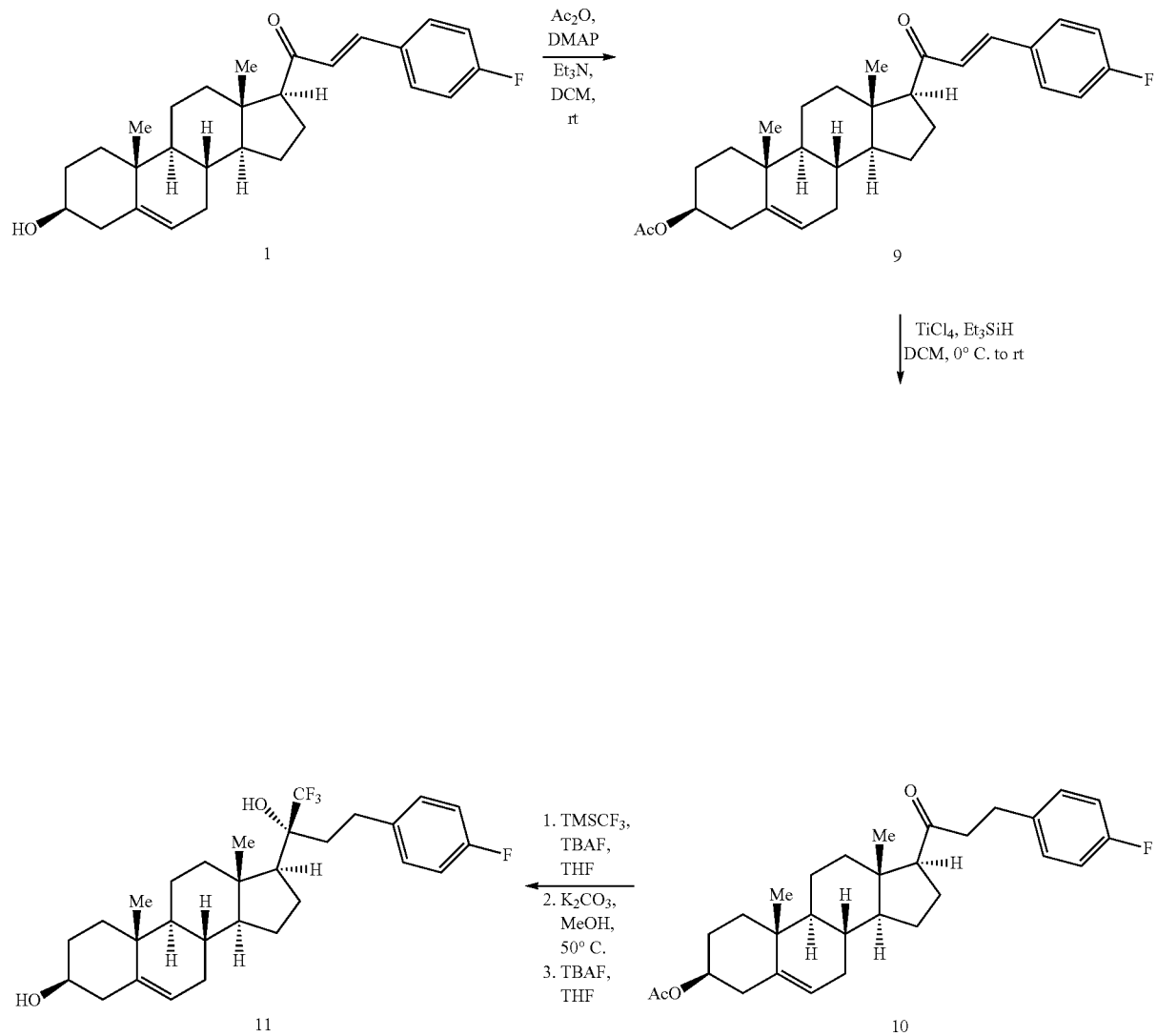

To a solution of 1 (250 mg, 0.6 mmol) in DCM (5 mL), was added sequentially acetic anhydride (119 μL, 1.26 mmol), DMAP (7 mg, 0.06 mmol), and Et₃N (84 μL, 0.6 mmol). The mixture was stirred at room temperature for 4 h. The mixture was washed with water (10 mL) and extracted with DCM (10 mL×3). The combined organic layers were dried, concentrated in vacuo, and purified by ISCO combiflash Rf system (12 g gold column, nonpolar gradient) to afford compound 9 (216 mg, 77%).

To a solution of 11 (216 mg, 0.46 mmol) in DCM (5 mL) at 0° C., 1M TiCl₄ in DCM (1.12 mL, 1.12 mmol) was added dropwise and stirred for 10 mins at 0° C. Et₃SiH (110 μL, 0.59 mmol) was then added in one portion at 0° C. and the mixture was warmed to room temperature by removing the cooling bath. After 45 mins, the reaction was quenched by pouring the mixture into aqueous sat. sodium bicarbonate solution (10 mL) and extracted with DCM (10 mL×3). The combined organic layers were dried with sodium sulfate, concentrated in vacuo, and purified by ISCO combiflash Rf system (12 g gold column, nonpolar gradient) to afford compound 10 (142 mg, 66%).

To a solution of 10 (116 mg, 0.25 mmol) in THF (1 mL) at 0° C., TMSCF₃ (170 μL, 1.14 mmol) and 1M TBAF in DCM (60 μL, 0.06 mmol) were added sequentially. The reaction mixture was warmed to room temperature slowly overnight. The mixture was cooled to 0° C. and quenched with 1M aqueous HCl (2 mL) and stirred for additional 1.5 h at 0° C. The aqueous mixture was extracted with EtOAc (10 mL×3). The combined organic layers were dried with sodium sulfate and concentrated in vacuo. The crude material was directly subjected to the next reaction without further purification.

To a solution of the crude product in MeOH (10 mL), an aqueous solution of K₂CO₃ (40 mg/200 μL) was added. The mixture was heated to 50° C. for 2 h and then concentrated in vacuo. The residue was diluted with water (10 mL) and extracted with DCM (10 mL×3). The combined organic layers were dried with sodium sulfate and concentrated in vacuo. The crude material was directly subjected to the next reaction without further purification.

To a solution of the crude product in THF (1 mL) at 0° C., 1M TBAF in DCM (500 μL) was added. The mixture was then stirred at room temperature for 1 h. The mixture was concentrated in vacuo and diluted with water (10 mL) and extracted with DCM (10 mL×3). The combined organic layers were dried with sodium sulfate, concentrated in vacuo, and purified by ISCO combiflash Rf system (12 g column, nonpolar gradient) to yield the title compound 11 (53 mg, 43%). ¹H NMR (500 MHz, CDCl₃) δ 7.15-7.12 (m, 2H), 7.00-6.96 (m, 2H), 5.36-5.35 (m, 1H), 3.56-3.49 (m, 1H), 2.75-2.66 (m, 2H), 2.32-2.28 (m, 1H), 2.25-2.09 (m, 4H), 2.02-1.93 (m, 3H), 1.87-1.79 (m, 4H), 1.75-1.66 (m, 1H), 1.51-1.46 (m, 4H), 1.44-1.40 (m, 1H), 1.23-1.17 (m, 1H), 1.12-1.04 (m, 2H), 1.01-0.93 (m, 5H), 0.87 (s, 3H). ¹³C NMR (125 MHz, CDCl₃) δ 160.7, 140.8, 137.1, 129.5 ($J_{C-F}$=7.8 Hz), 121.4, 115.4 ($J_{C-F}$=21.1 Hz), 71.7, 56.4, 50.3, 49.9, 43.6, 42.2, 39.9, 37.3, 37.2, 36.5, 31.64, 31.61, 31.4, 29.1, 23.8, 22.6, 21.0, 19.4, 13.3.

Example 9

Synthesis of (3S,8R,9S,10S,13S,14S,17S)-10,13-dimethyl-17-((R)-1,1,1-trifluoro-4-(4-fluorophenyl)-2-hydroxybutan-2-yl)hexadecahydro-1H-cyclopenta [a]phenanthren-3-ol (13)

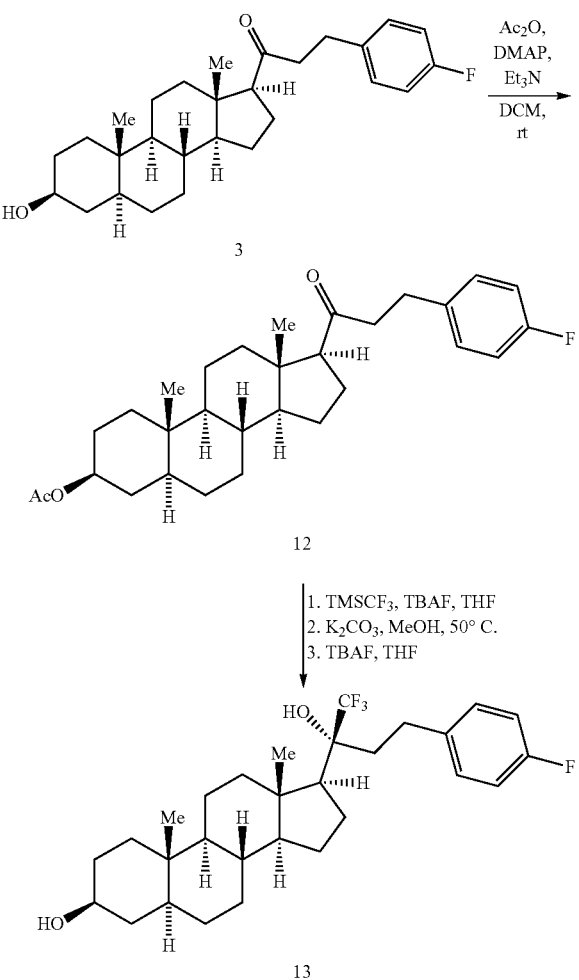

To a solution of 3 (200 mg, 0.5 mmol) in DCM (4 mL), was added sequentially acetic anhydride (93 μL, 0.98 mmol), DMAP (6 mg, 0.05 mmol), and Et₃N (66 μL, 0.5 mmol). The mixture was stirred at room temperature for 1 h. The mixture was washed with water (10 mL) and extracted with DCM (10 mL×3). The combined organic layers were dried, concentrated in vacuo, and purified by ISCO combiflash Rf system (12 g column, nonpolar gradient) to afford compound 12 (183 mg, 83%).

To a solution of 12 (183 mg, 0.39 mmol) in THF (1.6 mL) at 0° C., TMSCF₃ (289 μL, 1.95 mmol) and 1M TBAF in DCM (94 μL, 0.09 mmol) were added sequentially. The reaction mixture was warmed to room temperature slowly overnight. The mixture was cooled to 0° C. and quenched with 1M aqueous HCl (2 mL) and stirred for additional 1.5 h at 0° C. The aqueous mixture was extracted with EtOAc (10 mL×3). The combined organic layers were dried with sodium sulfate and concentrated in vacuo. The crude material was directly subjected to the next reaction without further purification.

To a solution of crude product in MeOH (15 mL), an aqueous solution of K₂CO₃ (66 mg/320 μL) was added. The mixture was heated to 50° C. for 2 h and then concentrated in vacuo. The residue was diluted with water (10 mL) and extracted with DCM (10 mL×3). The combined organic layers were dried with sodium sulfate and concentrated in vacuo. The crude material was directly subjected to the next reaction without further purification.

To a solution of crude product in THF (1.5 mL) at 0° C., 1M TBAF in DCM (800 μL) was added. The mixture was then stirred at room temperature for 1 h. Upon completion, the mixture was concentrated in vacuo and diluted with water (10 mL) and extracted with DCM (10 mL×3). The combined organic layers were dried with sodium sulfate, concentrated in vacuo, and purified by ISCO combiflash Rf system (12 g column, nonpolar gradient) to yield the title compound 13 (115 mg, 59%). ¹H NMR (500 MHz, CDCl₃) δ 7.14-7.11 (m, 2H), 7.00-6.96 (m, 2H), 3.59 (sept, J=5.3 Hz, 1H), 2.74-2.66 (m, 2H), 2.18-2.11 (m, 2H), 2.09-2.00 (m, 2H), 1.94 (t, 1H), 1.86-1.76 (m, 3H), 1.73-1.65 (m, 3H), 1.44-1.23 (m, 8H), 1.22-0.93 (m, 5H), 0.92-0.87 (m, 1H), 0.84 (s, 3H), 0.80 (s, 3H), 0.64 (td, J=5.6, 3.8 Hz, 1H). ¹³C NMR (125 MHz, CDCl₃) δ 162.4, 160.4, 137.0, 129.5 ($J_{C-F}$=7.8 Hz), 115.3 ($J_{C-F}$=21.2 Hz), 71.3, 56.2, 54.1, 50.4, 44.8, 43.9, 40.2, 38.1, 37.2, 37.0, 35.4, 34.9, 31.8, 31.5, 29.1, 28.6, 23.8, 22.6, 21.2, 13.4, 12.3.

Example 10

Synthesis of (3S,8S,9S,10R,13S,14S,17S)-17-((R)-1-(4-fluorophenyl)-3-hydroxypentan-3-yl)-10,13-dimethyl-2,3,4,7,8,9,10,11,12,13,14,15,16,17-tetradecahydro-1H-cyclopenta[a]phenanthren-3-ol (14)

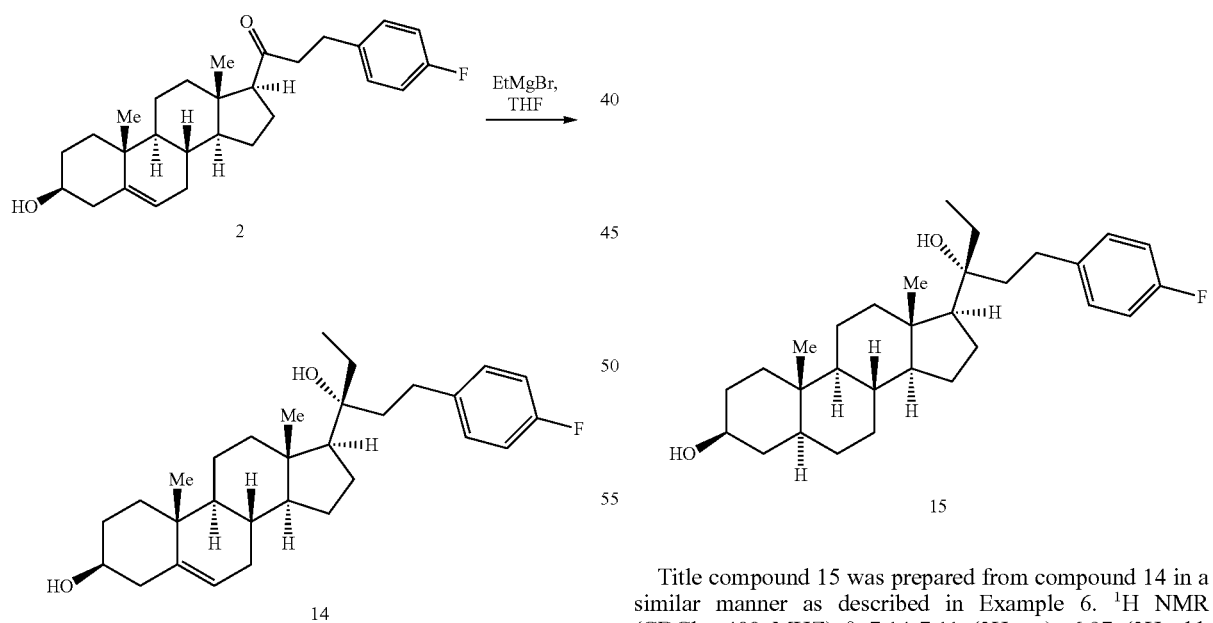

Title compound 14 was prepared in a similar manner as described in Example 4. ¹H NMR (500 MHz, CDCl₃) δ 7.14 (dd, J=8.5, 5.6 Hz, 2H), 6.96 (t, J=8.7 Hz, 2H), 5.35-5.34 (m, 1H), 3.54-3.49 (m, 1H), 2.66-2.54 (m, 2H), 2.31-2.20 (m, 2H), 2.07-2.04 (m, 1H), 2.00-1.95 (m, 1H), 1.92-1.75 (m, 6H), 1.69-1.62 (m, 4H), 1.49-1.42 (m, 6H), 1.30-1.22 (m, 2H), 1.05-1.02 (m, 2H), 0.99 (s, 3H), 0.96-0.91 (m, 2H), 0.89-0.86 (m, 6H). ¹³C NMR (125 MHz, CDCl₃) δ 140.8, 129.5 (d, $J_{C-F}$=7.7 Hz), 121.6, 115.1 (d, $J_{C-F}$=20.9 Hz), 71.8, 57.0, 55.2, 50.0, 42.8, 42.3, 40.4, 39.4, 37.2, 36.5, 31.8, 31.6, 31.3, 31.0, 29.3, 23.7, 22.3, 20.9, 19.4, 13.6, 8.3.

Example 11

Synthesis of (3S,5S,8R,9S,10S,13S,14S,17S)-17-((R)-1-(4-fluorophenyl)-3-hydroxypentan-3-yl)-10,13-dimethylhexadecahydro-1H-cyclopenta[a]phenanthren-3-ol (15)

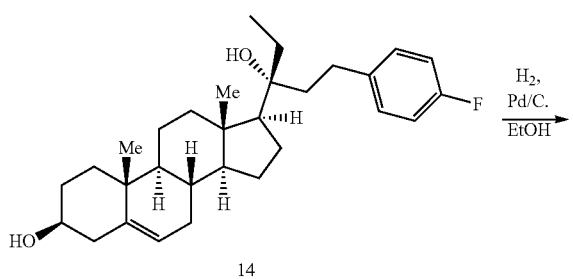

Title compound 15 was prepared from compound 14 in a similar manner as described in Example 6. ¹H NMR (CDCl₃, 400 MHZ) δ 7.14-7.11 (2H, m), 6.97 (2H, dd, J=8.8, 8.8 Hz), 3.54 (1H, dddd, J=10.9, 10.9, 5.5, 5.5 Hz), 2.73-2.64 (2H, m), 2.32-1.22 (15H, m), 1.21 (3H, s), 0.80 (3H, s), 0.76 (3H, s). ¹³C NMR (CDCl₃, 100 MHZ) δ 161.2 (d, J=242 Hz), 138.2 (d, J=3.1), 129.6 (d, J=20 Hz), 115.1 (d, J=20 Hz), 77.4, 71.3, 56.8, 55.3, 54.3, 44.9, 43.1, 40.7, 39.3, 38.2, 37.0, 35.5, 34.9, 31.9, 31.5, 31.0, 29.3, 28.7, 23.6, 22.3, 21.1, 13.8, 12.3, 8.3.

Example 12

Synthesis of Compound 17

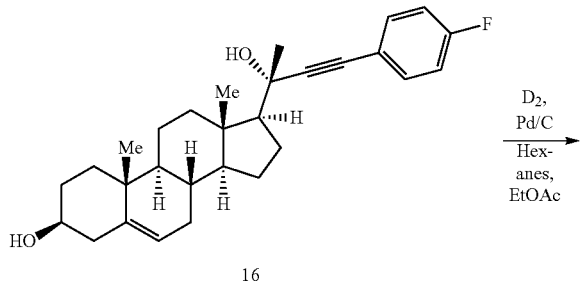

Compound 17 was prepared from compound 16 as outlined in Scheme 1. $^1$H NMR (CDCl$_3$, 400 MHZ) δ 7.14-7.11 (2H, m), 6.97 (2H, dd, J=8.8, 8.8 Hz), 5.33 (1H, m), 3.54 (1H, dddd, J=10.9, 10.9, 5.5, 5.5 Hz), 2.32-1.22 (12H, m), 1.21 (3H, s), 0.99 (3H, s), 0.87 (3H, s), 0.61 (1H, m). $^{13}$C NMR (CDCl$_3$, 100 MHZ) δ 161.2 (d, J=242 Hz), 140.7, 138.2 (d, J=3.1), 129.6 (d, J=20 Hz), 121.4, 115.1 (d, J=20 Hz), 71.6, 58.5, 56.8, 49.9, 43.1, 42.8, 42.2, 37.1, 36.4, 31.5, 31.2, 26.7, 23.7, 23.1, 20.8, 19.3, 13.7.

Example 13

Synthesis of (3S,5S,8R,9S,10S,13S,14S,17S)-17-((S)-4-(4-fluorophenyl)-2-hydroxybutan-2-yl)-10,13-dimethylhexadecahydro-1H-cyclopenta[a]phenanthren-3-ol (18)

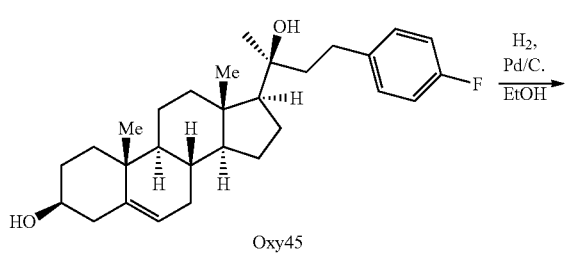

Oxy45

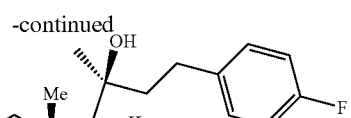

Title compound 18 was prepared from Oxy45 in a similar manner as described in Example 6. $^1$H NMR (CDCl$_3$, 400 MHZ) δ 7.14-7.11 (2H, m), 6.97 (2H, dd, J=8.8, 8.8 Hz), 3.54 (1H, dddd, J=10.9, 10.9, 5.5, 5.5 Hz), 2.73-2.64 (2H, m), 2.32-1.22 (14H, m), 1.25 (3H, s), 0.87 (3H, s), 0.81 (3H, s), 0.61 (1H, m). $^{13}$C NMR (CDCl$_3$, 100 MHZ) δ 161.2 (d, J=242 Hz), 138.2 (d, J=3.1), 129.6 (d, J=20 Hz), 115.1 (d, J=20 Hz), 75.0, 71.2, 58.1, 56.6, 54.2, 45.6, 44.8, 42.9, 40.4, 38.1, 36.9, 35.4, 34.8, 31.8, 31.4, 29.7, 28.6, 26.1, 23.6, 22.4, 21.0, 13.7, 12.2.

Example 14

Expression of Hedgehog Target Genes PTCH and Gli1

The compounds described herein were tested on cell cultures to assess their effects on Hedgehog target genes PTCH and Gli1. Conditioned medium (CM) was collected from CAPAN-1 human pancreatic tumor cells grown to confluence and contains Hh proteins that activate the Hh pathway in cells receiving the CM. The CM was incubated with DMEM containing 10% fetal bovine serum (FBS). After 7 days of incubation, CM was collected, spun for 5 minutes at 1800 rpm to remove dead cells and debris, and then frozen at −80° C. For treating cells, CM was thawed and diluted 1:1.5 with DMEM containing 5% FBS. NIH3T3 cells, HepG2 and SUFU−/−MEF cells were cultured in 12-well plates with DMEM containing 10% FBS. The cells were then treated with DMEM containing 5% FBS or CM in the presence or absence of the compounds in DMSO when they reach confluence. Quantitative RT-PCR was then performed according to the following approach. After 72 to 96 hours of the treatments, the cells were lysed and subjected to RNA extraction with RNease Plus Min kit (Qiagen). A portion of RNA from each well was subjected to Reverse Transcription (RT) using iScript Reverse Transcription Supermix (BioRad). QPCR was performed to test the expression of Hh target genes PTCH and Gli1 using IQ SYBR Green Supermix (BioRad).

Figure 1:
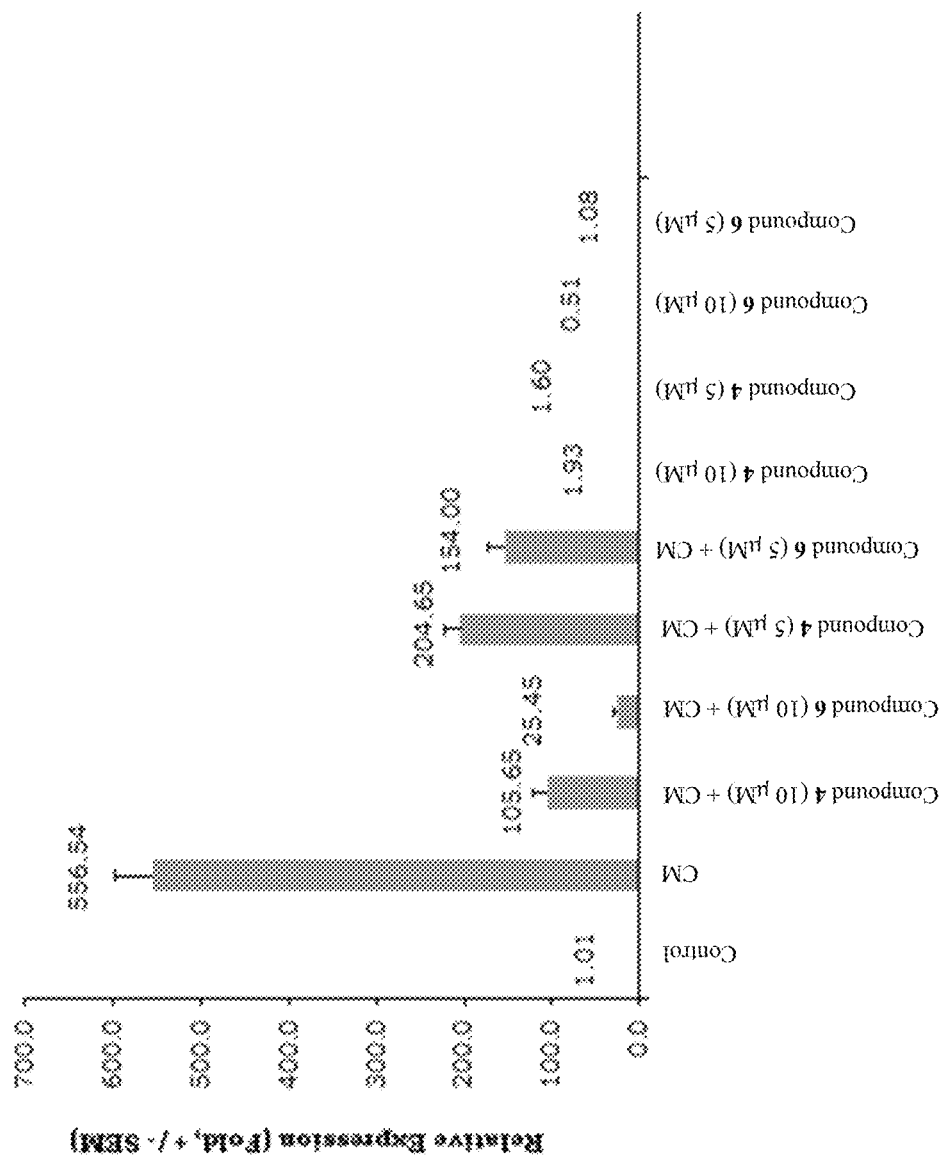
FIG. 1 shows the relative expression of Hedgehog target gene Gli1 in NIH3T3 cells. The relative expression (fold) of Gli1 is plotted for compound 4 and compound 6, each at concentrations of 5 µM and 10 µM in conditioned medium (CM) or 5% FBS in DMEM in comparison with a control (DMSO alone) and CM.
Figure 2:
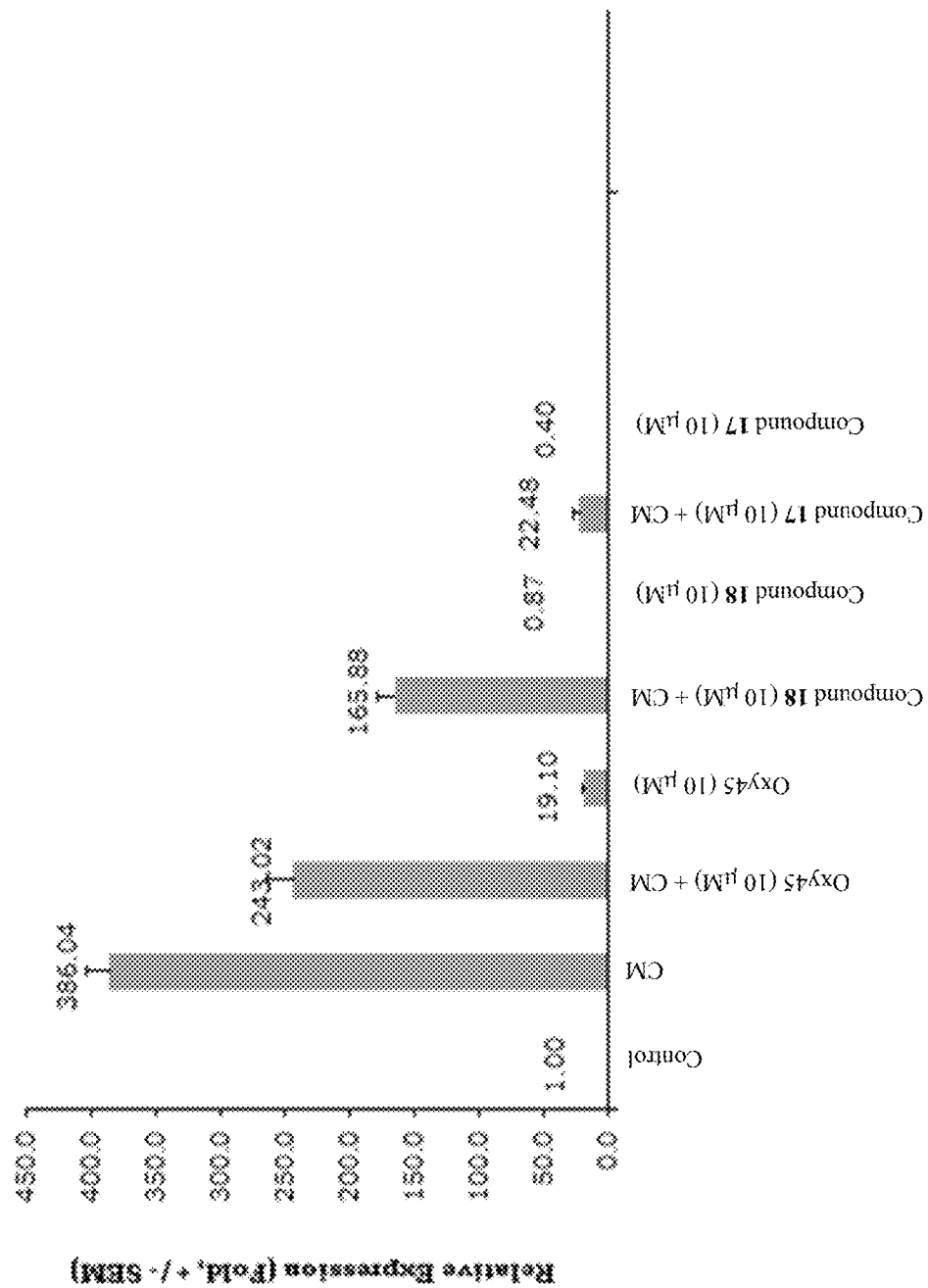
FIG. 2 shows the relative expression of Hedgehog target gene Gli1 in NIH3T3 cells. The relative expression (fold) of Gli1 is plotted for Oxy45, compound 17 and compound 18, each at a concentration of 10 µM in conditioned medium (CM) or 5% FBS in DMEM in comparison with a control (DMSO alone). Oxy45 is

The hedgehog inhibitor compounds described herein inhibit the expression of Hedgehog target genes, PTCH and Gli1 (FIGS. 1-6). As shown in the figures, inhibition of Gli1 expression is increased for compound 6 (C20 R-steroechemistry, C5-C6 single bond) vs. compound 18 (C20 S-steroechemistry, C5-C6 single bond) (FIGS. 1 and 3) and for compound 6 (C5-C6 single bond, C20 R-steroechemistry) vs. compound 4 (C5-C6 double bond, C20 R-steroechemistry) (FIG. 1).

What is claimed is:

1. A compound having the structure of Formula (I):

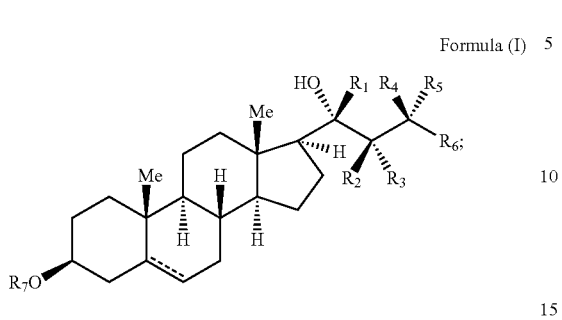

Formula (I)

wherein:
- $R_1$ is substituted or unsubstituted $C_1$-$C_8$ alkyl, substituted or unsubstituted $C_1$-$C_8$ alkenyl, substituted or unsubstituted $C_1$-$C_8$ alkynyl, substituted or unsubstituted aryl, substituted or unsubstituted heteroaryl, or substituted or unsubstituted —$C_1$-$C_4$ alkylaryl;
- $R_6$ is substituted or unsubstituted aryl or substituted or unsubstituted heteroaryl;
- ===== is a single or double bond;
- $R_2$, $R_3$, $R_4$, and $R_5$ are independently hydrogen, deuterium, or —OH;
- $R_7$ is hydrogen, substituted or unsubstituted $C_1$-$C_8$ alkyl, or —C(O)$NR_8R_9$; and
- $R_8$ and $R_9$ are independently hydrogen, substituted or unsubstituted $C_1$-$C_8$ alkyl, or substituted or unsubstituted aryl.

2. The compound of claim 1, wherein $R_1$ is substituted or unsubstituted $C_1$-$C_8$ alkyl or substituted or unsubstituted phenyl.

3. The compound of claim 2, wherein $R_1$ is substituted or unsubstituted $C_1$-$C_8$ alkyl.

4. The compound of claim 3, wherein $R_1$ is —$CF_3$.

5. The compound of claim 3, wherein $R_1$ is unsubstituted $C_1$-$C_4$ alkyl.

6. The compound of claim 5, wherein $R_1$ is —$CH_3$.

7. The compound of claim 5, wherein $R_1$ is —$CH_2CH_3$.

8. The compound of claim 1, wherein $R_6$ is substituted or unsubstituted phenyl.

9. The compound of claim 8, wherein $R_6$ is substituted phenyl.

10. The compound of claim 9, wherein $R_6$ is 4-fluorophenyl.

11. The compound of claim 1, wherein $R_2$, $R_3$, $R_4$, and $R_5$ are independently hydrogen or deuterium.

12. The compound of claim 11, wherein $R_2$, $R_3$, $R_4$, and $R_5$ are each hydrogen.

13. The compound of claim 1, wherein $R_7$ is hydrogen or substituted or unsubstituted $C_1$-$C_8$ alkyl.

14. The compound of claim 13, wherein $R_7$ is unsubstituted $C_1$-$C_8$ alkyl.

15. The compound of claim 14, wherein $R_7$ is —$CH_3$.

16. The compound of claim 13, wherein $R_7$ is hydrogen.

17. The compound of claim 1, wherein ===== is a single bond.

18. The compound of claim 1, wherein ===== is a double bond.

19. A compound having a structure selected from:

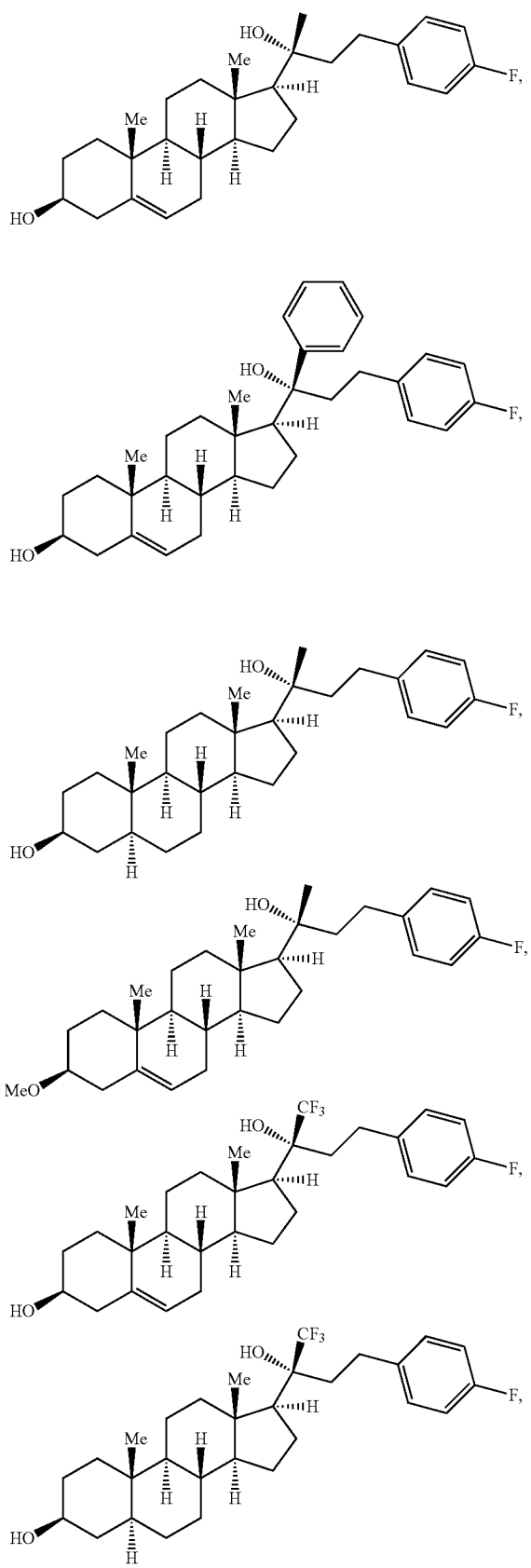

-continued
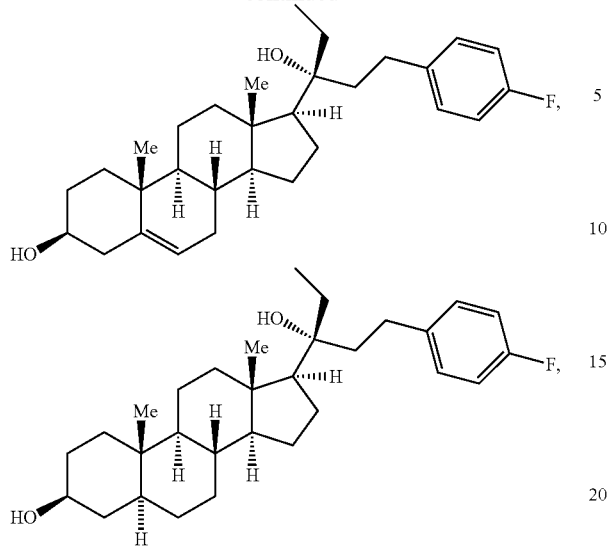
-continued
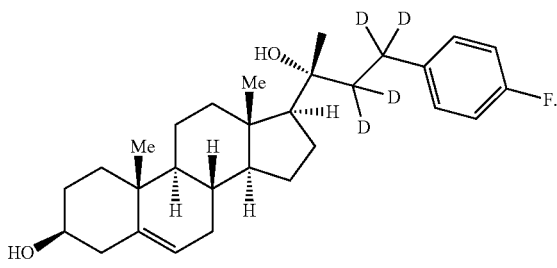
20. A pharmaceutical composition comprising a compound of claim 1 and a pharmaceutically acceptable excipient.
* * * * *